(12) United States Patent
Dewey

(10) Patent No.: US 11,964,074 B2
(45) Date of Patent: Apr. 23, 2024

(54) ADDITIVE-MANUFACTURED NON-WOVEN FIBROUS IMPLANTS, SYSTEMS, AND RELATED METHODS

(71) Applicant: Warsaw Orthopedic, Inc., Warsaw, IN (US)

(72) Inventor: Jonathan M. Dewey, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 538 days.

(21) Appl. No.: 17/069,981

(22) Filed: Oct. 14, 2020

(65) Prior Publication Data
US 2022/0111116 A1 Apr. 14, 2022

Related U.S. Application Data

(63) Continuation-in-part of application No. 16/716,697, filed on Dec. 17, 2019, now Pat. No. 11,523,916, and (Continued)

(51) Int. Cl.
*A61F 2/44* (2006.01)
*A61L 27/12* (2006.01)
(Continued)

(52) U.S. Cl.
CPC .............. *A61L 27/12* (2013.01); *A61L 27/54* (2013.01); *B29C 64/209* (2017.08);
(Continued)

(58) Field of Classification Search
CPC ...... A61L 27/12; A61L 27/54; A61L 2400/06; A61L 2430/38; B29C 64/209;
(Continued)

(56) References Cited

U.S. PATENT DOCUMENTS 7,051,654 B2    5/2006  Boland et al.
7,875,324 B2    1/2011  Barron et al.
(Continued)

FOREIGN PATENT DOCUMENTS

CN    204092271 U    1/2015
CN    104688388 A    6/2015
(Continued)

OTHER PUBLICATIONS

Xie Sheng et al, "Turbulent Air Flow Field and Fiber Whipping Motion in the Melt Blowing Process: Experimental Study", Industrial & Engineering Chemistry Research, vol. 51, No. 14, Apr. 11, 2012 (Apr. 11, 2012), pp. 5346-5352, XP055896821, ISSN: 0888-5885, DOI: 10.1021/ie202938b.
(Continued)

*Primary Examiner* — Tessa M Matthews
*Assistant Examiner* — David C Comstock
(74) *Attorney, Agent, or Firm* — FOX ROTHSCHILD LLP

(57) ABSTRACT

Additive-manufacturing systems for forming non-woven fibrous implants are disclosed. Additive-manufacturing systems may include a robotic subsystem having scanning and imaging equipment configured to scan a patient's anatomy, and an armature including at least one dispensing nozzle configured to selectively dispense at least one material. The system may further include a controller apparatus configured to send a control signal to control the scanning and imaging equipment to determine a target alignment of a patient's spine, and develop an additive-manufactured printing plan including an additive-manufactured material selection plan based on the target alignment of the patient's spine. The controller may execute the additive-manufactured printing plan to: dispense the at least one material to form a non-woven fibrous component. The non-woven fibrous compo- (Continued)

nent may define a plurality of randomly oriented fibers further defining a plurality of open pore spaces between adjacent fibers configured to facilitate boney ingrowth between adjacent fibers.

19 Claims, 45 Drawing Sheets

Related U.S. Application Data a continuation-in-part of application No. 16/716,771, filed on Dec. 17, 2019, now Pat. No. 11,523,909, and a continuation-in-part of application No. 16/907,341, filed on Jun. 22, 2020, and a continuation-in-part of application No. 16/986,869, filed on Aug. 6, 2020, and a continuation-in-part of application No. 16/992,432, filed on Aug. 13, 2020.

(51) Int. Cl.
| | |
|---|---|
| A61L 27/54 | (2006.01) |
| B29C 64/209 | (2017.01) |
| B29C 64/393 | (2017.01) |
| A61F 2/30 | (2006.01) |
| B33Y 10/00 | (2015.01) |
| B33Y 30/00 | (2015.01) |
| B33Y 80/00 | (2015.01) |

(52) U.S. Cl.
CPC .. *B29C 64/393* (2017.08); *A61F 2002/30985* (2013.01); *A61F 2002/4495* (2013.01); *A61L 2400/06* (2013.01); *A61L 2430/38* (2013.01); *B33Y 10/00* (2014.12); *B33Y 30/00* (2014.12); *B33Y 80/00* (2014.12)

(58) Field of Classification Search
CPC ....... B29C 64/393; B33Y 10/00; B33Y 30/00; B33Y 80/00; A61F 2002/30985; A61F 2002/4495
USPC ............................ 606/279; 623/17.11, 17.15
See application file for complete search history.

(56) References Cited

U.S. PATENT DOCUMENTS

| | | | | |
|---|---|---|---|---|
| 7,909,876 | B2 * | 3/2011 | Dooris | A61F 2/4425 |
| | | | | 623/17.14 |
| 9,020,788 | B2 * | 4/2015 | Lang | A61B 17/1764 |
| | | | | 703/6 |
| 9,626,989 | B1 | 4/2017 | Buch et al. | |
| 10,442,182 | B2 * | 10/2019 | Varanasi | B33Y 10/00 |
| 10,492,875 | B2 | 12/2019 | Janik et al. | |
| 10,736,698 | B2 | 8/2020 | Bohl | |
| 11,033,336 | B2 | 6/2021 | Bohl | |
| 11,523,916 | B2 | 12/2022 | Dewey et al. | |
| 2003/0078667 | A1 * | 4/2003 | Manasas | A61F 2/442 |
| | | | | 623/17.15 |
| 2006/0276925 | A1 * | 12/2006 | Lin | A61F 2/30942 |
| | | | | 606/85 |
| 2008/0109081 | A1 * | 5/2008 | Bao | A61F 2/4425 |
| | | | | 623/47 |
| 2014/0207235 | A1 | 7/2014 | Drapeau | |
| 2016/0129155 | A1 | 5/2016 | Lin et al. | |
| 2016/0288414 | A1 | 10/2016 | Ozbolat et al. | |
| 2016/0374770 | A1 | 12/2016 | Janik et al. | |
| 2017/0238984 | A1 | 8/2017 | Kleiner | |
| 2018/0092755 | A1 * | 4/2018 | Lechmann | A61F 2/442 |
| 2018/0243094 | A1 | 8/2018 | Jones et al. | |
| 2018/0368992 | A1 | 12/2018 | Zink et al. | |
| 2019/0008655 | A1 | 1/2019 | Body | |
| 2019/0029842 | A1 | 1/2019 | Xiao et al. | |
| 2019/0099515 | A1 | 4/2019 | Bagga et al. | |
| 2021/0007778 | A1 | 1/2021 | Shoham | |
| 2021/0093457 | A1 | 4/2021 | Hodrinsky et al. | |

FOREIGN PATENT DOCUMENTS

| | | | | |
|---|---|---|---|---|
| CN | 105287059 | A | 2/2016 | |
| CN | 105751510 | A | 7/2016 | |
| CN | 106361431 | A | 2/2017 | |
| CN | 206491869 | U | 9/2017 | |
| DE | 102015222117 | A1 | 5/2017 | |
| EP | 3045150 | A1 | 7/2016 | |
| EP | 3603580 | A1 | 2/2020 | |
| EP | 3666231 | A1 | 6/2020 | |
| EP | 3954318 | A1 | 2/2022 | |
| WO | 2015066705 | A1 | 5/2015 | |
| WO | WO-2015131234 | A1 * | 9/2015 | A61F 2/28 |
| WO | 2016/210081 | A1 | 12/2016 | |
| WO | 2017/080646 | A1 | 5/2017 | |
| WO | 2018185755 | A1 | 10/2018 | |
| WO | 2018193316 | A2 | 10/2018 | |
| WO | 2020069012 | A2 | 4/2020 | |
| WO | 2021126702 | A1 | 6/2021 | |

OTHER PUBLICATIONS

European Search Report in Application No. 21196870.6 dated Mar. 15, 2022.
Ashammakhi Nureddin et al: "In situ three-dimensional printing for reparative and regenerative therapy", Biomed Microdevices, Kluwer Dordrecht, NL, vol. 21, No. 2, Apr. 6, 2019, pp. 1-6.
Manyi Wang et al: "The trend towards in vivo bioprinting", International Journal of Bioprinting, Jul. 2, 2015.
International Search Report for PCT/US2021/037882 dated Oct. 19, 2021.
European Search Report in Application No. 21189618.8 dated Jan. 14, 2022.
Cui et al. "Direct Human Cartilage Repair Using Three-Dimensional Bioprinting Technology," Tissue Engineering: Part A, 2012, vol. 18, No. 11 & 12, pp. 1304-1312.
Di Bella et al. "In situ handheld three-dimensional bioprinting for cartilage regeneration," Journal of Tissue Engineering for Regenerative Medicine, Mar. 2018, vol. 12, No. 3, pp. 611-621.
Hong et al. "3D bioprinting and its in vivo applications," Journal of Biomedical Materials Research Part B: Applied Biomaterials, Jan. 2018, vol. 106, No. 1, pp. 444-459.
O'Connell et al. "Development of the Biopen: a handheld device for surgical printing of adipose stem cells at a chondral wound site," Biofabrication, Mar. 2016, vol. 8, No. 1, 015019.
Rengier et al. "3D printing based on imaging data: review of medical applications," International Journal of Computer Assisted Radiology Surgery, Jul. 2010, vol. 5, No. 4, pp. 335-341.
Wang et al. "The trend towards in vivo bioprinting," International Journal of Bioprinting, 2015, vol. 1, No. 1, pp. 15-26.
European Search Report in Application No. 21191309.0 dated Jan. 18, 2022.

* cited by examiner

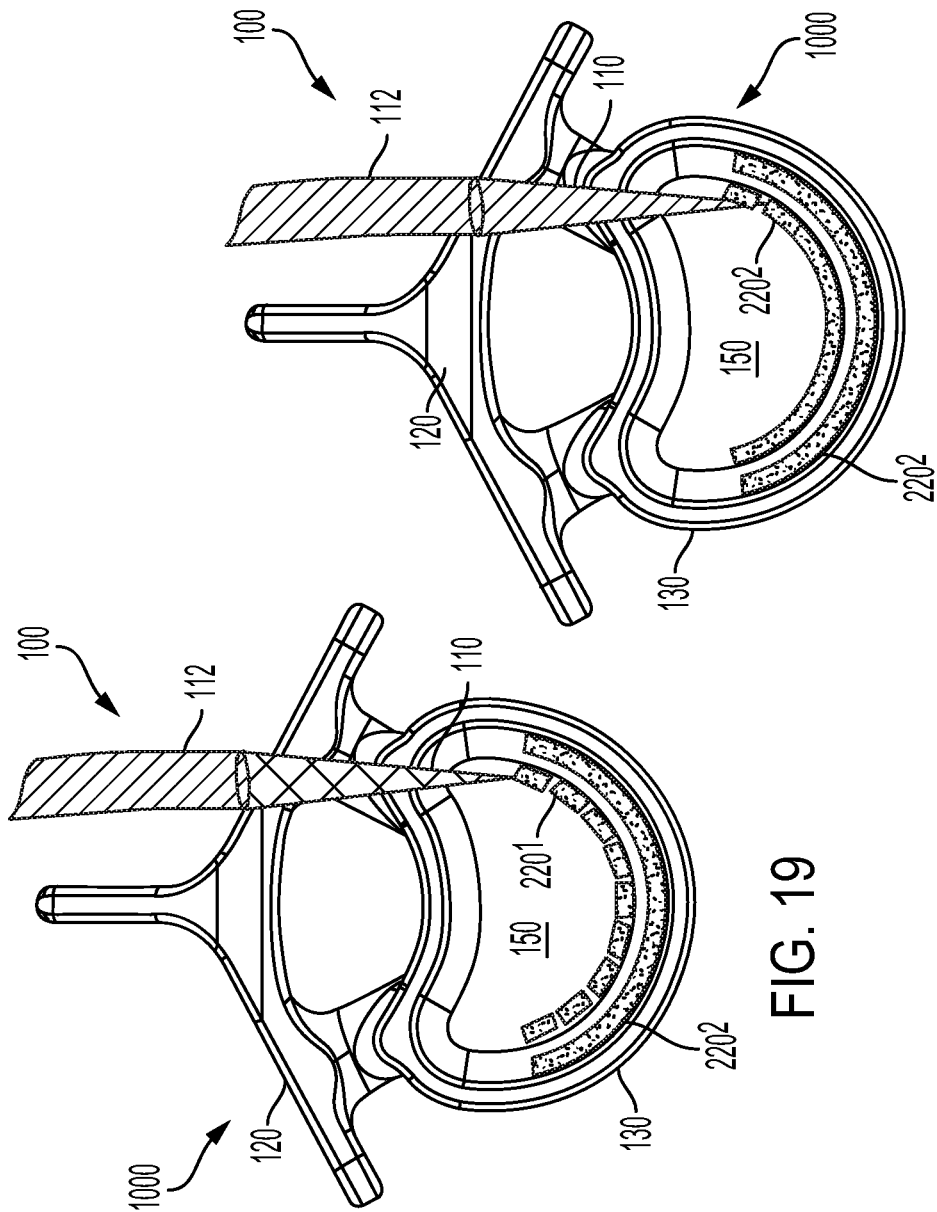

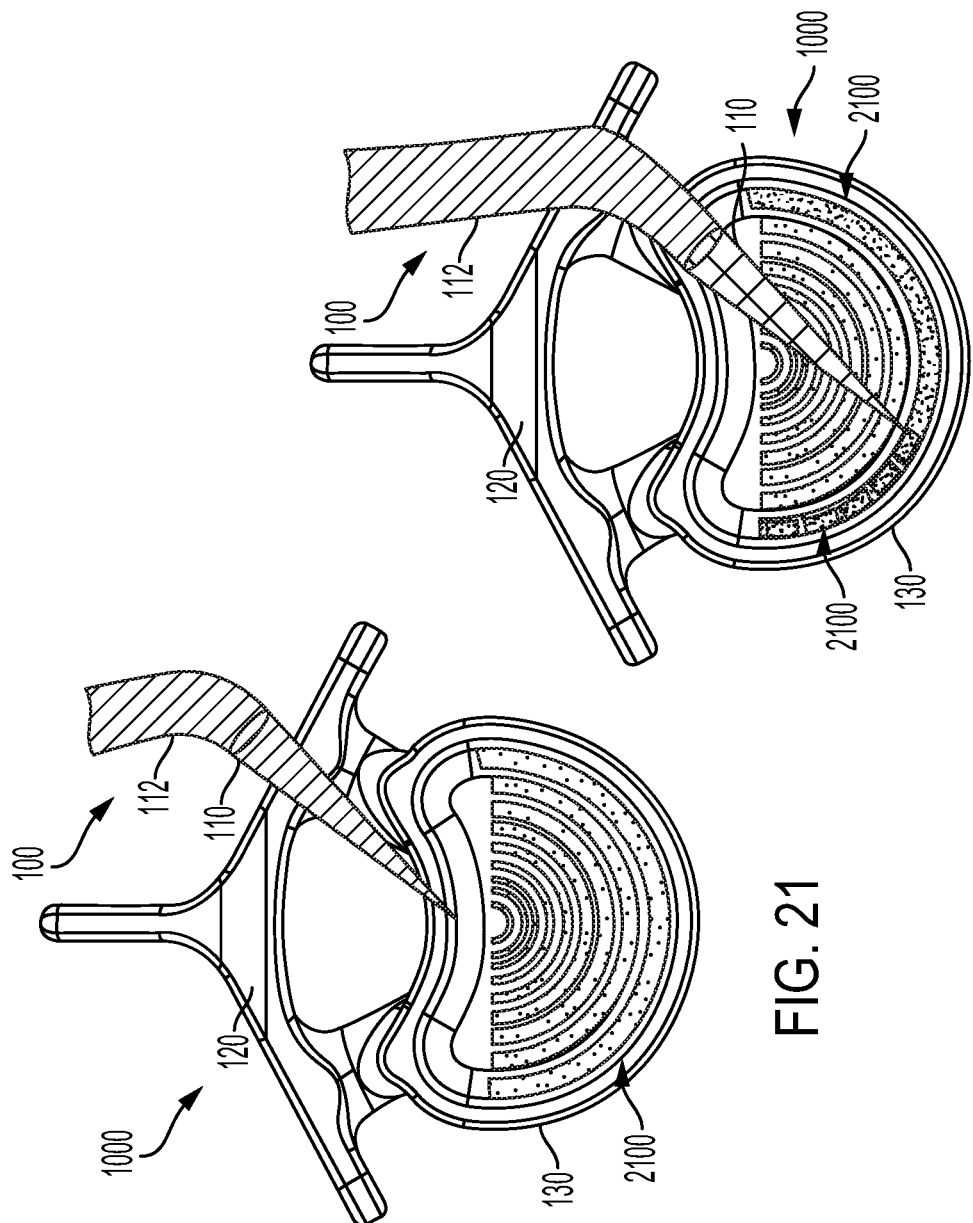

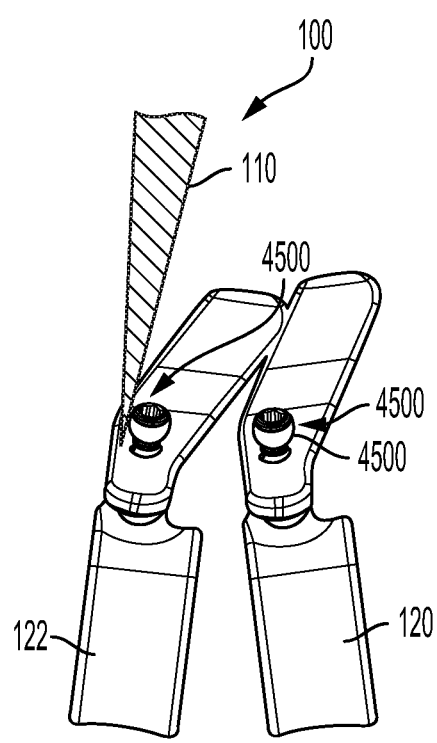
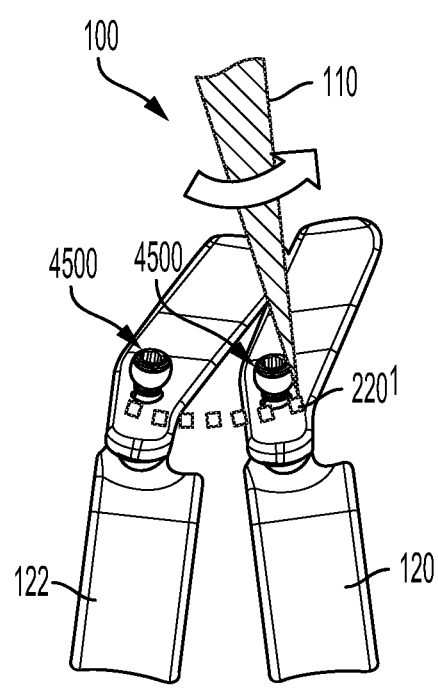
FIG. 48
FIG. 49

ADDITIVE-MANUFACTURED NON-WOVEN FIBROUS IMPLANTS, SYSTEMS, AND RELATED METHODS

CROSS-REFERENCE TO RELATED APPLICATIONS

This application is a continuation in part of U.S. application Ser. No. 16/716,697, filed Dec. 17, 2019, U.S. application Ser. No. 16/716,771, filed Dec. 17, 2019, U.S. application Ser. No. 16/907,341, filed Jun. 22, 2020; U.S. application Ser. No. 16/986,869, filed Aug. 6, 2020; and U.S. application Ser. No. 16/992,432, filed Aug. 13, 2020. The contents of each are herein incorporated in their entireties.

FIELD

The present technology is related generally to additive-manufacturing systems and processes for forming patient implants that include fibers and/or a plurality of fiber based layers. In some embodiments, patient implants or portions thereof may be formed in-situ, at a surgical center where the patient implant is to be installed, at a manufacturing center in advance of installation, and various locations and/or combinations thereof. Techniques of the present technology may be discussed as forming patient implants "in-situ" and it shall be understood that such techniques are equally applicable to forming patient implants at surgical centers and manufacturing centers alike whether or not those techniques are technically performed "in-situ." When the term "in-situ" is used, it is intended to mean that at least one portion or manufacturing step is performed at a surgical center at a time and location proximate to a surgery of a patient unless the context clearly indicates otherwise.

BACKGROUND

Additive manufacturing processes have been used increasingly to make a wide variety of parts, including medical implants. An example implant is a spinal interbody, or cage.

Advances in additive-manufacturing technology and material science have expanded the types and configurations of parts that can be printed, including parts having internal or otherwise intricate features that were not possible before.

Conventional additively-manufactured implants may have various shortcomings.

Some of the shortcomings may relate to the fact that they are typically pre-manufactured in mass quantities. They are thus not customized, specific to particular patient anatomy, for instance. They are, rather, one-size/shape fits many.

Some product lines offer multiple size options. Even so, product geometry may still be somewhat generic.

As another shortcoming, conventional parts can be difficult or impossible to implant because of access issues. There may be patient tissue partially blocking the implant from being delivered to the target implant position. Other access related issues may occur from collapsed or partially collapsed adjacent vertebrae that block access to the area between the adjacent vertebrae.

As yet another shortcoming, there are undesirable costs related to off-site manufacture. These include cost of packaging, shipping, tracking, storage, and retrieving and preparing for implantation.

In some medical procedures, multiple parts may be implanted. In some of these cases, the parts are connected prior to or during surgery to form a construct. In some conventional spinal surgeries, for instance, a construct of pre-manufactured components is assembled to fix adjacent patient vertebrae together, to limit relative movement between the vertebrae. Fixing relative position between select vertebrae alleviates or obviates implications such as nerve impingement or problematic intervertebral contact. Such implications can result from trauma or the intervertebral disc being compromised. The fixation can also cause adjacent vertebrae to fuse, or grow, together.

In addition to the mentioned potential shortcomings of pre-made implants, shortcomings specific to implant assemblies may include additional labor associated with fitting and connecting components manually.

And no matter the type of conventional implant, there may be a challenge ensuring precise positioning in the patient.

An additional challenge with conventional patient implants is that they are commonly formed or machined from solid blocks of material, injection molded material, or sequentially stacked consistent solid layers of material. Accordingly, to form a porous or semi porous patient implant material must be removed from the solid blocks and/or solid layers of material, e.g., by machining techniques. Although these techniques may create a porous or semi porous patient implant they are inherently limited by the capability of machining techniques, e.g., drilling, cutting, bending, etc. which consequently result in regular, planned patterns of pores and open void spaces.

Solutions to the above challenges are desired for spinal surgeries, other medical procedures calling for an implant, and other industries involving some sort of device, whether or not referred to as an implant, including outside of the medical industry.

SUMMARY

The systems and process of the techniques of this disclosure relate generally to additive-manufacturing systems and processes for forming parts or devices in-situ, such as in a patient during surgery, or in advance of surgery/installation at a medical center or a manufacturing center. The present disclosure proposes, for example, manufacturing interbody implants having a porous composition including randomly sized and spaced pores (void spaces and/or open spaces). At least one advantage to the aforementioned implants is that the human body can more easily grow boney structures into randomized void spaces as opposed to regular, planned patterns of void spaces.

For example, at least one object of the present application is the formation of a patient implant including porous gaps created by randomly overlaying fiber based materials to a desired height or thickness to create randomly spaced and sized porous gaps between overlaid fibers. Such randomly spaced and sized porous gaps may provide an increased ability to promote boney ingrowth therebetween compared to regular, planned patterns of pores and open void spaces in conventional patient implants. Additionally, such porous gaps may provide a scaffolding substrate for motion-sparing implants where such pores may selectively be filled with a non-rigid material.

In one aspect, the present disclosure provides, for example, for a non-woven fibrous implant. The non-woven fibrous implant may include: a first endcap formed of a rigid material and having a size corresponding to size of a first vertebral body; a second endcap formed of a rigid material and having a size corresponding to size of a second vertebral body; and at least one non-woven fibrous component comprising a plurality of randomly spaced and oriented fibers defining a plurality of open pore spaces between adjacent fibers. In some embodiments, the open pore spaces are configured to promote boney ingrowth between adjacent fibers.

In another aspect, for example, the at least one non-woven fibrous component may be configured to be exposed, at least partly, to patient tissue upon being positioned between adjacent vertebrae of a patient.

In another aspect, the at least one non-woven fibrous component may be coated with a bone-growth-promoting material.

In another aspect, the at least one non-woven fibrous component may include calcium and/or phosphate.

In another aspect, at least one pliable material layer may be disposed between the first and second endcaps, the pliable material may be configured to provide a motion-sparing effect.

In another aspect, at least one of the first endcap, the second endcap, and the pliable material may be printed and cured in-situ within a disc space of a patient, between the first and second vertebral bodies.

In another aspect, each of the first endcap, the second endcap, and the pliable material may be printed and cured in-situ within a disc space of a patient.

In another aspect, the at least one non-woven fibrous component may be cut from a batch of fibrous material extruded directly in a turbulent airflow environment.

In another aspect, the first endcap and the second endcap may be formed of rigid material dispensed by the dispensing component.

In another aspect, the first endcap and the second endcap may be provided from pre-formed metallic material.

In another aspect, for example, an additive-manufacturing system for forming at least one non-woven fibrous implant is disclosed. The system may include a robotic subsystem including: scanning and imaging equipment configured to scan a patient's anatomy; and an armature including at least one dispensing nozzle configured to selectively dispense at least one rigid material and at least one pliable material. The system may further include: a controller apparatus having a processor and a non-transitory computer-readable medium storing computer-executable instructions. The instructions may cause the controller to: send a control signal to control the scanning and imaging equipment to determine a target alignment of a patient's spine; develop an additive-manufactured printing plan including an additive-manufactured material selection plan based on the target alignment of the patient's spine; and execute the additive-manufactured printing plan. The printing plan may control the armature to dispense the at least one material chosen from the at least one rigid material and the at least one pliable material to form a non-woven fibrous component. In some embodiments, the non-woven fibrous component defines a plurality of randomly oriented fibers further defining a plurality of open pore spaces between adjacent fibers configured to facilitate boney ingrowth between adjacent fibers.

In another aspect, a provisioning component for affecting a rate of flow of printing material and a type of printing material through the dispensing component may be provided. In some embodiments, the controller may be further configured to control the provisioning component on the basis of the additive-manufactured printing plan and the additive-manufactured material selection plan.

In another aspect, the controller may be further configured to control forming the at least one non-woven fibrous component from an extruded material subjected to a turbulent airflow.

In another aspect, an extruder may be configured to extrude fibrous material into an environment subjected to a turbulent airflow.

In another aspect, extruder and a pumping system may be configured to pump extrudate to the dispensing component, and the dispensing component may eject the extrudate into an environment subjected to a turbulent airflow to form the at least one non-woven fibrous component.

In another aspect, a robotic armature may be provided. In some embodiments, the controller may send a control signal directing the robotic armature to place the at least one non-woven fibrous component inside a patient. Additionally, the computer-executable instructions may be further configured to, when executed by the processor, cause the controller to send a control signal directing the dispensing component to print at least one of a rigid material and pliable material in-situ within the patient that directly contacts the non-woven fibrous component.

In another aspect, for example, a method for printing an additive manufactured non-woven fibrous implant is disclosed. The method may include the steps of: positioning, in a first positioning step, a dispensing component proximate to an environment subjected to a turbulent airflow; printing, in a printing step, a fibrous material within the environment subjected to the turbulent airflow to form at least one non-woven fibrous component; coupling at least one rigid material to the at least one non-woven fibrous component; and placing the non-woven fibrous component inside an interbody access space of a patient.

In another aspect, the method may include providing an additive-manufacturing system including a robotic subsystem and a controller apparatus having a processor and a non-transitory computer-readable medium storing additive manufactured printing instructions; and executing the additive manufactured printing instructions to control the robotic subsystem to perform the printing steps.

In another aspect, the additive-manufacturing system may further include a provisioning component affecting flow of printing material to or through the dispensing component; and the controller apparatus, in the printing step, may control the provisioning component based on turbulent airflow data to control a rate at which the printing material is dispensed.

In another aspect, the method may include printing another rigid material or a pliable material within or adjacent to the interbody access space of the patient that directly contacts the non-woven fibrous component.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 19 shows the dispensing component completing deposit of the subsequent row of substrate material at the in-situ position of the patient according to the first general embodiment of the present technology.

FIG. 20 shows the dispensing component depositing catalyst over the subsequent-row substrate material at the in-situ position of the patient according to the first general embodiment of the present technology.

FIG. 21 shows an example first layer of the additive in-situ implant completed according to the first general embodiment of the present technology.

FIG. 22 shows the dispensing component beginning formation of a subsequent layer of substrate material over the first layer at the in-situ position of the patient according to the first general embodiment of the present technology.

FIG. 48 is a lateral view of the dispensing component of the additive-manufacturing system positioned at an example starting position adjacent one of the fiducial screws, or at least adjacent one of the patient vertebrae, for commencing depositing printing material for growing a fusion implant in-situ, according to the seventh general embodiment of the present disclosure.

FIG. 49 is a lateral view of the dispensing component of the additive-manufacturing system applying substrate material between the vertebrae for in-situ printing the implant, connecting the screws and thereby the vertebrae, according to the seventh general embodiment of the present disclosure.

DETAILED DESCRIPTION

Figure 1:
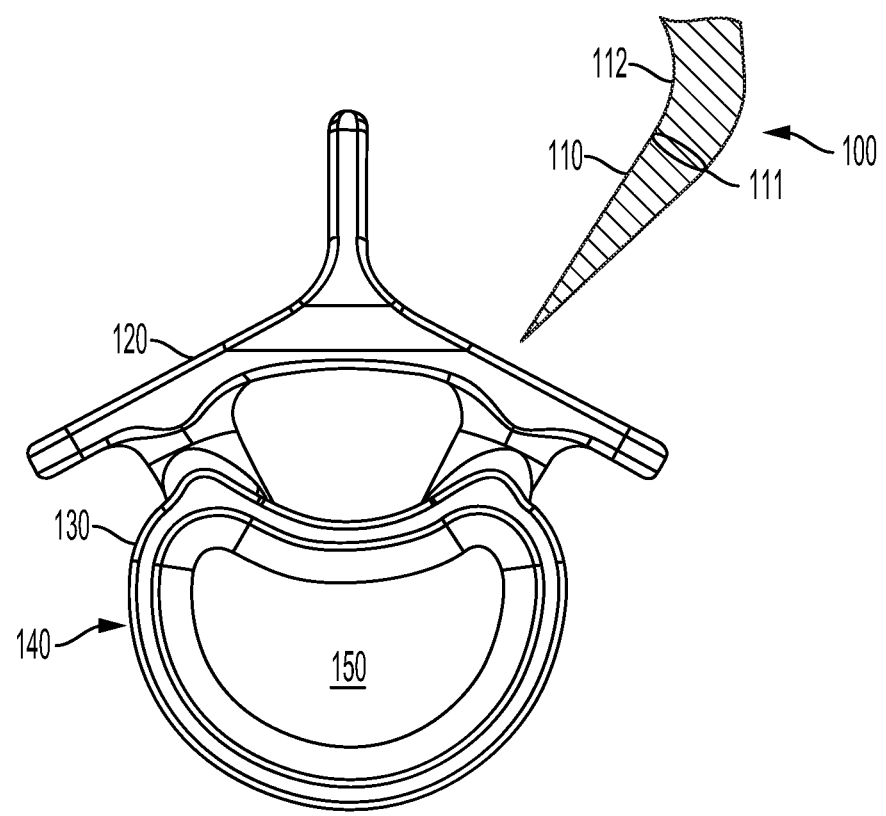
FIG. 1 is an axial view of a dispensing component of a surgical additive-manufacturing system positioned adjacent a patient vertebra according to a general embodiment of the present disclosure.

While the present technology is described primarily in the context of spinal implants, the technology is not limited to use with spinal surgery, or even to use for medical procedures. The technology can be used for making devices, whether referred to as implants, for other industries, such as construction or automotive, for instance.

Descriptions provided herein regarding medical procedures can, thus, be analogized to the other industries, such as filters/filtration, insulators/insulation. The descriptions are thus to be understood to include inherently disclosure of such other analogous implementations. Descriptions herein of printing a unique component between or adjacent two vertebrae, in ways that cannot be done with a conventional fully pre-made spinal implant—due to access, fit, or geometry challenges, for instance—thus include thereby disclosure of analogous processes for printing non-medical implants at least partially in-situ, for overcoming the similar access, fit, or geometry challenges. The technology can be used readily to connect more than two vertebra (a single-level procedure), in a multi-level procedure connecting any number of vertebra.

As another example of analogous interpretation, of disclosure from spinal procedures to other medical procedures and other-industry procedures, elimination of fiscal or labor costs described in connection with spinal- or medical-industry implementation relates to fiscal or labor savings achievable in any other industry in which the technology can be used.

Spinal implants are often used to fix together two or more adjacent vertebrae. Fixing relative position between select vertebrae alleviates or obviates implications such as nerve impingement or problematic intervertebral contact. Such implications can result from trauma or the intervertebral disc having become compromised. Though fusing vertebrae together limits patient flexibility, fixing relative position between select vertebrae promotes continued alleviation of said implications.

Benefits from using the technology include the ability to custom-make implants, such as spinal implants, that are particular to a subject-patient anatomy. Benefits also include the ability to make patient-specific implants having geometries that are otherwise impossible or prohibitive to make.

Advantageous geometries from growing implants in-situ according to the present technology include those that can realize a specific desired final positioning in the patient. These advantages include advantages stemming from obviating challenges in maneuvering a complete pre-manufactured implant into place in the patient.

The advantages include allowing or improving issues relating to access, fit, and part placement, including orientation. Regarding access, for instance, the present technology in many implementations allows printing of implants in spaces having clearance challenges making implantation of conventional pre-made implants difficult, prohibitive, or impossible. Fit advantages include the ability to achieve highly accurate positioning and orientation adjacent the patient, such as between or adjacent patient vertebrae.

Benefits from the present technology also include obviating or reducing any of various cost factors, such as cost of packaging, shipping, tracking, storage, and retrieving and preparing for implantation.

The present technology can also eliminate some or all manual steps involved with conventional implanting, depending on the implementation of the present disclosure employed.

As referenced, benefits from the present technology can also include any of those applicable in other industries. These can include any of those referenced herein for spinal or medical implants, such as the ability to grow or form custom-fit implants, and various cost savings (obviating part-shipping, storage, and tracking, for instance).

Another common benefit between medical and other-industry applications can include access, or the ability to deliver parts to a position or orientation that would be difficult or impossible to get the parts to otherwise.

An ability to grow or form implants according to disclosed additive manufacturing techniques also gives an ability to grow or form the implants to have more than one material, selected and printed in portions of the implant and with geometries determined best suited to perform in the patient as desired. For example, disclosed additive-manufactured implants may have varying mechanical properties such as porosity, strength, ductility, hardness, flexibility, impact resistance, elasticity, and fracture toughness. Furthermore, disclosed additive-manufactured non-woven fibrous implants may be anisotropic in that their material properties may vary with orientation and/or by layer. In some applications, additive-manufactured non-woven fibrous implants may be isotropic in that their material properties may be the same regardless of orientation and/or layer.

In some embodiments, an additional material grown, formed, or added is a bone-growth-promoting material (BGM). The material can also be injected in-situ into additive-manufactured non-woven fibrous implants, such as when the implant is only partially grown or formed, and the BGM can best be deposited to desired intra-implant positions. Additionally or alternatively, additive-manufactured non-woven fibrous implants may be coated or dipped in BGM material and then encapsulated by an iterative printing process performed in-situ. In some embodiments, Medtronic's skellite product may be included within non-woven fibrous implants and/or coated over non-woven fibrous implants. In some embodiments, BGM material may be added to or incorporated with various disclosed materials before being extruded, for example in a hopper and/or mixing chamber of an extruder. Additionally, BGM material may range in volume/volume ratio relationship with the extruded material such that the BGM portion may be less than 10% volume of the extrudate material which may give intermittent bone attaching spots. Furthermore, the BGM material portion may relatively high, e.g., greater than 90%, such that the extruded material may act or function as a binder between particles of BGM material. The BGM portion may also be between less-than-10% and greater-than-90%, as needed for the surgical procedure.

The present technology can be implemented with any additive-manufacturing technique. When referred to as an in-situ method, the method would be executed at least partially in-situ, or adjacent patient tissue, such as one or more vertebrae.

Care, in material preparation (e.g., heating) and in some cases material deposition (e.g., location or timing of depositing) should be taken regarding the temperature to which patient tissue is exposed.

Materials that must be at higher temperatures for initial application to the in-situ site, such as metals, should be used strategically, or a different implementation of the present disclosure should be used. In a contemplated embodiment, a first layer or layers of a cooler powder or liquified material is applied before a layer of hotter liquified material, such as metal, is applied carefully over the first layer, and so not in contact with the patient. The amount of heat that would in this case still transfer, through the first layer, to the patient should be considered. In some implementations, the first material should be sufficiently cooled or solidified before the second is introduced, and in any event have sufficient insulative properties. Additionally, in some embodiments, various disclosed materials may require very high temperatures for workability and/or extrusion, and in those embodiments high temperature material may be extruded in a surrounding insulating material to prevent heat from touching the patient that functions as a shield. For example, a metallic material or a material having at least one metallic subcomponent may be extruded with a temperature resistant plastic material surrounding it that functions as a shield to protect the patient. In some embodiments, the surrounding material may also be a gel which could be displaced once one metal thread was pushed in contact with another extruded metal thread.

In some embodiments, material, such as powder, is put in place, by a dispensing element, and then materially altered, such as chemically or by heat. Some materials can be effectively melted by chemical treatment. For these embodiments, care should be taken to ensure that patient tissue is not exposed to undesirable affects, including by not limited to undesirable levels of heat.

Any of various printing material can be used, including material that are biocompatible, and materials that effect desired activity in the patient, such as materials promoting bone growth on, through, around, or adjacent the in-situ-grown or formed implant.

Regarding additive techniques, generally, any suitable printing method may be used. Suitable printing techniques allow generation of the implant in-situ, at least partially in the patient, without injuring the patient undesirably. Example additive techniques include, generally, Stereolithography (SLA), Digital Light Processing (DLP), Fused deposition Modeling (FDM), Selective Laser Sintering (SLS), Selective Laser Melting (SLM), Electronic Beam Melting (EBM), Laminated Object Manufacturing (LOM), and Binder Jetting (BJ).

An example in-situ printing technique is now described. In a powder technique, an implant is built at least partially in the patient by laying down a layer of powder in a desired configuration and location adjacent patient tissue (e.g., a patient vertebra). The powder can include a rigid thermoplastic, such as Poly(methyl methacrylate) (PMMA). This layer can be referred to as a substrate.

After the substrate is applied, a catalyst is applied to the substrate. Example catalysts include an adhesive, such as a medical-grade glue, a chemical additive, a curing material, or energy, such as heat, electron beams, radiation.

This process of printing layers is repeated in locations and amounts, selectively, to grow or form the desired implant geometry adjacent the patient tissue.

In another technique, beads are used. A dispensing component, such as a nozzle, introduces a layer of beads or particles at desired locations and amounts. The same nozzle, or another dispensing instrument, then applies a catalyst, such as an adhesive, curing additive, or energy (e.g., heat to melt) the beads, to convert the state of the beads, such as hardness, rigidity, flexibility, and shape.

In a contemplated embodiment, the nozzle includes an energy-applying element, such as a heating element.

A polymer, or other material, having a relatively low melting temperature could be used to avoid injuring tissue.

In some, fixed-end, embodiments, the system 100, including one or more dispensing components 110 and any other desired end effector/s, such as the mentioned heat applicators, are configured so that selected end effectors are fixedly attached (i.e., not readily removable/attachable) to robotics armature.

The dispensing component 110 may be referred to by a variety of terms, such as nozzle, dispenser, and applicator.

In other, modular, embodiments, the system 100, including one or more dispensing components 110, and any one or more other desired end effector, can be configured so that the end effectors can be readily attached to and removed from the robotics armature. The armature and the end effectors have mating features, for selective engaging each other, such as mating threads, tab/slot, other interlocking features, the like, or other. The features are for simplicity in the drawings considered illustrated schematically by reference numeral 111, which can still be a joint allowing relative articulation between the dispensing component 110 (and/or any other end effector) and arms or armature 112. The connection nodes 111 and arms 112 can include any number of nodes and arms, though either one or multiple are at times described by way of example herein.

Any of the system 100 components can be combined into a kit, in manufacture, or for sale or distribution.

To genericize descriptions of the various two-step-printing embodiments for simplicity herein, material or particles first laid on patient tissue are referred to as a substrate at times herein. And energy (e.g., heat), adhesive, chemicals, curing additives, etc., applied on the substrate are referred to generally as a catalyst at times herein. In contemplated embodiments, a single printing material is used, or more than one substrate material and/or more than one catalyst are used.

To allow desired post-operation motion in the patient, or to allow only a desired motion or motions, the printing material can include a non-rigid material. The material could be gummy, for instance, to form a motion-sparing, or motion-allowing, implant.

Turning now to the drawings, and more particularly to the first figure, FIG. 1 shows schematically a nozzle or dispensing component 110 of a surgical additive-manufacturing system 100 according to various embodiments of the present technology.

The component 110 is shown schematically in axial view adjacent a first patient vertebra 120. The vertebra includes a body 130 having a cortical rim 140 surrounding a cancellous end plate 150.

The dispensing component 110 can take any suitable shape or form. While the dispensing component 110 is shown schematically as a generally conical nozzle in the drawings, the component in various embodiments has other shapes, such as frustro-conical, cylindrical, tubular, prismatic, needle-like, and a non-descript shape, such as one that is ergonomic or custom-shaped to fit a patient-access. The component 110 can be rigid or flexible, of flexible and rigid in various portions.

Figure 54:
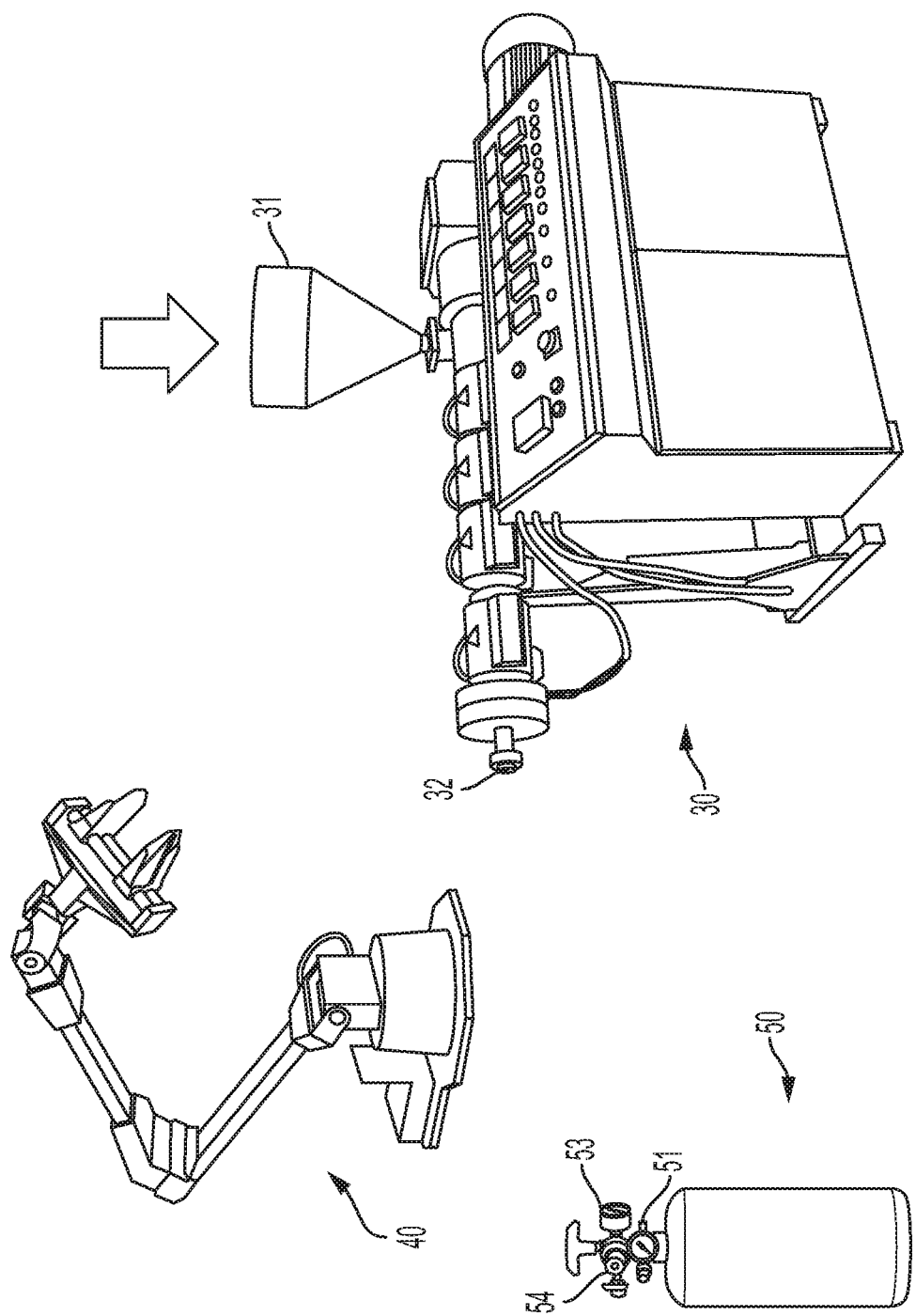
FIG. 54 shows example system hardware for use with disclosed additive-manufacturing systems.

The dispensing component 110 is connected to upstream components of the system 100 by at least one positioning or control arm 112. In various embodiments, connecting structure 111, shown schematically in FIG. 1, connects the dispensing component 110 and the control arm 112. Connecting structure 110 can also connect distinct components of the system armature 112, as shown by way of example in FIG. 10. For example, dispensing component 110 and control arm 112 may be connected to an extruder positioned upstream of dispensing component 110 and control arm 112. An example extruder 30 is shown in FIG. 54. Example extruder 30 may be a single screw extruder or a twin-screw extruder and twin-screw extruders can be co-rotating or counter rotating. Those with skill in the art will readily appreciate that the extrudate material of extruder 30 may be in fluid form and pumped to dispensing component 110 and control arm 112. For example, the extrudate material can be moved via a pump and moved through piping to dispensing component 110.

As described further below in connection with FIG. 10, the control arm 112 is actuated to position one or more dispensing components 110 as desired for depositing one or more materials. System movements are in various embodiments controlled by robotics. For example, robotic armature 40 of FIG. 54 may feed base material into extruder 30, among other things. In other embodiments, the same or substantially similar robotic armature 40 may control positioning of dispensing component 110 and/or change nozzles, orifices, dies, tips, etc. of dispensing component 110. In contemplated embodiments, any or all control-arm movement can be controlled or assisted manually, such as by a surgeon.

In a contemplated embodiment, the system 100 is configured to enable a remotely located surgeon to control aspects of the system 100. The system 100 can be configured, for instance, to allow the surgeon to, from the remote location, control operative characteristics such as position and orientation of the dispensing component 110, and material-dispensing rates. For this, the computing components 1060 of the controller 1050 are configured to communicate with actuation controls. The remote actuation controls can include those that are (a) mechanical, such as one or more handles, control sticks, the like or other, (b) automated, such as a computer to (b)(i) present images or other data from the patient-theater controller 1050 to the surgeon, and (b)(ii) transfer data indicative of surgeon movements, from the mechanical actuation controls, to the system controller 1050, for actuating the on-site system components—e.g., pump/s 1040, robotics 1030—accordingly. In at least one embodiment, pumps 1040 may be configured to supply extrudate material from extruder 30 to dispensing component 110 and control arm 112.

In various embodiments, any or all such remote componentry is a part of the system 100.

The pumps 1040 may be referred to by any of various terminology, such as a provision component, material-supply component, material supply, material-actuating system or subsystem, the like, or other.

The control arm 112 can include a single arm, or multiple arms or sub-parts. The control arm 112 can take any suitable shape or form. While the control arm 112 is shown schematically as generally cylindrical in the drawings, the component in various embodiments can have any suitable shape, and be rigid, flexible, or flexible and in various portions.

The dispensing component 110 is in various embodiments configured—size, shape, material, etc.—to enable careful delivery of printing material, such as powder, particles, or a stream or thread of material, such as a gel or other liquid or partially or semi-liquid material. Application of material in consistent layers is desired in some implementations, for example. However, in other implementations, as discussed in further detail below, it may be desirable to form inconsistent layers and/or material substrates from randomized formation of dispensing material.

Additionally, in some embodiments it may be desirable to form patient implants having both inconsistent layers and consistent layers. Accordingly, it is desirable for the dispensing component 110 to be configured to dispense precise amounts of printing material—e.g., substrate and catalyst—to specific locations.

Such features of the technology allow in-situ growing and/or formation of implants having desired strength, and precise intra-patient positioning and geometry. Proper shape, make-up, and positioning ensure that the implant will function in the patient as desired, for instance, and not impinge on areas of the patient that the implant is not intended for. The dispensing component 110 could, for instance, include at least one strain gauge or other device (not shown in detail) for registering or sensing force at the component 110. While such sensing device is not shown expressly in the drawings, the dispensing component 110 is considered to by its showing include showing the gauge, as they can be generally or fully designed to be seamless, or otherwise on and/or beneath the surface of the component 110 so as not to adversely affect component 110 movement—e.g., so as not to impinge undesirably with patient tissue or any adjacent surgical instrumentation during the surgical procedure. A computing controller 1050, described further below, can be adapted to control the nozzle partially based on this nozzle gauge output.

When the nozzle (gauge) bumps into surrounding anatomy, in dispensing component approach, positioning movement, or printing movement, the nozzle can be moved accordingly to limit or avoid the bumping. In a contemplated embodiment, the gauge is sensitive to detect objects that the nozzle should not contact, before contact. The nozzle can thus be maneuvered to avoid the contact. This can be referred to as a proximity subsystem, a proximity-avoiding subsystem, or the like. In a contemplated embodiment, the system 100 includes a circuit or switch that adjusts nozzle movement to some extent based on the gauge feedback. In this case, the computing controller 1050 can do less or none of the correction based on gauge feedback.

In one embodiment, the gauge(s) is configured and used to facilitate registering patient bone quality and adjusting the implant accordingly. For instance, if the gauge senses weak, or relatively weaker bone material adjacent the dispensing component 110, the system 100 (e.g., computing controller 1050) could apply material accordingly, such as in higher volume or in a special configuration to better address the weakness, such as by a configuration that covers more surface area at, in, or adjacent the weak area. The converse can be true. That is, less material or a special configuration can be used when strong bone is detected, such as by using less material, which can save material and time, and so cost, and be less invasive. Custom inner configuration, such as void or channeling, formed custom to adjacent patient tissue condition is mentioned below.

The dispensing component 110 can as mentioned include multiple nozzles or other implements, such as an energy-application element, to accomplish the aims of the present technology. Similarly, the dispensing component 110 may include interchangeable tips, dies, orifices and etc. for printing different types of material. In some embodiments, extrudate material ejected from dispensing component 110 may be too hot for directly printing in a patient's body. For example, dispensing component 110 may be positioned to print some types of material on a collection plate adjacent a patient and then position the material from the collection plate in a patient and/or print other materials in-situ within the patient. For example still, hot extrudate material may be printed on a collection plate and when cooled the extrudate material may be inserted into a patient and other cooler materials may be printed in-situ around the extrudate material to ensure a precise fit for a particular patients anatomy.

For implementations in which multiple materials are applied adjacent patient tissue, the dispensing component 110 can include (A) an arrangement of multiple corresponding dispensing components 110, or (B) a single dispensing component 110 by which multiple materials can be dispensed selectively. Three exemplary multi-material-dispensing arrangements are described below in connection with FIGS. 2-3, 4-5, and 6-9. Although the arrangements are described as multi-material, the one described as a catalyst can as mentioned be other than a material, such as by being an energy, such as heat, electron beam, or radiation.

In various embodiments the first material $220^1$ is delivered to the first dispensing component $110^1$ via a first transport component, such as a conduit, channel, pipe, or tube. And the second material $220^2$ is delivered to the second dispensing component $110^2$ via a second transport component. Transport components $210^1$, $210^2$ are indicated schematically in FIGS. 2-10.

Various conduits, channels, and the like are described herein, such as in connection with nozzles, or dispensing components, system arms, etc. While these various elements are in some cases described separately, such as one in the nozzle connected to one in an adjacent arm, the descriptions are meant to include embodiments in which the two adjacent elements can be a single element, including in the claims. A single channel can be used when two connecting channels, or a channel and a transport component, e.g., are described or claimed.

Figure 2:
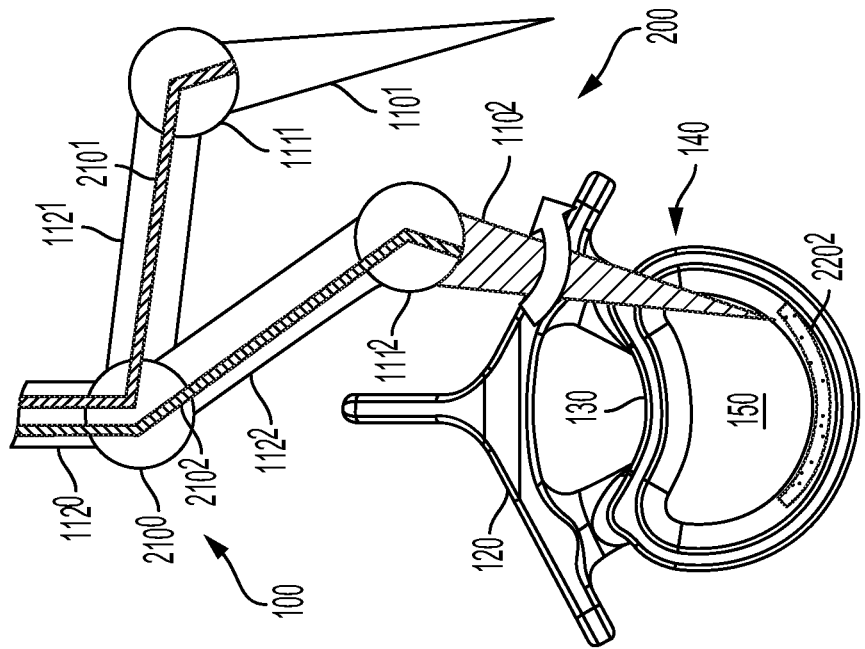
FIG. 2 is an axial view of a multi-dispensing arrangement, in a first, substrate-dispensing mode, of the additive-manufacturing system, positioned adjacent the patient vertebra according to a first exemplary embodiment of the present disclosure.

FIG. 2 is an axial view of a first exemplary multi-material-dispensing arrangement 200 having at least two dispensing components $110^1$, $110^2$. The dispensing components $110^1$, $110^2$ are connected by connecting structure 111. The connecting structure 111 can include any suitable number of connection points or nodes $111^0$, $111^1$, $111^2$. Any of the nodes $111^0$, $111^1$, $111^2$ may be joints, for instance, about which adjacent structure (nozzle and/or arms) can move relative to each other.

An entry node $111^0$, for instance allows an entry arm $112^0$ to articulate vis-à-vis first and second delivery arms $112^1$, $112^2$. Or, vice versa—i.e., allow the arms to be controlled to articulate with respect to the entry arm. A first node $111^2$ allows the first delivery arm $112^1$ to articulate with respect to the first dispensing component $110^1$, and vice versa. And a second node $111^2$ allows the second delivery arm $112^2$ to articular with respect to the second dispensing component $110^2$, and vice versa.

Components upstream of the dispensing component 110 can be referred to as positioning components. The view of FIG. 2 shows the multi-material-dispensing arrangement in a first mode, wherein the positioning components (e.g., arms $112^0$, $112^1$) are arranged so that the first dispensing element $110^1$ is positioned to dispense a first printing material 230 in-situ to the patient, and particularly in this example to, or to and adjacent, the end plate 150 of the first vertebra 120.

The first dispensing component $110^1$ receives, via at least one transport component $210^1$, a first in-situ implant-growing material $220^1$.

The dispensing component $110^1$ is maneuvered, by moving the control arms (e.g., arms $112^0$, $112^1$) and any connecting components (e.g., connectors $111^0$, $111^1$) in any suitable manner for preparing to dispense, and dispensing, the first material $220^1$ as desired. The action is indicated by example arrow in FIG. 2.

The first material $220^1$ can as referenced be referred to as a substrate material for some embodiments. The material may include PMMA or another thermoplastic, and be in power form, as mentioned. In a contemplated embodiment, the substrate material is dispensed in any of various other forms, such as liquid, semi-liquid (e.g., gel), slurry, or another form.

In a contemplated embodiment, only the first material $220^1$ is applied for the first layer, and the second and subsequent layers include the same.

Figure 3:
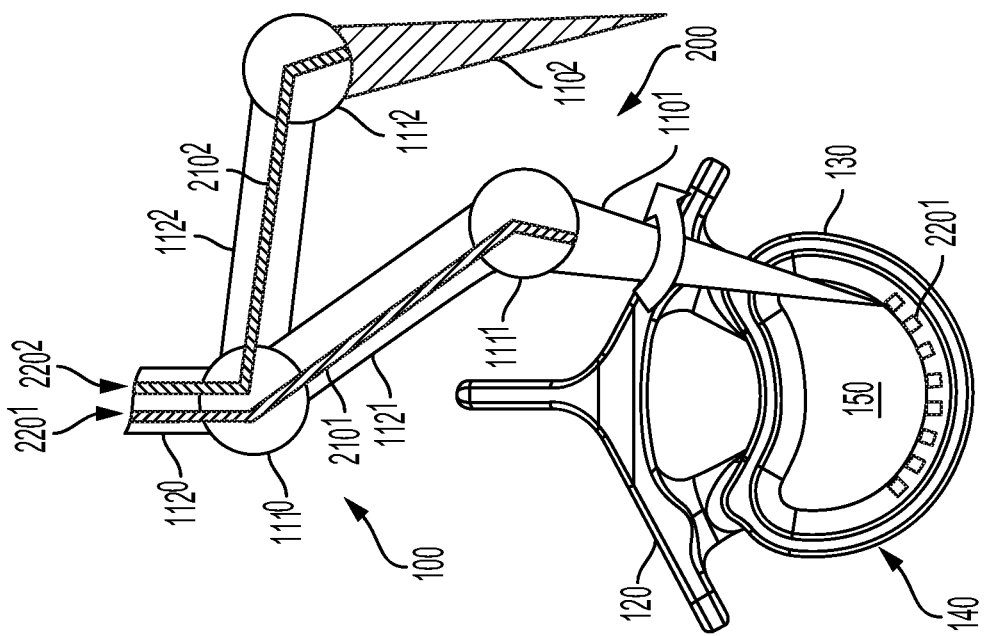
FIG. 3 is an axial view of another multi-dispensing arrangement, in a second, catalyst-dispensing mode, positioned adjacent the patient vertebra according to the first exemplary embodiment.

As mentioned, in various embodiments, after the first layer, of the first material $220^1$, is applied, a second layer of a second implant-printing or -growing material $220^2$ is applied in-situ, as shown in FIG. 3.

The second dispensing component $110^2$ is maneuvered, by moving the control arms (e.g., arms $112^0$, $112^2$) and any connecting components (e.g., connectors $111^0$, $111^2$) in any suitable manner for preparing to dispense, and dispensing, the second material $220^2$. The action is indicated by example arrow in FIG. 3.

Transitioning from using the first dispensing component to the second may in some cases require removing the first dispensing component from the patient to make room for inserting the second component. The same is true in these cases for transitioning from the second to the first dispensing component.

In a contemplated embodiments, relevant system components, including the dispensing components especially, are sized, shaped, and connected to other system components (e.g., armature 112, connector/s 111) so that the transition can be effected without removing them from the patient fully, or even without removing the dispensing components from the patient at all.

In FIG. 3, the second dispensing component $110^2$ is shown dispensing the second material $220^2$. The second material $220^2$ is applied to or on the first material $220^1$.

The second dispensing component $110^2$ receives, via at least one transport component $210^2$, the second in-situ implant-growing material $220^2$.

The system 100 including upstream source and actuation components (e.g., pumps), selectively push or pull the first and second materials $220^1$, $220^2$ through the dispensing components $110^1$, $110^2$, selectively Upstream components are described further below in connection with FIG. 10.

The second material $220^2$ can as mentioned be a catalyst. An example catalyst is an adhesive, or glue, but is not limited to these. The catalyst can also include an energy, chemical, additive, or other material causing a reaction such as curing for the first material $220^1$. The nozzle or other implement may be configured to apply heat, electrons, photons, lasers, radiation, the like or other, for instance.

Figure 4:
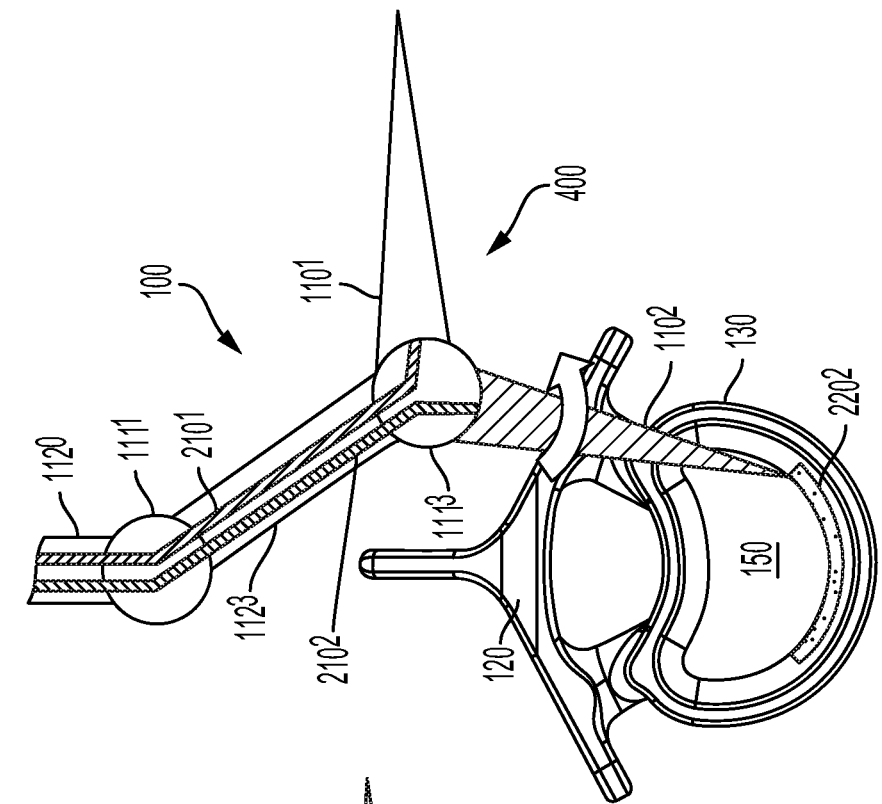
FIG. 4 is an axial view of a multi-dispensing arrangement, in a first, substrate-dispensing, mode, of the additive-manufacturing system, positioned adjacent the patient vertebra according to a second exemplary embodiment of the present disclosure.
Figure 5:
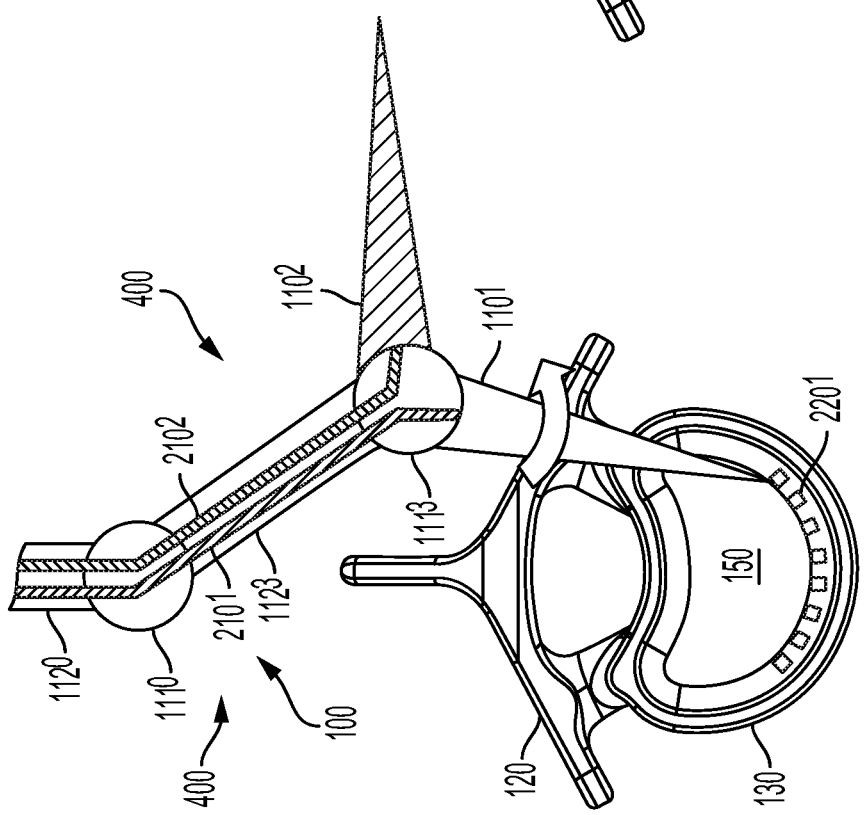
FIG. 5 is an axial view of the multi-dispensing arrangement, in a second, catalyst-dispensing, mode, positioned adjacent the patient vertebra according to the second exemplary embodiment.

FIGS. 4 and 5 show a second example multi-material-dispensing arrangement 400 for providing the substrate and catalyst $220^1$, $220^2$. The arrangement includes any number of connecting structures to which the dispensing components $110^1$, $110^2$ are connected, such as the example connecting structures shown $111^0$, $111^3$.

As in other embodiments, any number of connection structures can be used, of any size, shape, or material, including flexible and/or rigid. First and second transport components $210^1$, $210^2$ deliver the first and second materials $220^1$, $220^2$ to the dispensing components $110^1$, $110^2$.

The system 100 including upstream source and actuation components (e.g., pumps, augers, screws, conveyors, etc.), selectively push or pull the first and second materials $220^1$, $220^2$ through the dispensing components $110^1$, $110^2$. Upstream components are described further below in connection with FIG. 10.

FIGS. 6-9 show a third example multi-material-dispensing arrangement 600 for dispensing the first and second materials 230, 330. The arrangement 600 includes any number of connecting structures to which a single dispensing component $110^3$ are connected, such as the example connecting structures $111^0$, $111^4$ shown. As in the other embodiments described herein, any suitable or desired number of connection structures can be used, of any size, shape, or material, including flexible and/or rigid.

The system 100 including upstream source and actuation components (e.g., pumps), selectively push or pull the first and the second materials $220^1$, $220^2$ through the dispensing component $110^3$, selectively. Upstream components are described further below in connection with FIG. 10.

In contemplated embodiments, any of the system components—such as connecting components 111, transport components 210, or upstream source 1020 or actuation components 1030—include flow-control components (not shown in detail), such as valves, to regulate which material is fed to or through the dispensing component $110^3$, and in some cases by what amount or rate.

In various embodiments, either the first or second material $220^1$, $220^2$ is pushed through the transport components 210 at any one time, forcing that material through and out of the dispensing component $110^3$ and into the patient. As one of the materials ($210^1$ or $210^2$) is pushed through the dispensing component $110^3$, a sufficient amount of the other material ($210^2$ or $210^1$) residing in the dispensing component $110^3$ at the time, is forced out of the dispensing component until the material ($210^1$ or $210^2$) being pushed begins to be dispensed.

In a contemplated embodiment (not shown in detail), the dispensing component $110^3$ is configured so that when the system 100 changes from a first-material-dispensing mode to a second, the second material need not displace much or any of the first material. In this case, conduits, channels or tubing of the dispensing component $110^3$ extend to or adjacent a tip of the dispensing component $110^3$, keeping the material separate, or substantially separate prior to dispensation from the component $110^3$.

In a contemplated embodiment, multiple materials, such as a substrate/catalyst mix, are delivered to the patient via the dispensing component $110^3$ at the same time. The two materials can be combined in any of various locations, such as at (i) a facility at which the reservoir/s 1020 are filled, (ii) at the surgical facility prior to surgery—out-of-room, at a back table, or in the surgical theater, (iii) in a reservoir (1020 or other) in the system base 1010, (iv) downstream of the reservoirs $1020^1$, $1020^2$, such as (iv)(a) within the base 1010 or adjacent and outside of the base 1010, (iv)(b) in any of the armature 112, such as in, at, or adjacent the base 1010 or dispensing component 110, (iv)(c) in any part of the nozzle, or (iv)(d) as dispensed (e.g., at a tip of the nozzle or outside of the tip after the materials are dispensed separately from the nozzle). The reservoirs can be referred to by various terms, such as storage, supply, or source.

In another contemplated embodiment, only one suitable implant-forming material is delivered from the dispensing component 110. In this embodiment, there is not a separate application of substrate and catalyst, for instance.

Figure 6:
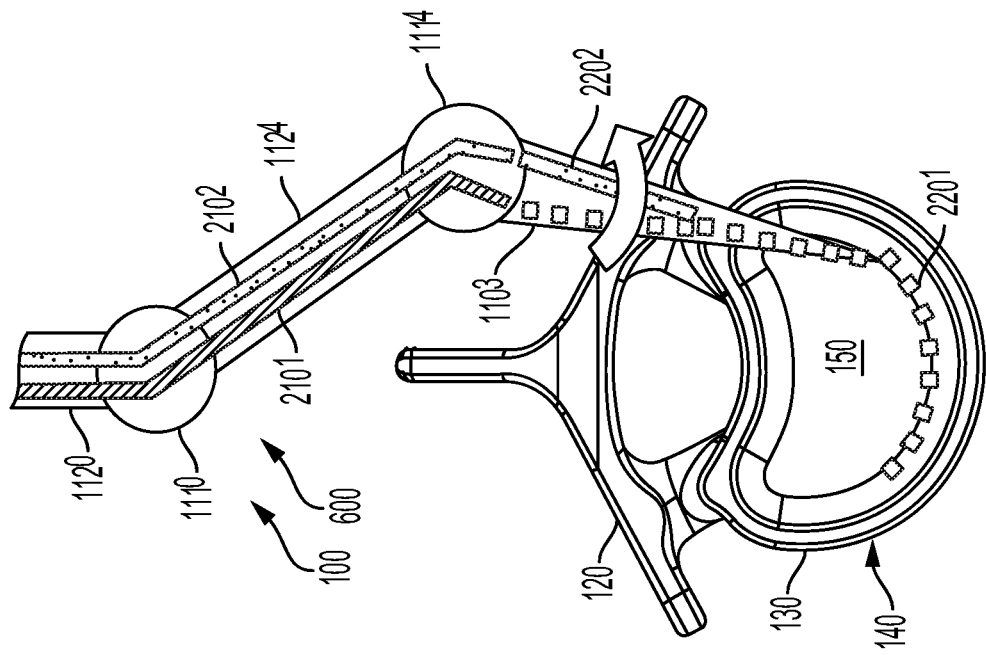
FIG. 6 is an axial view of a multi-dispensing arrangement of the additive-manufacturing system, in a first, substrate-dispensing, mode, depositing substrate material to the patient vertebra according to a third exemplary embodiment of the present disclosure.

FIGS. 6-9 also show example operation. FIG. 6 shows the first material $220^1$ being dispensed.

Figure 7:
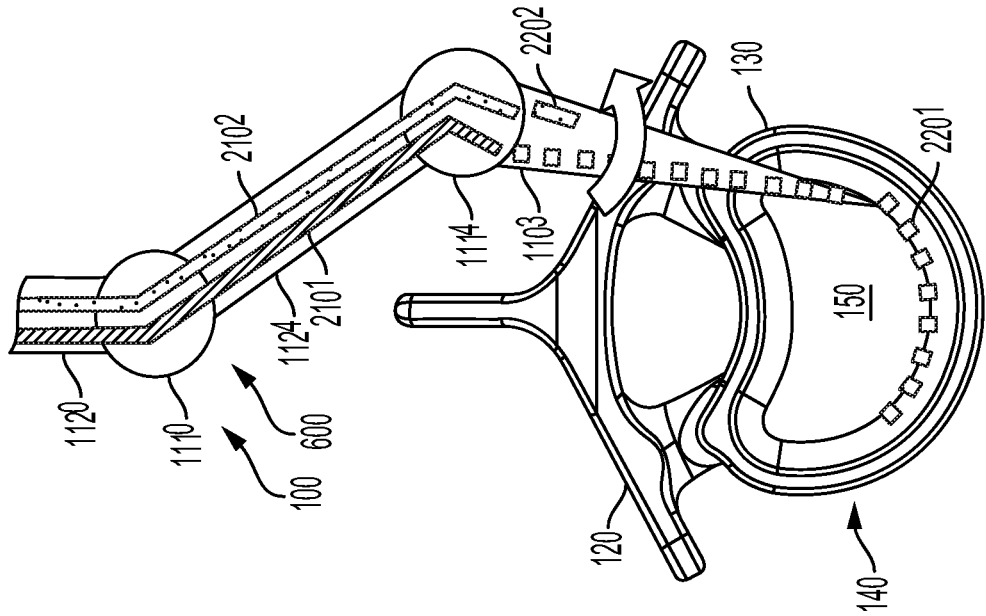
FIG. 7 is an axial view of the multi-dispensing arrangement, intra-transitional from the first mode to a second, catalyst-dispensing, mode, adjacent the patient vertebra according to the third exemplary embodiment.

FIG. 7 shows the first material $220^1$ continuing to be dispensed from the dispensing component $110^3$, as the second material $220^2$ begins to be pushed through the dispensing component $110^3$. At this point, the actuation causing or pushing the second material $220^2$, is thereby acting on the first material $220^1$ positioned still in the dispensing component $110^3$. The first material $220^1$ at this point is being forced out dispensing element $110^3$ by the force of second material $220^2$, which is being pushed through the dispensing component $110^3$. Example movement of the dispensing component $110^3$ is again indicated by arrow.

Figure 8:
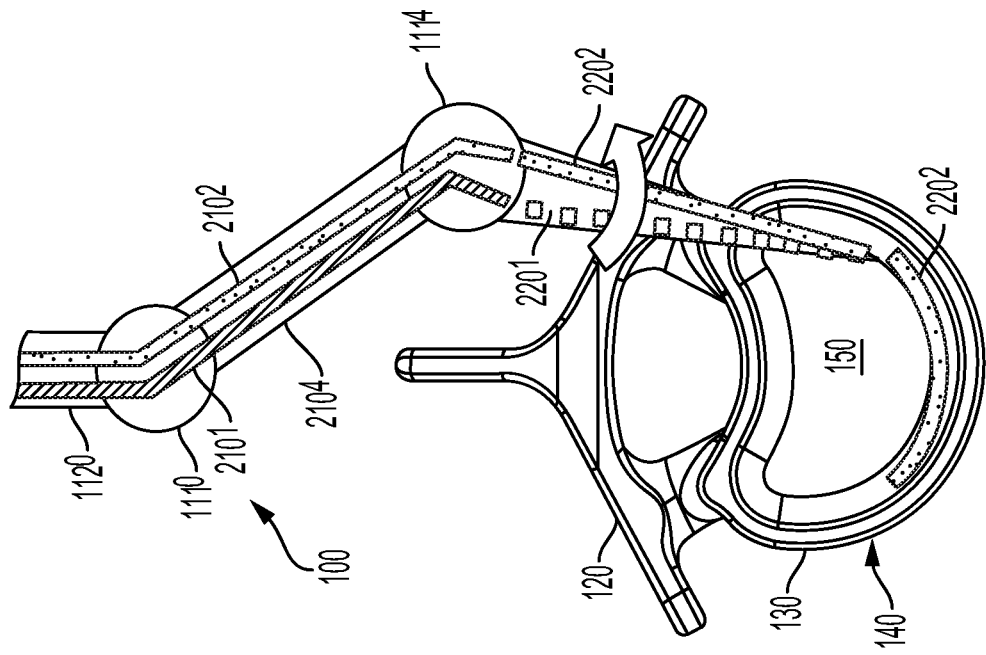
FIG. 8 is an axial view of the multi-dispensing arrangement, transitioned to in the second, catalyst-dispensing mode.

In FIG. 8, the second material $220^2$ has been pushed to the distal end or tip of the dispensing element $110^3$, so that the second material $220^2$ can now be dispense from the dispensing component $110^3$. Example movement of the dispensing component $110^3$ is again indicated by arrow.

Figure 9:
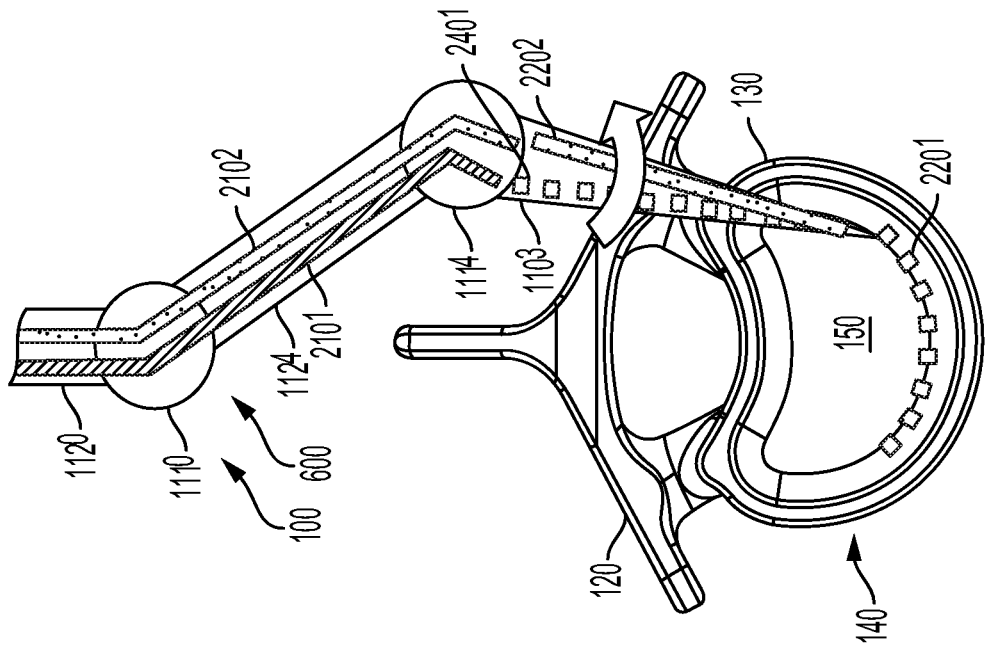
FIG. 9 is an axial view of the multi-dispensing arrangement, in the second, catalyst-dispensing mode, depositing catalyst to the patient vertebra according to the third exemplary embodiment.

In FIG. 9, the second material $220^2$ is now being dispensed from the dispensing component $110^3$.

Figure 10:
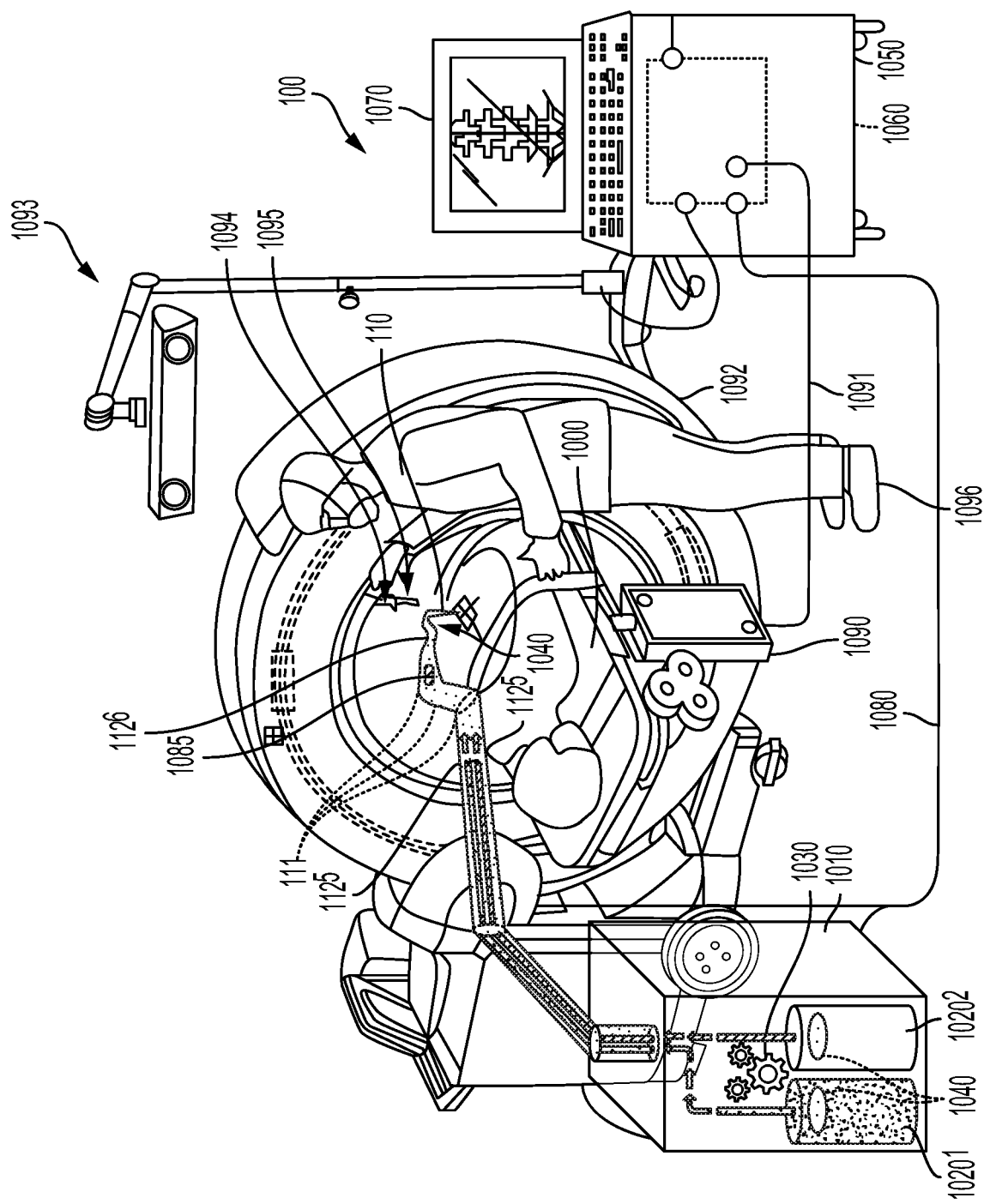
FIG. 10 is perspective view of the additive-manufacturing system positioned in theater for use with the patient.

Components of the system 100 are now described further in connection with FIG. 10.

The figure provides a perspective view of the additive-manufacturing system 100 positioned in theater for use with the patient 1000.

The dispensing component 110 extends from control arms or armature 112 and connecting components or nodes 111. The control arms 112, connecting components 111, and dispensing component 110 can be configured (numbered, sized, material, etc.) in any of various ways, including any of the ways described herein, such as in connection with FIGS. 1-9.

The structure of arms 112 may include, for instance, one or more rigid portions $112^5$ and one or more flexible portions $112^6$. The flexible and rigid locations can be positioned anywhere along the armature 112. While it is contemplated that greater dexterity will be useful closer to the end effector/s (110, etc.), flexible portions can be there, other location/s, or both.

Any armature portion may be connected by joints 111, shown schematically, to adjacent system parts, such as other arms or the dispensing component 110, as shown in FIG. 10, or a system base 1010.

The base 1010 includes at least one reservoir 1020, for holding the additive printing material 120. The reservoir 1020 is in various embodiments, whether in the base 1010, positioned adjacent or close to the end effector.

The arms 112 include or are connected to components for maneuvering the dispensing component 110 as needed for in-situ forming the additive implants of the present technology.

The control arm/s 112, connecting component/s 111, and the dispensing component/s 110 are actuated to desired positions for preparing to dispense and dispensing the implant-growing materials in-situ, to select areas adjacent tissue of the patient 1000. System movements are in various embodiments controlled by suitable robotics.

Robotics can include any suitable actuation and control componentry, is indicated schematically by reference numeral 1030.

In various embodiments, the base 1010 includes some or all of the robotics components, including controlling and actuating subsystems (not shown in detail).

The robotics equipment 1030 includes, is connected to, or is a part of the arms 112, for effecting desired arm movement, such as according to a pre-established surgical plan. The plan may be adjusted real-time based on sensing data, from a sensor with the dispensing component 110 or external to the patient. The sensing data may indicate that patient tissue is shaped or becoming shaped or positioned in a manner that was not anticipated by the plan, for instance. And a system controller, described further below, can be configured (e.g., coded) to thus make necessary adjustments to the plan, with or without surgeon or surgical staff intervention.

The robotics equipment 1030 can include or be connected to one or more pumps, indicated schematically by reference numeral 1040. The pumps 1040 are configured and positioned to push printing material $220^1$, $220^2$ selectively from the reservoirs $1020^1$, $1020^2$.

In a contemplated embodiment, the pump/s 1040, or additional pumps, are positioned upstream of the base 1010, such as in the robotics armatures 112, or in, at, or adjacent the dispensing component 110. If the upstream pump/s are provided in addition to one or more downstream pumps, the upstream pump/s can be referred to as booster pumps, amplifying pumps, or the like.

The robotics equipment 1030 includes or is connected to control componentry, such as computing equipment, indicated by reference numeral 1050 in FIG. 0.10.

Data communication connection between the controller 1050 and the robotics equipment 1030 and pumps 1040 can be wireless or wired, and is indicated by numeral 1080.

Reference numeral 1060 indicates components of the controller 1050. These can include any suitable automation, computing, or control componentry. Example components include (i) a communications bus, (i) a memory component storing computer-readable data, or instructions, such an in-situ-forming plan, which may be or include computer-aided-design (CAD) data, and (iii) a processor for receiving and executing the stored data to control and/or receive data from system components, such as the pump 1040 and robotics equipment 1030.

The controller 1050 in various implementations controls and/or receives data from one or more pieces of scanning equipment, any of which is considered a part of the system in some embodiments.

The memory component, of the computing components 1060 of the controller 1050, can be referred to by any of a variety of terms, such as a computer-readable medium, computer-readable subsystem, memory, storage, or storage component, and is in various embodiments non-transitory. The memory component may include any format or componentry, such as random-access memory (RAM) and read-only memory (ROM).

The controller 1050 can also include or be configured for ready connection to at least one interface for communication into and/or out of the controller 1050. The interface is indicated schematically by reference numeral 1070. The interface 1070 can include any available interface equipment, such as visual or audio input/output equipment, keyboard, etc. Visual input- and/or -output equipment can include a touch-sensitive display, such as a display screen showing an image of a portion of the spine of the patient 1000, rendered from sensing data, such as from sensing equipment 1093. In various embodiments, the sensing equipment is a part of or connected to the system 100. Visual components can include wearable visual components, such as one or more AR or VR components, such as at least one helmet, goggle or glasses, or the like, and are considered shown in the figures by the illustrated indication of i/o equipment 1070. The sensing equipment, whether part of the AR/BR component, or the illustrated remote sensors 1093, can sense surgeon movement. The system can also include one or more cameras, or visual sensing devices, such as an on-dispensing-component, on-robotic arm, camera, or other selectively positioned camera/s. The visualization equipment and such visual-sensing equipment can be connected to the controller 1050 such that (i) relevant visuals are provided to the surgeon and (ii) surgeon movements, e.g., hand movements, are translated, via the robotics, into movements or other functions of the dispensing component 110. In a contemplated embodiment, the controller 1050 can have a limited or no role in any of these functions—the wearable visual component can be connected wirelessly to the source visual sensor/s, for instance. As an example other control that the surgeon can influence in this way, outside of dispensing-component movement, a surgeon moving or squeezing her fingers together, such as toward making a fist, can to the extent of squeezing, affect amount and/or rate of dispensing of printing material 220.

The controller 1050 is communicatively connected with various apparatus by wire or wirelessly, all indicated schematically by reference numeral 1080. Example apparatus include controlled components, such as the pump/s 1040, robotics components 1030, and any other apparatus that communicates with the controller 1050, such as a scanning or imaging machine 1092. The imaging machine 1092 may include a separate computing system, as shown at left of the view of FIG. 10.

In contemplated embodiments, any or all actuations, including those for material pumping (1020), or armature 112 or dispensing component 110 positioning, can be effected or assisted manually, by surgical staff.

For some of the embodiments in which the dispensing component 110 is maneuvered manually, it is contemplated that the system 100 could include an actuator, such as a trigger, or button, or depressible portion of the dispensing component 110 or arm 112. The actuator, indicated schematically by reference numeral 1085 in FIG. 10, can also include or be connected to valves or other structure that can affect material flow as desired.

The term provision component can be used generally for any system components affecting the provision of printing material or energy to the dispensing component/s 1050 and in-situ location, such as the pumps 1040, an actuator 1085 causing material flow, a controllable valve affecting flow, or other suitable provisioning element or apparatus.

In various embodiments, the controller 1050 may be configured to control the pumps 1040, extruder 30, robotic armature 40, and/or air source 50 as will be explained in further detail below in conjunction with FIG. 54. Wherever the pumps 1040 are located (in the base, or downstream thereof, e.g.), and whether the dispensing component 110 is controlled by robotics and/or manually by a surgeon, software (part of the automation components 1060) of the controller component 1050 can be configured to actuate pumping—i.e., control printing-material feed timing and/or rate, for instance—based on any of various factors.

Example factors include (a) the stage, phase, or time of a pre-established plan that the procedure is in, which plan may be programmed in software of the system controller 1050, such programming including a computer-aided-design (CAD) file, (b) position or orientation of the dispensing component 110, and (c) movement of the dispensing component 110.

Regarding the latter factor (c), it may be advantageous, for more-consistent, more-evenly, depositing, for instance, to dispense less printing material (lower-rate provision), or less material per time (rate), when the dispensing component 110 is being moved more slowly (robotically or manually), and more material (higher-rate provision) when the dispensing component 110 is moved more quickly.

For embodiments in which material feed rate is based on nozzle movement or position, the system 100 could include position- or motion-sensing componentry providing to the controller 1050 nozzle position or motion-indicating data. Data could also indicate arm 112 position or orientation, from sensors in the arms, connected to the arms, or remote sensors (see e.g., sensor 1093) in the room sensing navigation components (see e.g., components 1094). The remote features 1093, 1094 are described further below.

Sensing componentry that is in or connected to the armature or dispensing component 110 can also be considered indicated schematically by reference numeral 1085 for simplicity of the drawings.

The controller 1050, and more particularly the memory of the controller components 1060, can store a wide variety of data. Example datum include programs, patient identification or anatomy data, in-situ printing plans, machine-learning or artificial-intelligence code, or actual surgical procedure information, such as steps performed, results thereof, sensed features of the patient or printing process, etc. Any of the data, such as the surgical plan, can be partially or fully surgeon-created.

The system 100 is configured in various embodiments such that the data can be accessed, or generated, by a user, or another controller or computing system, via the controller interface 1070 or communication connection(s) 1080. Data can be transmitted from or to the controller 1050 by any suitable hardware or method, such as by wire, Bluetooth, Wi-Fi, portable drive, email, or any available communication technology.

In some embodiments, the controller 1050, by the controller components 1060, controls patient-positioning equipment, such as a surgical-table control system 1090. The controller 1050 is connected to the table control system 1090 by wire or wirelessly, both indicated by reference numeral 1091.

In a contemplated embodiment, the table control system 1090 is adjusted at least one time during the surgery, after a first stage of the in-situ printing, for improving positioning, spacing, dynamics, or the like, for a subsequent phase of the in-situ printing.

In various embodiments, the patient 1000 can be positioned at an angle with respect to horizontal, such as by tiling the table via the table control system 1090. Doing so may have a benefit of enabling printing on patient tissue (e.g., vertebral body end plate 150) while the tissue is positioned or orientated in an advantageous manner. Example advantageous manners can include, for instance, manners that (a) better allow the dispensing component 110 to fit into or be moved within the patient, (b) control, harness, or take advantage of material characteristics, such as to migrate or run when deposited on an angled surface (e.g., some powder or liquid substrates, before a catalyst is applied), and (c) avoid or harness gravity.

As referenced above, the control componentry 1050 in contemplated embodiments controls and/or receives information from sensing equipment to facilitate the in-situ implant printing. Example sensing equipment includes the scanning or imaging machine 1092. The scanning machine 1092 is positioned to obtain images of the patient in preparation for and/or during the in-situ-printing (ISP) procedure.

Pre-procedure scanning can include or be part of a registration process and surgical plan. The registration, surgical planning, and registration and plan storage can be performed by the controller 1050 and/or by other computing devices.

The surgical plan can be partially or fully surgeon-created.

Scanning data can be used by the controller 1050 to recognize and record desired patient position for the surgery, including position of patient anatomy, including injured or compromised areas. Repeated scannings can be performed—one or more prior to the surgery, typically on a day prior to the surgery, and again to prepare for the surgery, day-off, ensuring that the patient is positioned as desired. The registration can include registration data for the patient in multiple positions for the surgical plan, as mentioned above.

As mentioned, the system 100 can include or be used with navigation sensing system 1093. The navigation sensing system 1093 senses targets 1094 affixed to a navigation instrument 1095, such as a navigated guide, surgical drill, or bone-screw driver.

In various embodiments, any of the nav components 1093, 1094, 1095 are part of the system 100.

Navigation equipment 1095 can be maneuvered for its purpose by the surgeon 1096 and/or by the controller componentry 1050 and robotics 1030, based on data received from the navigation sensing system 1093. Regarding robotic control, the nav instrument 1095 could be an end effector, connected to the armature 112, of the system 100, for example. Navigation data is used by the controller 1050 or surgeon for positioning the navigation equipment 1095 precisely as needed to execute a surgical maneuver.

The maneuver facilitated can include positioning the dispensing component 110 for printing. The dispensing component 110 or distal armature 112 can include the navigation targets 1094 for this, for instance.

Whether navigated, embodiments in which robotics equipment is used for surgical functions, outside of printing functions, can include any related surgical procedures. For spinal surgeries, for instance, the system 100 can include or be connected to instruments for distraction or correction. By distraction, the robotics equipment or surgeon would apply appropriate forces to manipulate vertebral bodies as desired or needed, such as to size or shape the intervertebral space (reference, e.g., the space indicated by 3610 in FIG. 36), or to orient one or more vertebra of the spine otherwise as desired. The distraction using robotics could be used specifically to gain access to the disc space, or for correction after the implant is printed. The robotics could, for instance, move the vertebral bodies such that the printed implant (e.g., cage) doesn't contact one or both of two adjacent endplates initially, and then move the vertebral body/ies to contact cage. As another example, the implant could be printed with protrusions, such as spikes, such that moving the adjacent vertebral body/ies to contact the implant would drive the protrusions into the vertebral body/ies, promoting implant securement in place. Such 'positive' (versus 'negative', like holes, channels, etc.) features are describe further below.

In various embodiments, the surgeon or robotics 1030 moves or otherwise adjusts the implant after it is formed.

Some example procedures will now be described further.

Figure 11:
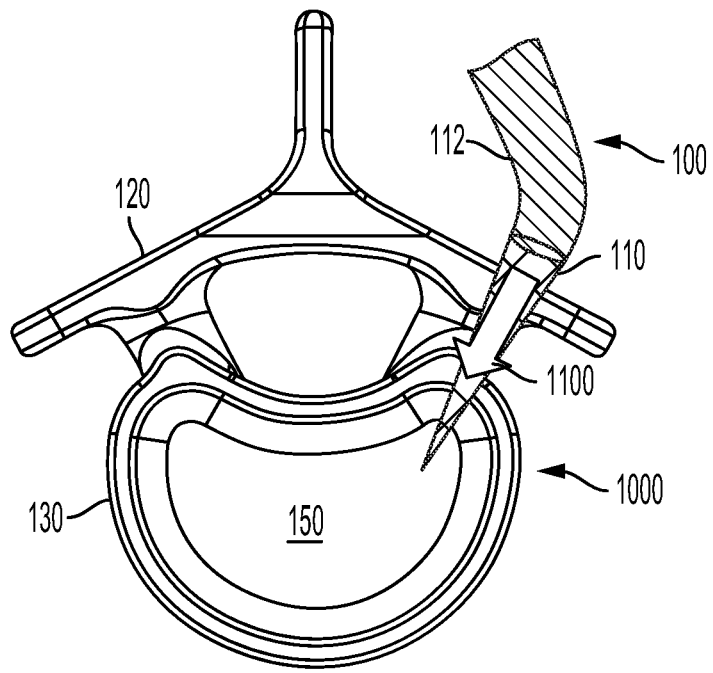
FIG. 11 is the axial view of FIG. 1 with the dispensing component of the additive-manufacturing system being moved toward an in-situ position of the patient.

FIG. 11 is the axial view of FIG. 1 with the dispensing component 110 of the additive-manufacturing system 100 being moved toward a desired or pre-planned in-situ printing position of the patient 1000 adjacent the patient vertebral body 130. Dispensing-component movement, shown schematically by arrow 1100, is in various embodiments controlled by the controller 1050 and the robotics equipment 1030.

The robust fixation between the implant being grown or formed and patient tissue 120, 122, enabled by printing a patient-shaped implant in-situ, may be enhanced by preparing printing features into or on the implant and/or preparing the tissue in a suitable manner, such as by roughening or grooving.

The implant features promoting implant-to-tissue adhesion and/or connection can include surface roughening, surface shaping (e.g., teeth, grooves, channels), and surface coating, or physical features that penetrate patient tissues, such as bony surfaces, e.g., vertebral bodies, or features for attaching post-printing devices such as eyelets for inserting screws. The surface features, whether a level of roughness, smoothness, and/or other features, can be configured to promote or control bone growth on, at, or adjacent the implant, or protect adjacent anatomy. Generally, a rougher surface promotes bone growth, while a smoother surface limits affects on adjacent anatomy.

The implant of this embodiment, or any embodiment herein, can also be formed to have geometry promoting any of strength, weight, and bone growth. Regarding the latter, the implant can be formed to have at least one hole, recess, or hollow, partially or fully through the implant, for instance, to promote bone growth into or through the implant.

Figure 12:
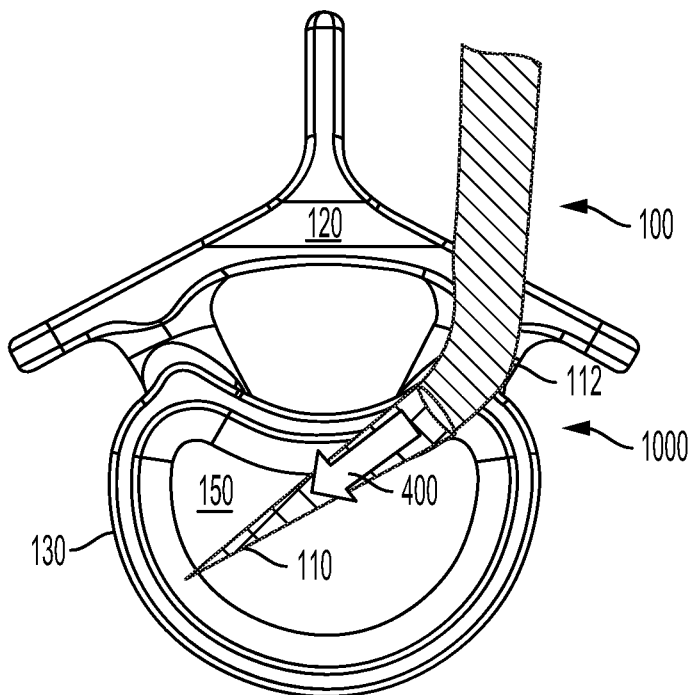
FIG. 12 is the axial view of FIG. 1 with the dispensing component moved to an example in-situ position of the patient according to a first general embodiment of the present technology.

FIG. 12 shows the dispensing component 110 moved to an example in-situ position of the patient 1000 according to a first general embodiment of the present technology. The movement is indicated by arrow 400.

Embodiments are referred to as general because they are agnostic to which particular dispensing-component arrangement is used, such the arrangements 200, 400, 600 of FIGS. 2-9.

Figure 13:
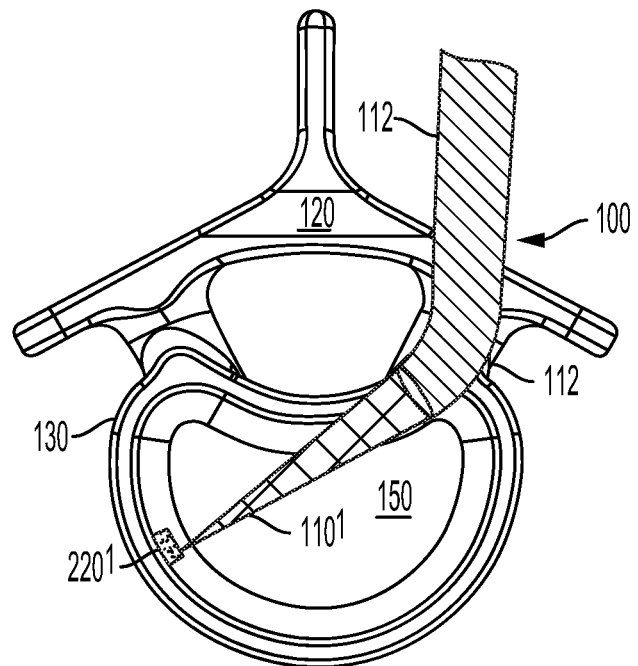
FIG. 13 shows commencement of in-situ formation of a first interbody implant, by the dispensing component, dispensing a first row of a first, substrate, material, to the in-situ position of the patient according to the first general embodiment of the present technology.

FIG. 13 shows commencement of in-situ formation of a first interbody implant, by the dispensing component 110, dispensing a first row of a first, substrate material $220^1$, to the in-situ position of the patient 1000.

The dispensing component 110 can, as described include any of those shown and described herein. The dispenser 110, applying the first material $220^1$, can be, for instance, any of the first-material dispensing nozzles $110^1$, $110^3$ described with the arrangements 200, 400, 600.

Figure 14:
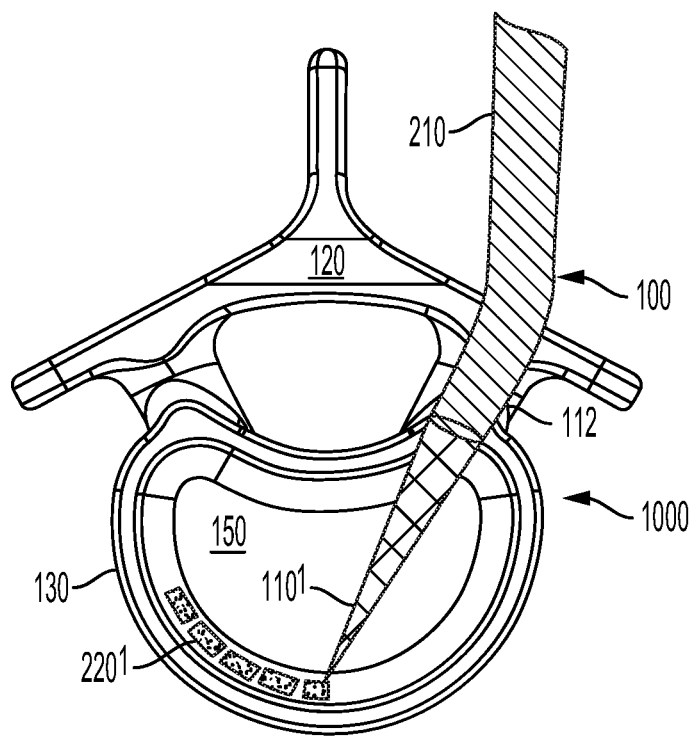
FIG. 14 shows the dispensing component continuing to dispense the substrate material to the in-situ position of the patient according to the first general embodiment of the present technology.

FIG. 14 shows the dispensing component 110 continuing to dispense the substrate material $110^1$ to the in-situ position of the patient 1000.

Figure 15:
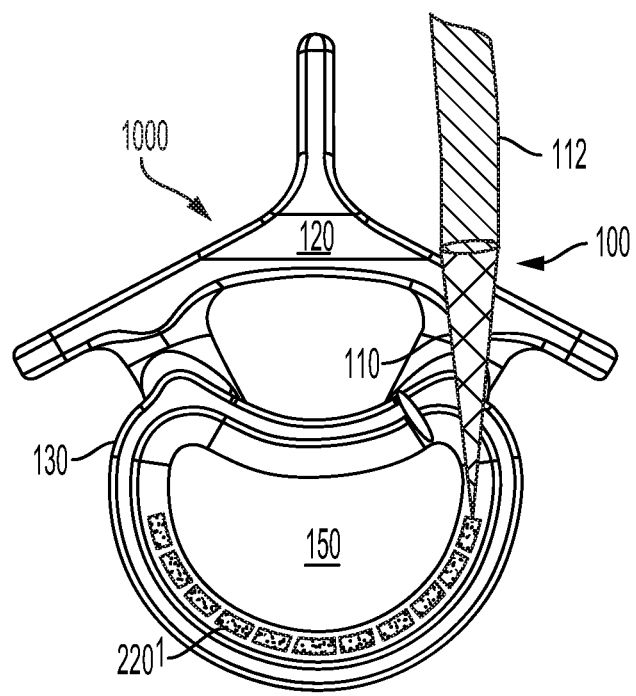
FIG. 15 shows the dispensing component completing depositing of a first row of substrate material at the in-situ position of the patient according to the first general embodiment of the present technology.

FIG. 15 shows the dispensing component 110 completing dispensing of a first row of substrate material $220^1$ at the in-situ position of the patient 1000.

Figure 16:
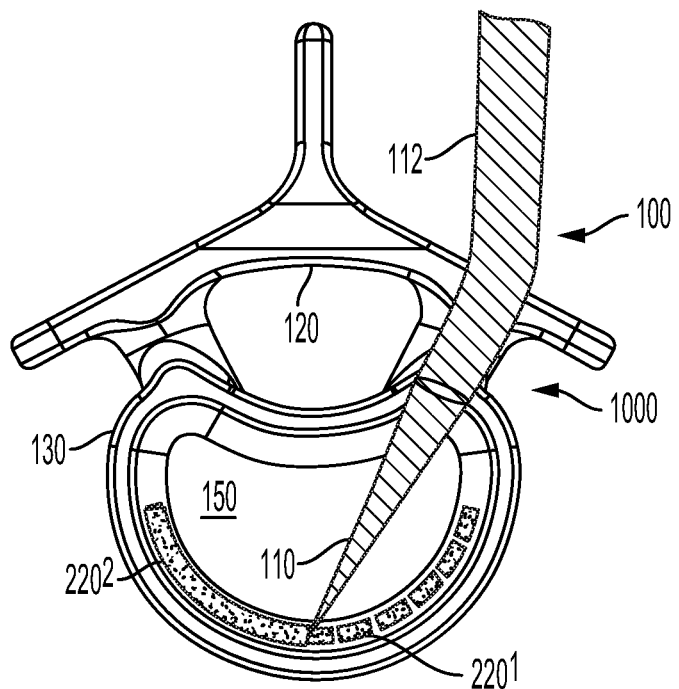
FIG. 16 shows the example dispensing component dispensing catalyst, over or to the first-row substrate material at the in-situ position of the patient according to the first general embodiment of the present technology.

FIG. 16 shows the dispensing component 110 dispensing a catalyst $220^2$ over the first-row substrate material $220^1$ at the in-situ position of the patient 1000. The catalyst can as mentioned include any of various applications, such as adhesive, curing material, or energy such as heat, electron beam, or radiation.

The dispensing component 110 can again here include any of those shown and described herein. In the view of FIG. 16, the dispenser 110, applying the second material $220^2$ can be, for instance, any of the second-material dispensing nozzles $110^2$, $110^3$ described with the arrangements 200, 400, 600.

Figure 17:
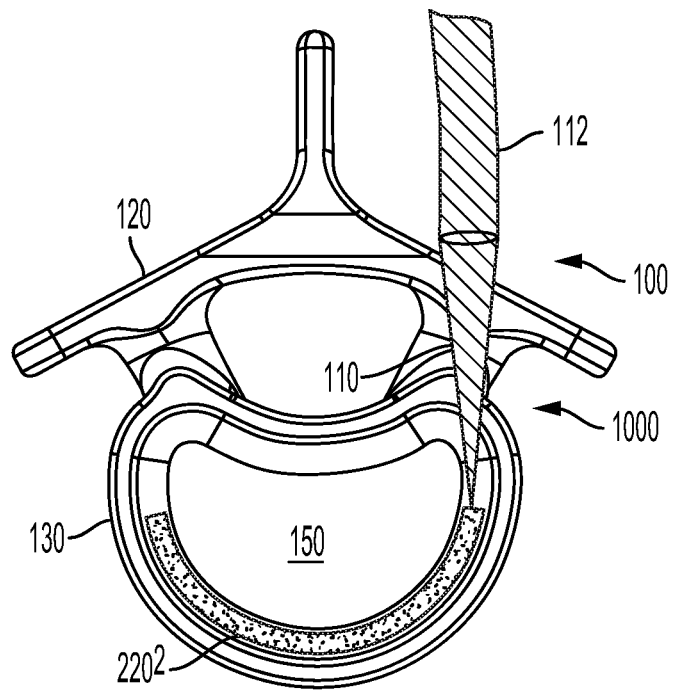
FIG. 17 shows the dispensing component completing the first row of catalyst over the first-row substrate at the in-situ position of the patient according to the first general embodiment of the present technology.

FIG. 17 shows the dispensing component 110 completing the first row of catalyst $220^2$ over the first-row substrate $220^1$ at the in-situ position of the patient 1000.

Figure 18:
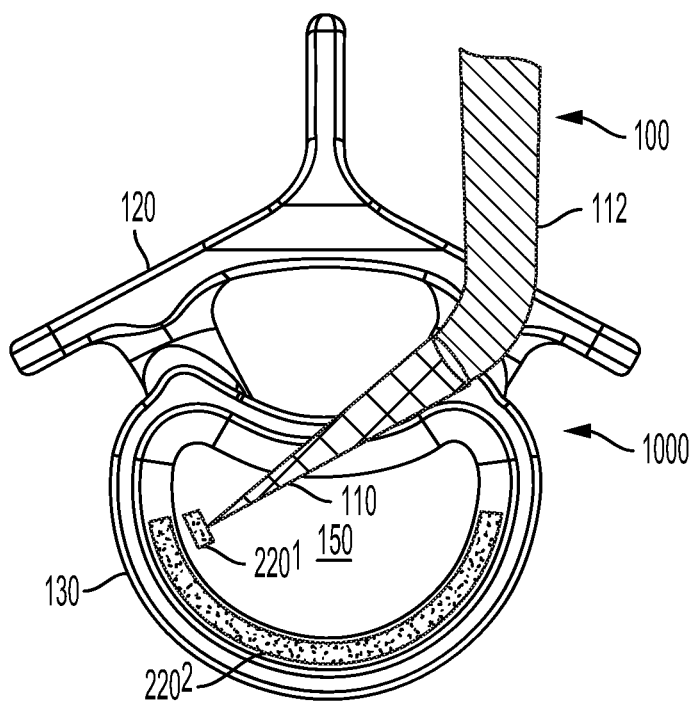
FIG. 18 shows the dispensing component dispensing a subsequent row of substrate material to the in-situ position of the patient according to the first general embodiment of the present technology.

FIG. 18 shows the dispensing component 110 dispensing a subsequent row of substrate material $220^1$ to the in-situ position of the patient.

FIG. 19 shows the dispensing component 110 completing dispensing of the subsequent row of substrate $220^1$ at the in-situ position of the patient 1000.

FIG. 20 shows the dispensing component 110 dispensing catalyst $220^2$ over the subsequent-row substrate material $220^1$ at the in-situ position.

FIG. 21 shows an example completed first-layer 2100 of the additive in-situ implant.

In various embodiments, the printing does not have to be strictly layer-by-layer. A first layer can be started, then a second, then a third, then addition to the first or second before starting the fourth, as an example.

In various embodiments components can be moved, by the system 100 (e.g., dispensing component 110 or another end effector) or surgeon, after being formed, to fit or better fit in a desired intra-patient position.

FIG. 22 shows the dispensing component 110 beginning a subsequent layer of substrate material $220^1$ over the first completed layer 2100 at the in-situ position of the patient 1000.

The process is continued, layer by layer, or portion by portion, to complete the in-situ-printed spinal implant. The particular sort of implant can be referred to as an in-situ-grown or formed interbody or cage.

Figure 23:
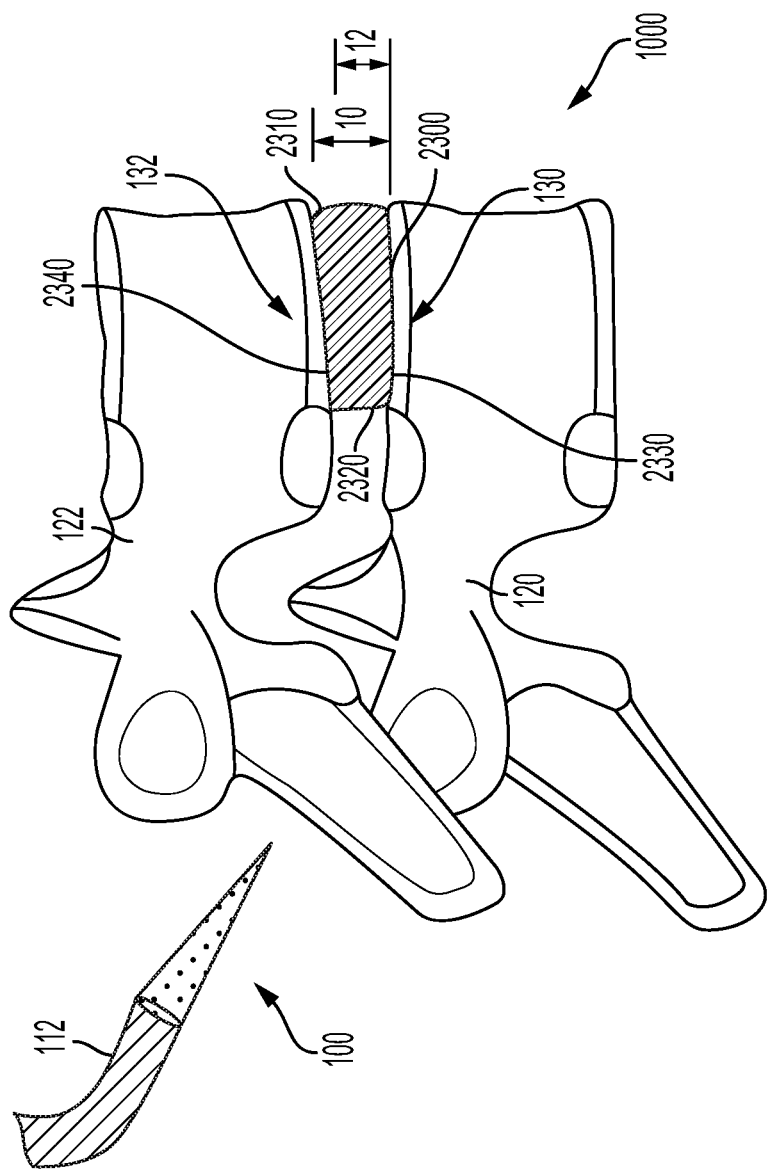
FIG. 23 is a lateral view of the first additive in-situ implant formed in-situ adjacent the first patient vertebra and a second, adjacent, vertebra.

FIG. 23 is a lateral view of the first in-situ-grown or formed implant 2300 formed adjacent the first patient vertebra 120 and a second, adjacent, vertebra 122.

The implant 2300 is grown or formed in-situ to extend from an anterior, end 2310 to a posterior, end 2320, and from an inferior end, or base, 2330 to a superior end, or top 2340. The implant 2300 can be printed in-situ to have any desired configuration (e.g., size, geometry), to accomplish needed bodily adjustment, or tissue-position maintenance, during and after the procedure. In the example shown, the in-situ-grown or formed implant 2300 is created to have a height that tapers generally from a maximum anterior height 10 to a minimum posterior height 12.

Figure 36:
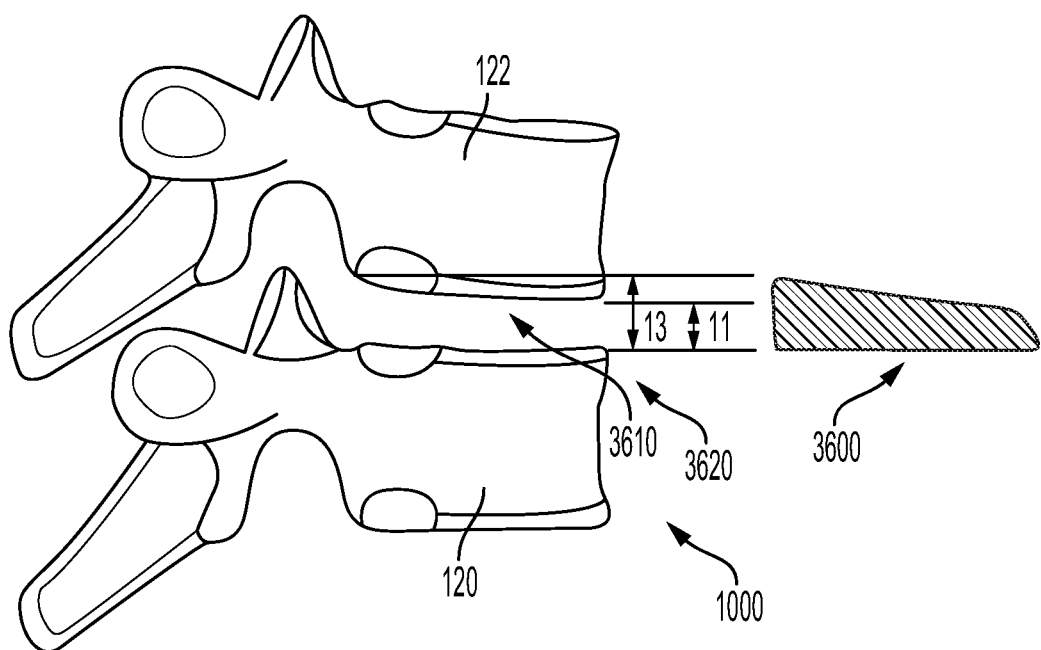
FIG. 36 is a side view of two adjacent patient vertebrae spaced such that an illustrated interbody implant cannot be readily passed to a desired inter-vertebral position.

The height is in various embodiments tapered in the other direction (down from a maximum posterior end), as shown in FIG. 23, not consistently tapered (e.g., tapered in one or more portions, but not across the entirety, and perhaps not in the same directly), or not tapered. Counter tapering (down from a maximum posterior) can be useful, for instance, when the patient anatomy or surgical strategy calls for a larger posterior portion, as shown needed in the case of FIG. 36. FIG. 36 is described further below.

In the present embodiment, and for any of the embodiments provided, geometry of the in-situ-grown or formed implant 2300 could have any features beneficial for encouraging bone growth on, through, around, or adjacent the implant. In contemplated embodiments, the material may include or be coated with any beneficial material. Example materials include medicinal material, antibiotic material, and bacteria- or virus-resistant or -fighting materials. Materials could be introduced by the dispensing component 110, as discussed above, or another nozzle or dispensing component.

Implant 2300 geometry may be shaped to avoid any remaining bony structures present, such as may occur in a partial osteotomy procedure. In a contemplated embodiment, the printing material includes material configured to affect patient tissue.

Implant 2300 geometry may include features that facilitate surgery, such as those that can be used as drill guides or for anatomical holding. As an example of the latter (anatomical holding), the implant 2300 could be shaped to (a) hold back or move a dura of the patient 1000, (b) shield exiting nerve roots, or (c) block any blood vessel from being injured in surgery. (dura, roots, and vessels not shown in detail) The facilitating features can be temporary, by being removable after they have served their purpose, which can be prior to an end of the printing steps or any time before an end of the procedure.

In various embodiments, the system controller 1050 controls other system 100 components to form an implant having geometry corresponding with patient anatomy. The controller 1050 can do this by, for instance, controlling the robotics 1030 and pumps 1040 to form implant pockets or recesses in the implant being formed. Such features can align with, or be offset from, actual patient anatomy, for instance. This may help avoid or limit unwanted implant/anatomy contact. As another potential benefit, printing the implant to have such anatomy-related, or anatomy-customized, features may allow formation of preferred wall thickness or other sizing for the implant, while still allowing the implant to fit in the desired location within the patient 1000.

Figure 24:
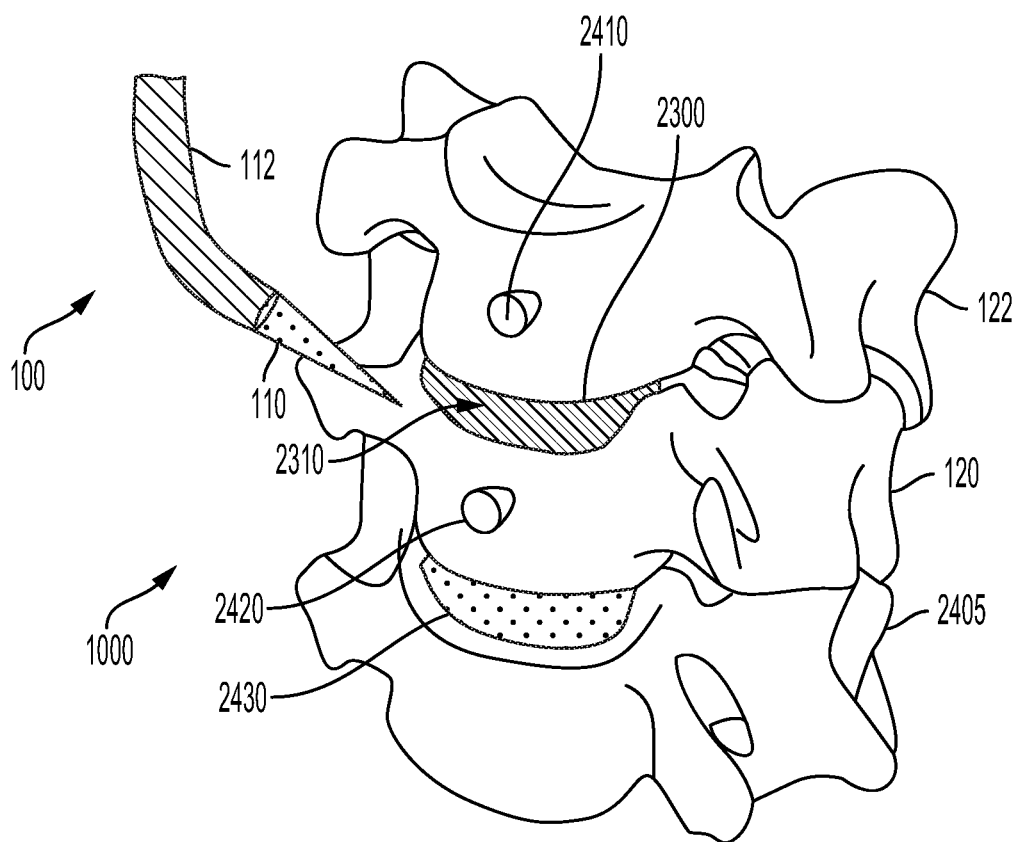
FIG. 24 is a perspective view showing the dispensing component in another in-situ position according to a second general embodiment of the present technology, which can be effected following execution of the first general embodiment.

FIG. 24 is a perspective view showing the dispensing component 110 in another in-situ position adjacent the vertebrae 120, 122 of the patient 1000 according to a second general embodiment. A native intervertebral disc of the patient, between the first vertebra 120 and a further inferior vertebra 2430, is indicated by reference numeral 2430.

The second general embodiment can include, or be effected following execution of, performance of the steps under the first general embodiment described above in connection with FIGS. 11-23. The dispensing component 110 can print the interbody 2300 from a posterior approach and/or an anterior approach. The component 110 can be moved from a completing step of dispensing from a posterior approach, to an anterior approach to commence or continue printing the plate component 2500 (FIGS. 25-28), for instance.

In a contemplated embodiment, the interbody between the patient vertebrae 120, 122 is not in-situ printed or not fully in-situ printed (see, e.g., the embodiment described below in connection with FIGS. 41-44). The interbody there can be pre-manufactured, at a manufacturing facility, for instance.

It should be appreciated that, as with the other in-situ-grown or formed implants described herein, the resulting implant 2300 of this embodiment is highly customized to the patient anatomy, being formed adjacent and on or at patient tissue, including but not limited to the vertebrae 120, 122 in primary examples.

The implant 2300 of this embodiment, or any embodiment herein, can also include interface features to promote printing-material-to-tissue adhesion and/or connection, and/or strengthen the implant. Example interface features include surface roughening, surface shaping (e.g., teeth), and surface coating, or physical features that penetrate patient tissues, such as bony surfaces, e.g., vertebral bodies, or features for attaching post-printing devices such as eyelets for inserting screws.

FIG. 24 shows an implant in place, such as the in-situ-grown or formed interbody of FIG. 23. The figure also shows anchoring components 2410, 2420 affixed to respective anterior faces of the superior and anterior vertebrae 122, 120 of the patient 1000. An example anchoring component, or anchor, is a bone screw. In some embodiments, the anchors include any type of bone screw used conventionally in spinal surgeries. In a contemplated embodiment, the anchor 2410, 2420 is customized to facilitate the implant growing or implant qualities (e.g., shape, strength).

In various embodiments, the anchors 2410, 2420 are printed in place. The technique includes pre-forming bores in the anterior face of the vertebrae 122, 120, and growing the anchors therein, and therefrom.

In one embodiment, the anchors are mechanically driven or forced (i.e., by force, twisting, or the like, versus printing) into the bone, such as by use of a driver instrument. The anchor can be a metal screw, for instance. The anchors can be driven or forced by system components (not shown in detail), such as an anchor driver connected to an end of the robotics armature, with, or in a modular embodiment, as a driver end effector selectively instead of the dispensing component being in this case a readily removable end effector.

It is contemplated that boring equipment (not shown in detail) for this purpose can be part of the system 100. One or more boring end effectors can be attached to the robotics armature, such as an additional effector with the nozzles in the views of FIGS. 2-9. Or the boring end effector can be connected to the armature selectively, as can in some embodiments the dispensing componentry, as described above. The boring equipment can be part of the kits mentioned above. For purposes of illustration, the boring equipment, whether modular, is considered illustrated by the end effector 110 of FIG. 24.

Figure 25:
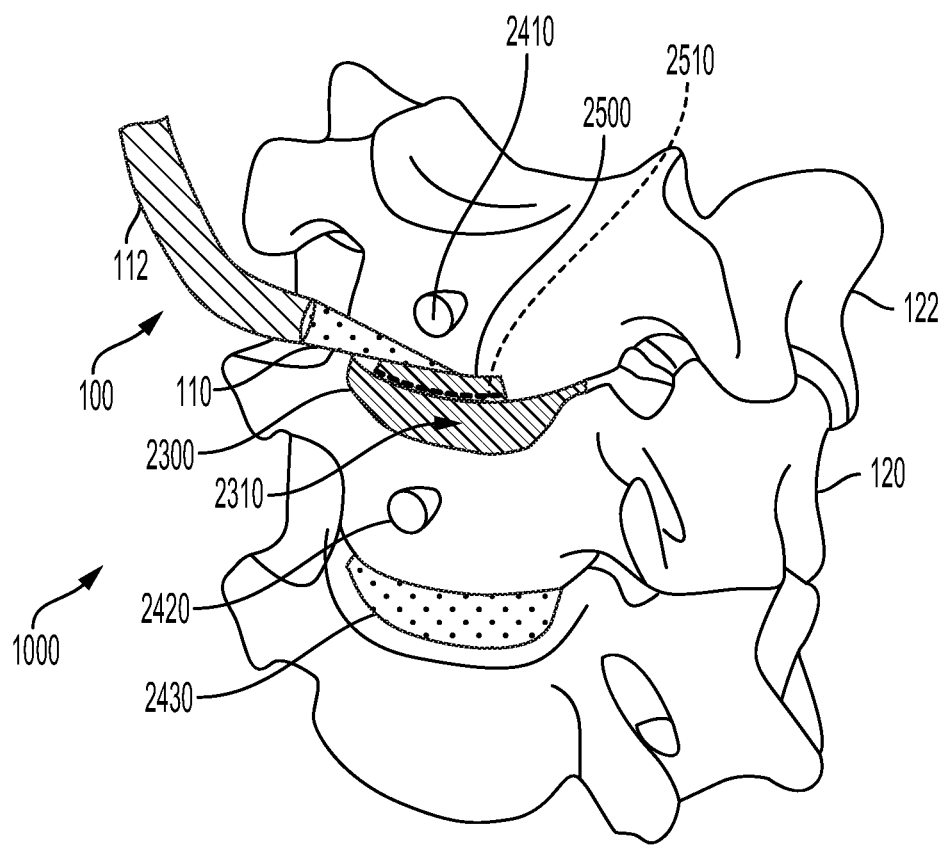
FIG. 25 shows commencement of in-situ formation of second, additional, additive implant, in the form of an inter-vertebrae plate, at a second in-situ position connected to the first additive in-situ implant, and at the second vertebra of the patient according to the second general embodiment of the present technology.

FIG. 25 shows commencement of in-situ formation of second, additional, additive implant, in the form of an inter-vertebrae plate at a second in-situ position connected to the first additive in-situ implant and at the second vertebra of the patient according to the second general embodiment of the present technology. While FIG. 25 is referenced as a commencement of formation, actual commencement can be earlier, depending on the implementation. If the interbody 2310 is printed first, that printing can be considered the commencement, or if the first in-situ printing involves growing the bone anchors 2410, 2420, that printing can be considered the commencement.

The additional in-situ-printed implant formation is indicated by numeral 2500. The extra-interbody portion can be referred to by any of a variety of terms, such as plate, surface portion, or surface connector.

In a contemplated embodiment, the pre-formed or pre-existing implant 2300 includes one or more connecting features at an interface 2510 to which the additional in-situ-printed implant 2300 is formed or connects. The connecting interface 2510 is indicated schematically by lead line in FIG. 25 at a corner formed between the additional in-situ-printed implant 2500 and the pre-implanted interbody 2300. The connecting interface 2510 however can be at any one or more location where the additional in-situ-printed implant 2500 is formed in contact with the pre-implanted interbody 2300. Example interface-feature locations include, for instance, the face 2310 of the interbody 2300, a front-top edge of the interbody, and a front-bottom edge of the interbody.

In various embodiments, the interbody/plate combination is built in the same surgical procedure, or the combination can be created by printing one of the two in a first procedure and the other in connection with the first in a second surgery, such as on a distinct day, month, or year from the first procedure.

The first-built implant (e.g., the interbody 2300), can be used as a guide for creating the second (e.g., plate 2500) intimately connected to the first and patient tissue (e.g., bone), whether the two are built in the same or distinct surgeries.

Interface features 2310 can include any of protrusions, roughening, indentations, grooves, hooks, overhanding or underhanging elements, the like, or other, to facilitate robust connection between the interbody 2300 and the additional in-situ-printed implant 2500 being formed in connection to the interbody 2300.

And as in other embodiments described herein, robust fixation between the interbody portion and the patient tissue 120, 122, and between the plate portion and the patient tissue, from printing in-situ, customized to and directly to patient anatomy, can be enhanced by preparing the tissue as desired, such as by roughening or grooving.

Figure 26:
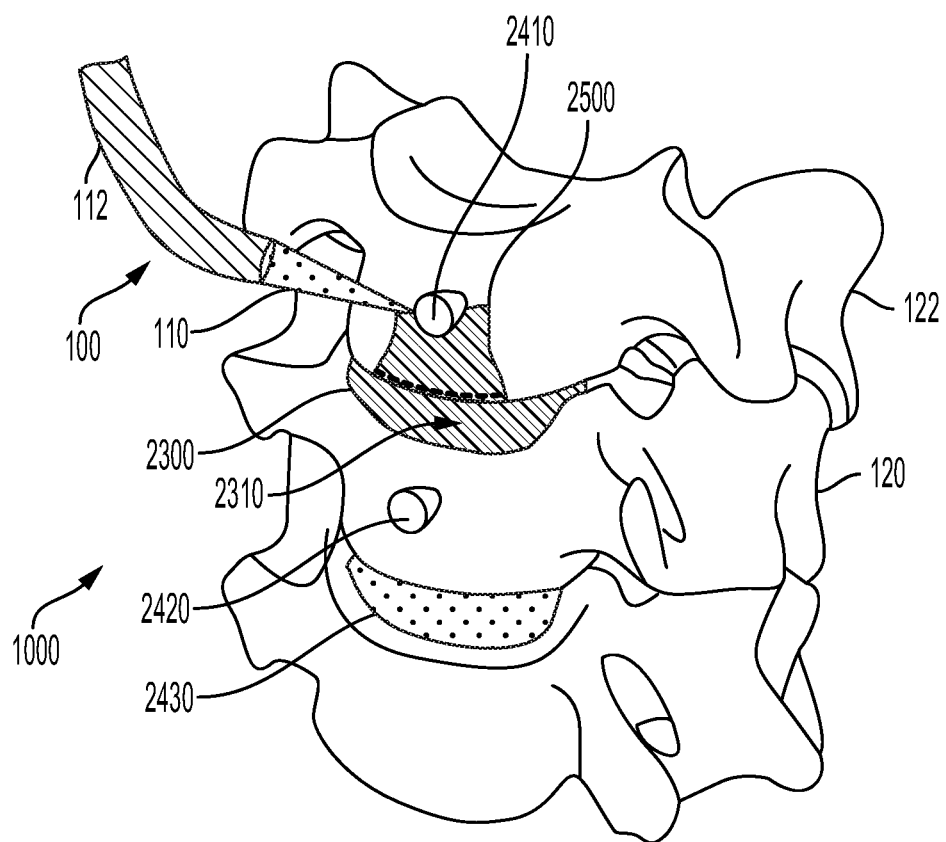
FIG. 26 shows continuation of forming the second additive in-situ implant, including forming the second implant around and in contact with a first bone anchor pre-secured to the second vertebra of the patient according to the second general embodiment of the present technology.

FIG. 26 shows continued formation of the second additive in-situ implant 2500, including forming the second implant around and in contact with the first bone anchor 2410. The in-situ printing may include any of the techniques described herein, including printing with only one material, or printing with two materials.

In one of the mentioned embodiments, in which the bone anchor 2410 is printed, the anchor 2410 can be printed in this step, before or with printing of a body of the adjacent additional in-situ-printed implant 2500. The same is possible in connection with the second bone anchor 2420, also shown in FIG. 26 and described further below in connection with FIG. 28.

Figure 27:
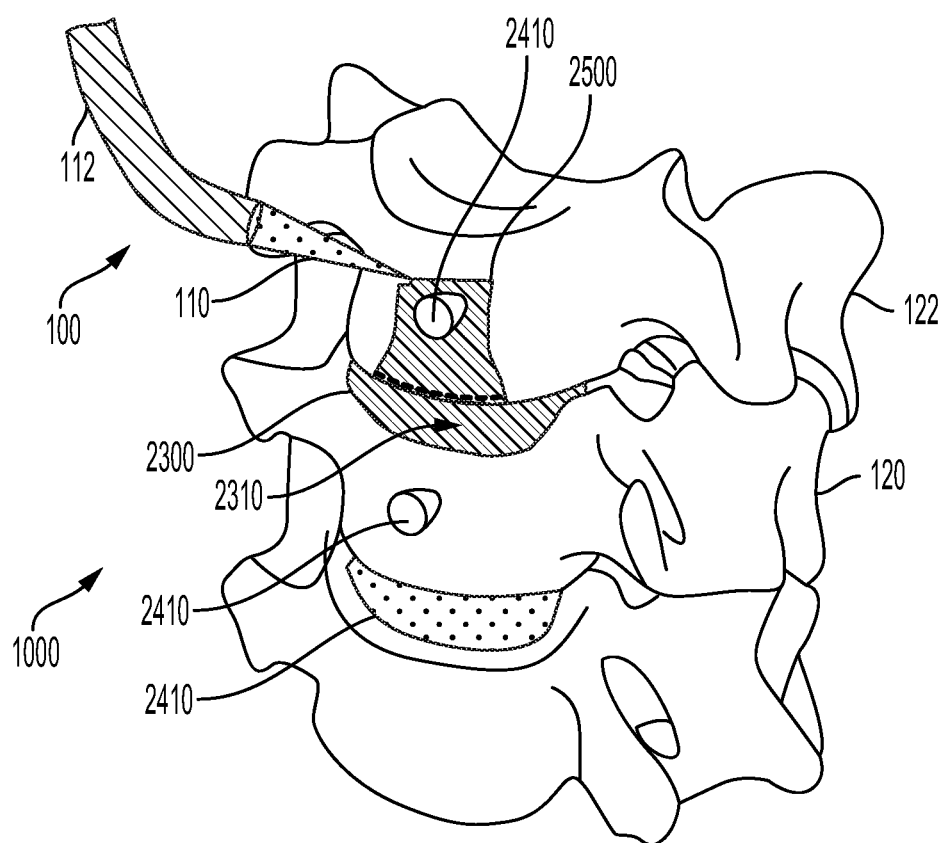
FIG. 27 shows continuation of forming the second additive in-situ implant at the second vertebra according to the second general embodiment of the present technology.

FIG. 27 shows continued formation of the second additive in-situ implant 2500 at the second vertebra 122 of the patient 100 according to the second general embodiment of the present technology.

Figure 28:
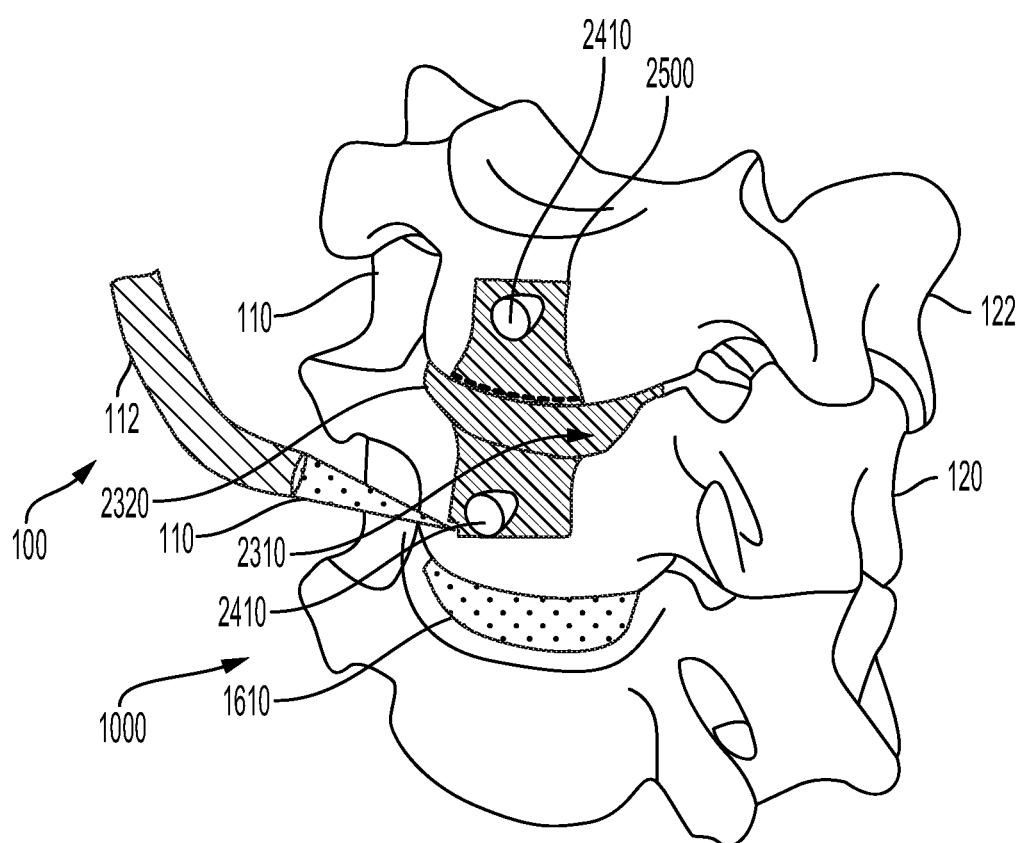
FIG. 28 shows completing of the second additive in-situ implant at the first vertebra of the patient, including forming the second implant around and in contact with a second bone anchor pre-secured to the first vertebra of the patient according to the second general embodiment of the present technology.

FIG. 28 shows completing steps of forming the second additive in-situ implant 2500 at the first vertebra 120 of the patient 100, including forming the second implant snuggly around a second bone anchor 2420 affixed to the first vertebra, according to the second general embodiment of the present technology.

The system 100 moves and prints the additional in-situ printed implant 2500 in various embodiments to have any desired dimensions—e.g., thickness, height, width, and shape.

It should be appreciated that, as with the other in-situ-grown or formed implants described herein, the resulting implant 2500 of this embodiment is highly customized to the patient anatomy, being formed adjacent and on or at patient tissue, including but not limited to the vertebrae 120, 122 in this example.

The implant 2500 of this embodiment, or any embodiment herein, can also include interface features to promote printing-material-to-tissue adhesion and/or connection, and/or strengthen the implant. Example interface features include surface roughening, surface shaping (e.g., teeth), and surface coating. The interface features can include, for instance, eyelets on the plate for receiving bone anchors (e.g., screws), if not pre-anchored FIGS. 29-33 show another technique for forming an interbody implant by in-situ printing. The implant can also be formed to include a plate portion, as shown in FIG. 33.

Figure 29:
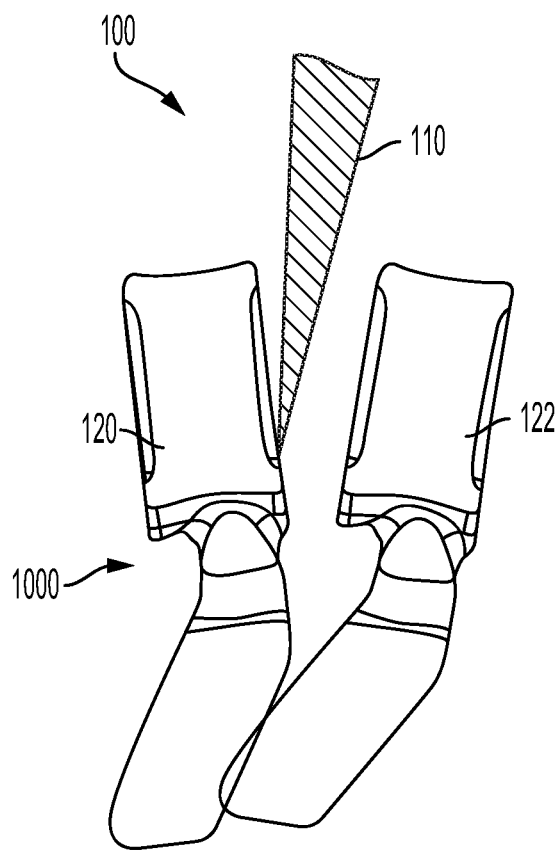
FIG. 29 is a lateral view of the dispensing component of the additive-manufacturing system positioned at an example starting position adjacent patient vertebrae according to a third general embodiment of the present disclosure.

Starting with FIG. 29, a lateral view is provided, of the dispensing component 1010 of the additive-manufacturing system 100 positioned at an example starting position adjacent the vertebrae 120, 122 of the patient 1000, according to a third general embodiment of the present disclosure.

Figure 30:
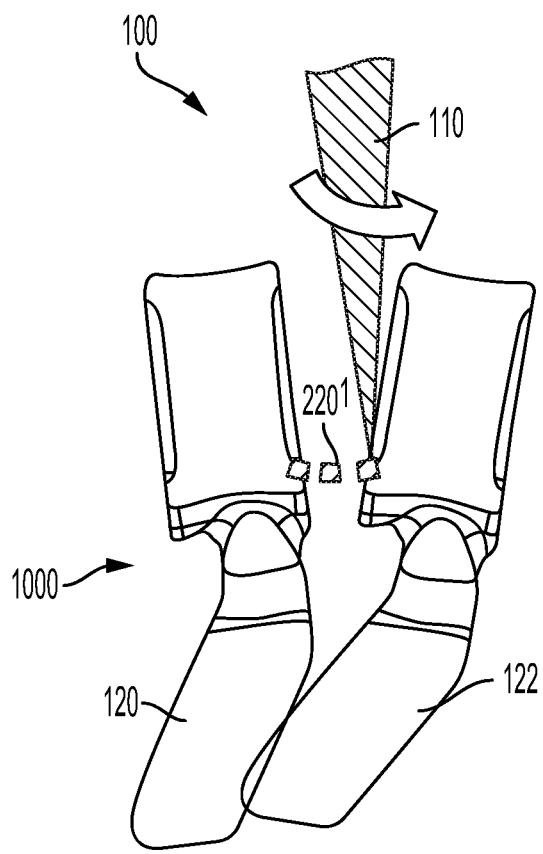
FIG. 30 is a lateral view of the dispensing component starting to dispense substrate material between the patient vertebrae according to the third general embodiment of the present disclosure.

FIG. 30 shows the dispensing component 110 starting to dispense substrate material $220^1$ between the patient vertebrae 120, 122 according to the third general embodiment of the present disclosure.

Figure 31:
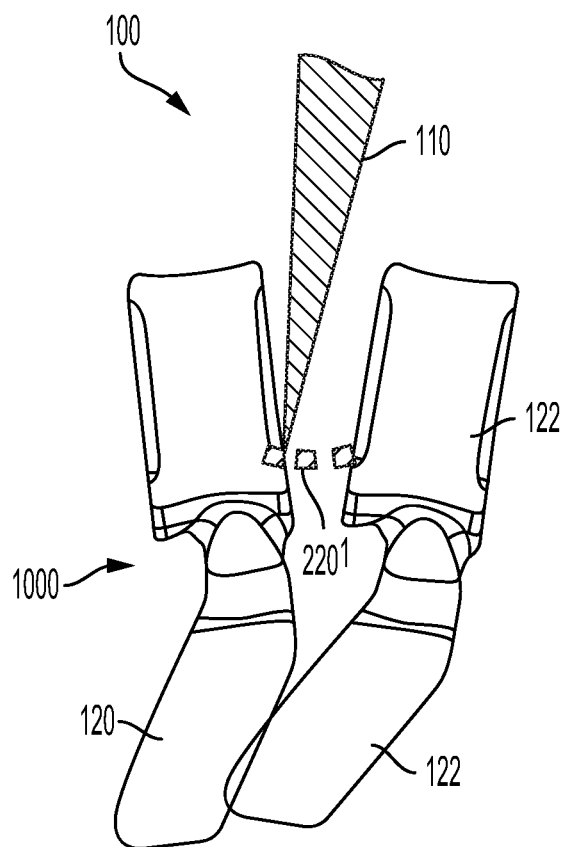
FIG. 31 is a lateral view of the dispensing component repositioned to generally the starting position for commencing depositing of catalyst according between the patient vertebra according to the third general embodiment.

FIG. 31 shows the dispensing component 110 repositioned to or adjacent the starting position (FIG. 29) for commencing dispensing of the second, catalyst, material $220^2$, according between the patient vertebrae 120, 122 according to the third general embodiment.

Figure 32:
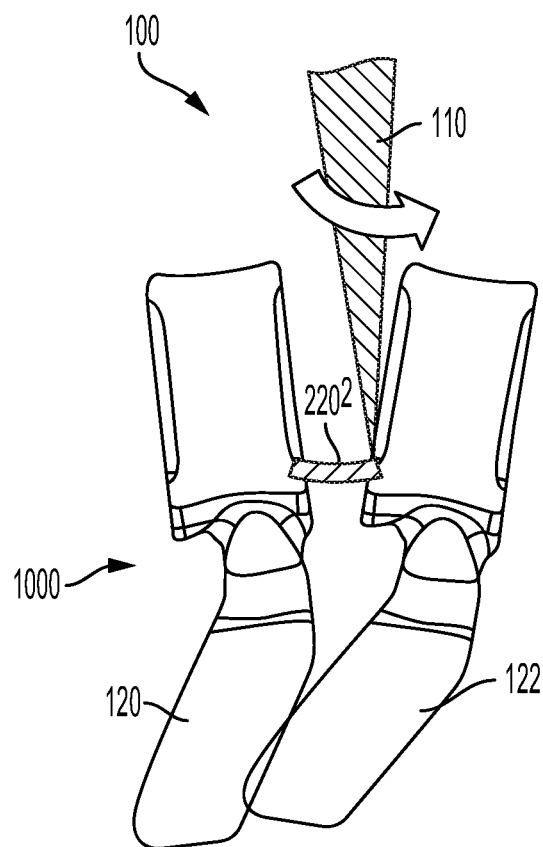
FIG. 32 is a lateral view of the dispensing component dispensing catalyst between the patient vertebra according to the third general embodiment.
Figure 33:
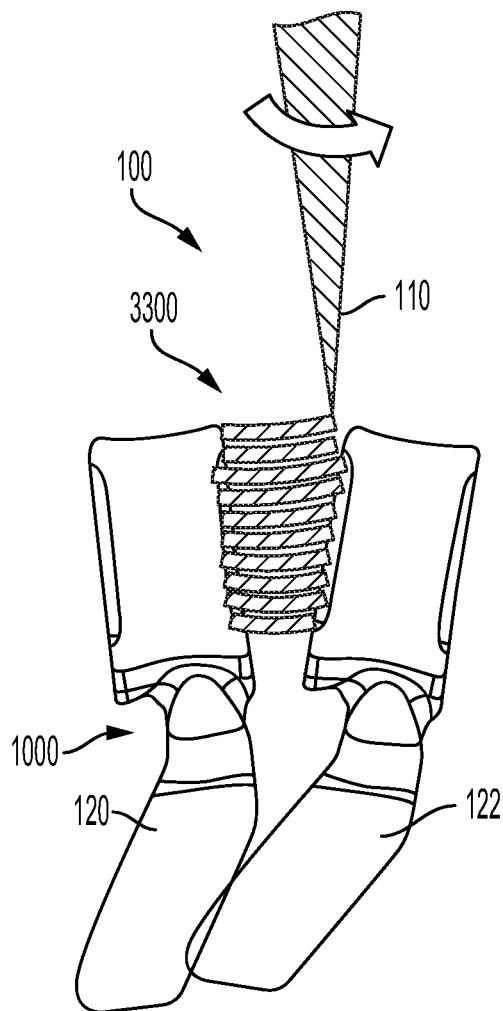
FIG. 33 is a lateral view of the dispensing component continuing to dispense printing material (e.g., substrate and adhesive) between the patient vertebra for forming the interbody implant in-situ according to the third general embodiment.

FIG. 32 shows the dispensing component 110 dispensing catalyst material $220^2$ to, on, or at the substrate material $220^1$, between the patient vertebrae 120, 122.

FIG. 33 is a lateral view of the dispensing component completing printing of material for forming the in-situ printed implant 3300, according to the third general embodiment.

It should be appreciated that, as with the other in-situ-grown or formed implants described herein, the resulting implant 3300 of this embodiment is highly customized to the patient anatomy, being formed adjacent and on or at patient tissue, including but not limited to the vertebrae 120, 122 in this example.

Figure 34:
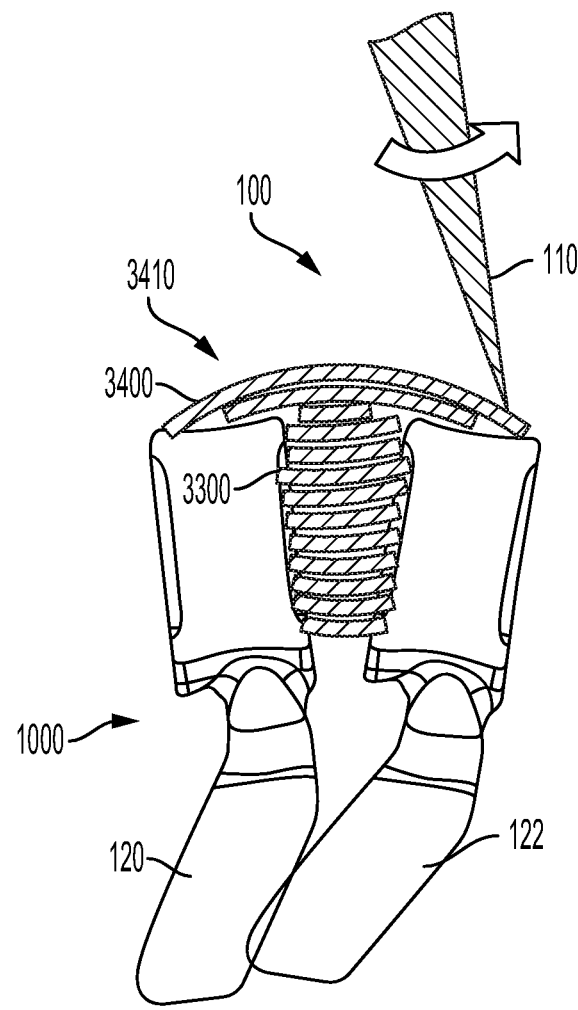
FIG. 34 is a lateral view of the dispensing component continuing to deposit substrate and catalyst, adjacent the interbody portion and the vertebrae to form a facial plate portion connected to the interbody portion, forming in-situ a combined interbody/plate implant according to the third general embodiment.

FIG. 34 is a lateral view of the dispensing component 110 continuing to dispense substrate $220^1$ and catalyst $220^2$, adjacent the previously in-situ grown or formed interbody 3300, and adjacent and in contact with the vertebrae 120, 122 of the patient 1000 to form a facial-plate portion 3400 connected to the interbody portion 3300, thereby printing in-situ a combined interbody/plate implant 3410, according to the third general embodiment.

While the term facial is used, the term is not limiting for all embodiments. The extra-interbody portion, formed outside of the interbody space and in connection with an exterior surface of at least two vertebrae. The extra-interbody portion can be referred to by any of a variety of terms, such as plate, surface portion, or surface connector.

The plate portion can be referred to by any of a variety of terms, such as plate, surface portion, or surface connector.

As in other embodiments described herein, robust fixation between the interbody portion 3300 and the patient tissue 120, 122, and between the plate portion and the patient tissue, from printing in-situ, customized to and directly to patient anatomy, can be enhanced by preparing the tissue as desired, such as by roughening or grooving.

And, as also described in connection with other embodiments, herein, either or both of two connecting implants 3300, 3400, or portions 3300, 3400 of the implant 3410 can be formed to include interface features 2310, such as protrusions, roughening, indentations, grooves, hooks, overhanding or underhanging elements, the like, or other, to facilitate robust connection between them.

The implant 3400 of this embodiment, or any embodiment herein, can also include interface features to promote printing-material-to-tissue adhesion, and/or strengthen the implant. Example interface features include surface roughening, surface shaping (e.g., teeth), and surface coating, or physical features that penetrate patient tissues, such as bony surfaces, e.g., vertebral bodies, or features for attaching post-printing devices such as eyelets for inserting screws.

Figure 35:
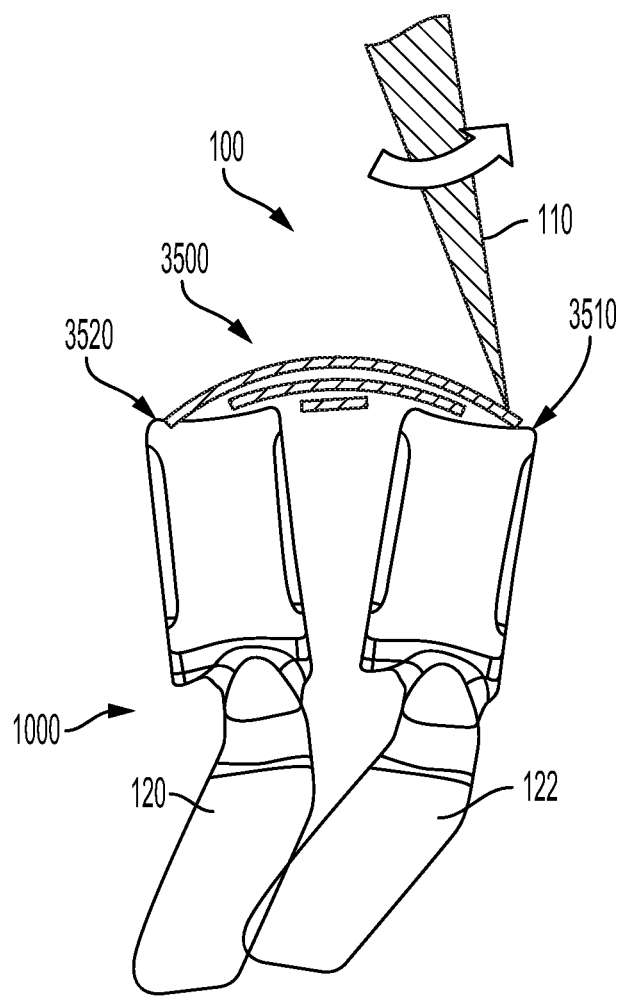
FIG. 35 is a lateral view of the dispensing component depositing printing material facially to and between the vertebrae forming in-situ a plate implant fixing the vertebrae together, according to a fourth general embodiment of the present technology.

FIG. 35 is a lateral view of the dispensing component 110 positioned by the robotics 1030 and armature 112 of the system 100 for dispensing. The system 100 by way of the dispensing component 110 deposits printing material (e.g., substrate and catalyst) to, or to and between, faces 3510, 3520 of the vertebrae 120, 122 forming in-situ a plate implant 3500 fixing the vertebrae together, according to a fourth general embodiment of the present technology.

The embodiment can include pre-implantation, or in-situ printing of bone anchors (not shown in FIG. 35) to which the plate implant 3500 is grown or formed. Anchor pre-implantation and printing is described above with the embodiment of FIG. 26.

It should be appreciated that, as with the other in-situ-grown or formed implants described herein, the resulting implant 3500 of this embodiment is highly customized to the patient anatomy, being formed adjacent and on or at patient tissue, including but not limited to the vertebrae 120, 122 in this example.

And as in other embodiments described, robust fixation between the between the in-situ-grown or formed plate 3500 and the patient tissue, from printing in-situ, customized to and directly to patient anatomy, can be enhanced by preparing the tissue as desired, such as by roughening or grooving.

And the implant 3500 of this embodiment, or any embodiment herein, can also include interface features to promote printing-material-to-tissue adhesion and/or connection, and strengthen the implant. Example interface features include surface roughening, surface shaping (e.g., teeth) and surface coating.

Some embodiments address issues related to challenging patient-tissue spacing. Sometimes an entry opening to a target implant region of the patient 100 is too small to fit a pre-made implant through. Various techniques of the present disclosure described above can be used to remedy these situations. As other example solutions, FIGS. 37-40 show a manner of doing so, and FIGS. 41-44 shows another.

As an example of such fitting challenge, FIG. 36 shows a side view of the patient vertebrae 120, 122 spaced such that a pre-printed or otherwise pre-made interbody implant 3600, sized for a particular interbody space 3610, cannot be readily passed to position in the space. Anterior interbody spacing 11, at an opening 3620, of the patient 1000 is smaller than an entry height 13 of the implant 3600.

Figure 37:
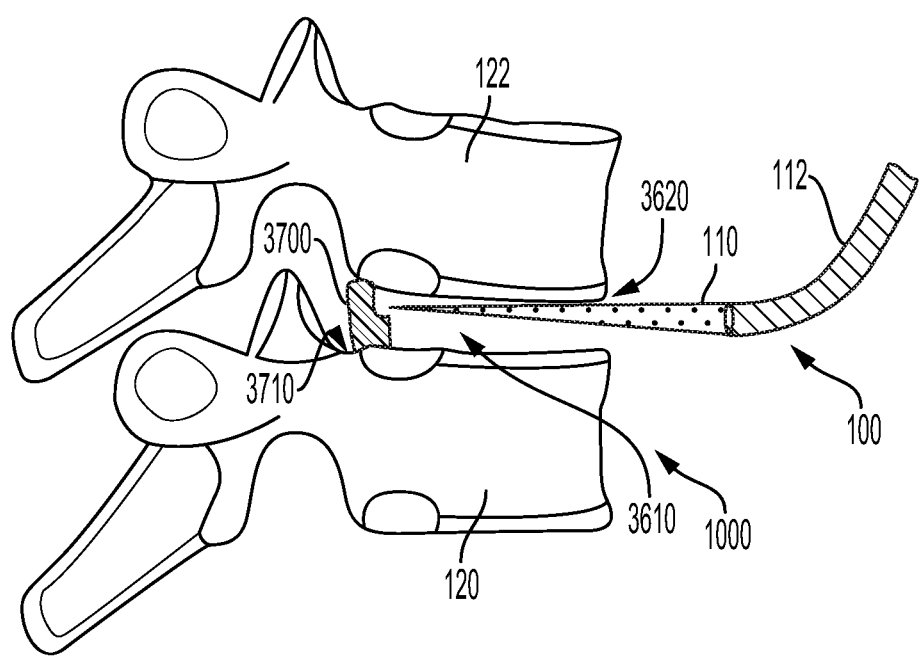
FIG. 37 shows commencement of in-situ formation of a sixth interbody implant according to a sixth general embodiment of the present technology.

As a first of the mentioned solutions for the challenge presented by context of FIG. 36, FIG. 37 shows commencement of in-situ formation of a fifth interbody implant 3700 according to a fifth general embodiment of the present technology.

The dispensing component 110 is sized, shaped, and maneuvered to easily fit through the anterior opening 3620 of FIG. 36, and extend into the inter-tissue space 3610 and to a posterior region 3710 between the vertebrae 120, 122.

Figure 38:
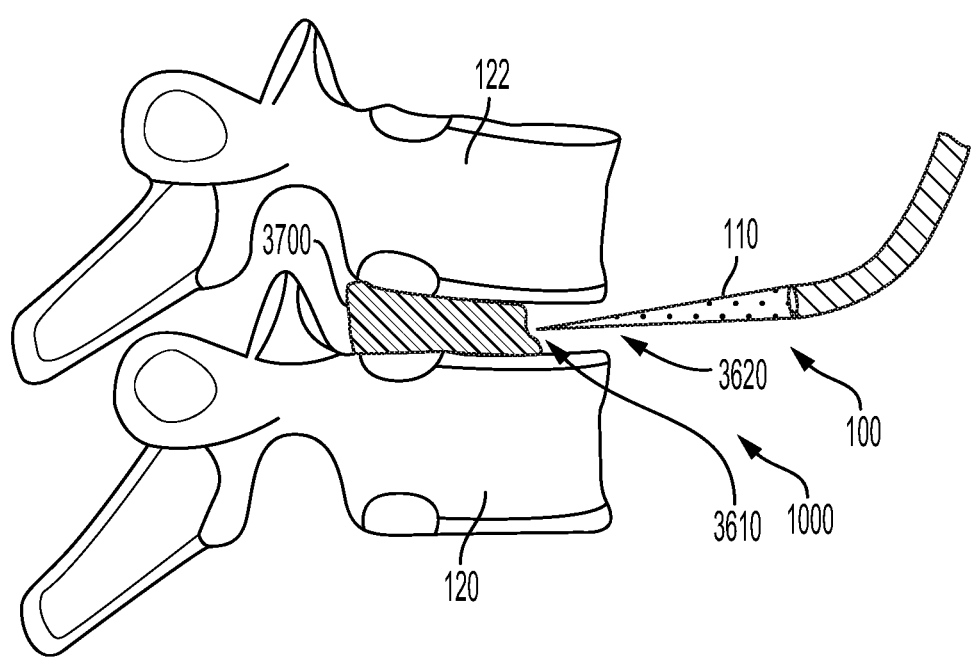
FIG. 38 shows continued in-situ formation of the sixth interbody implant.

FIG. 38 shows continued in-situ formation of the fifth interbody implant 3700, posterior-to-anterior by way of example.

Figure 39:
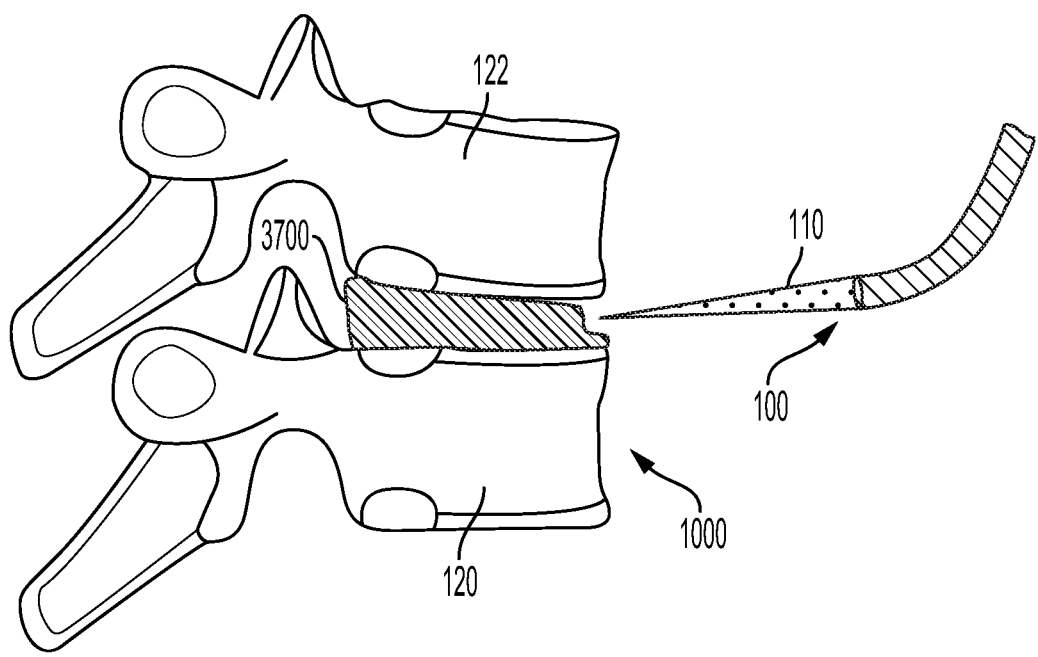
FIG. 39 shows final in-situ steps for forming the sixth interbody implant.

FIG. 39 shows final in-situ steps completing for forming the fifth interbody implant 3700.

Figure 40:
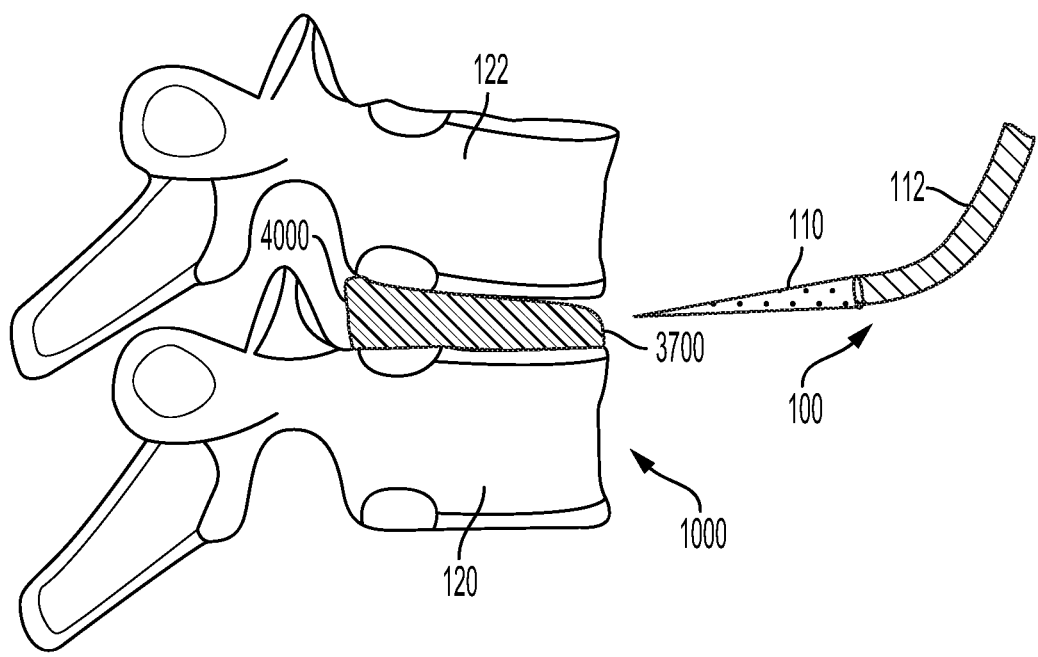
FIG. 40 shows the fourth in-situ-formed interbody completed in the patient according to the sixth general embodiment.

FIG. 40 shows the in-situ-grown or formed interbody 3700 completed in the patient 1000 according to the fifth general embodiment.

As in other embodiments described herein, the robust fixation between the interbody portion and the patient tissue 120, 122, and between the in-situ-grown or formed implant 3700 and the patient tissue 120, 122, from printing in-situ, customized to and directly to patient anatomy, can be enhanced by preparing the tissue as desired, such as by roughening or grooving.

It should be appreciated that, as with the other in-situ-grown or formed implants described herein, the resulting implant 3700 of this embodiment is highly customized to the patient anatomy, being formed adjacent and on or at patient tissue, including but not limited to the vertebrae 120, 122 in this example.

The implant 3700 of this embodiment, or any embodiment herein, can also include interface features to promote printing-material-to-anchor adhesion and/or connection, and strengthen the implant. Example interface features include surface roughening, surface shaping (e.g., teeth), and surface coating, or physical features that penetrate patient tissues, such as bony surfaces, e.g., vertebral bodies, or features for attaching post-printing devices such as eyelets for inserting screws.

Figure 41:
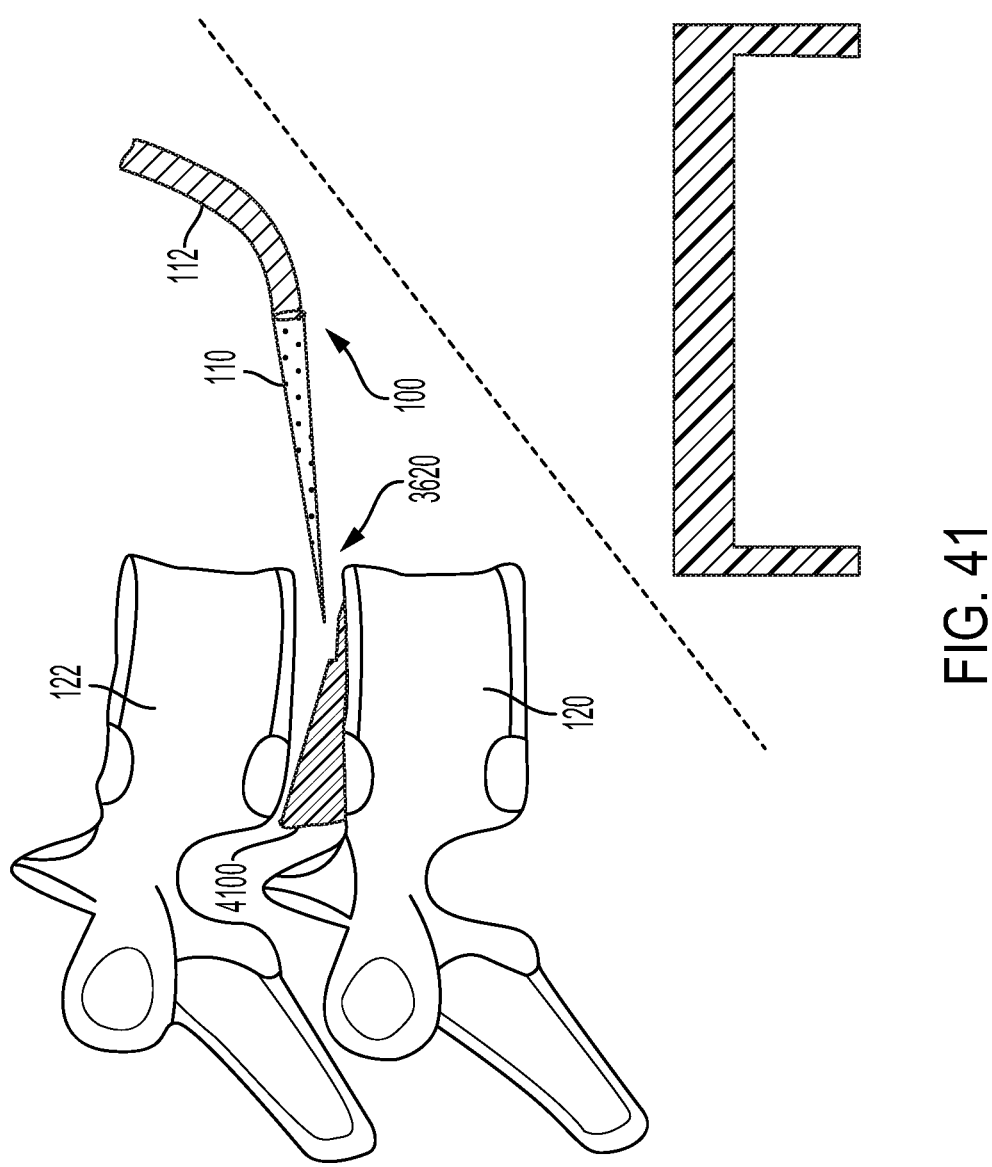
FIG. 41 shows commencement of in-situ formation of a first component of a sixth, multi-component, interbody implant according to a sixth general embodiment.

As another solution to the fit challenges indicated by FIG. 36, FIG. 41 shows commencement of in-situ formation of a first part 4100 of a multi-component, interbody implant, between the vertebrae 120, 122 of the patient 1000, according to a sixth general embodiment.

Figure 42:
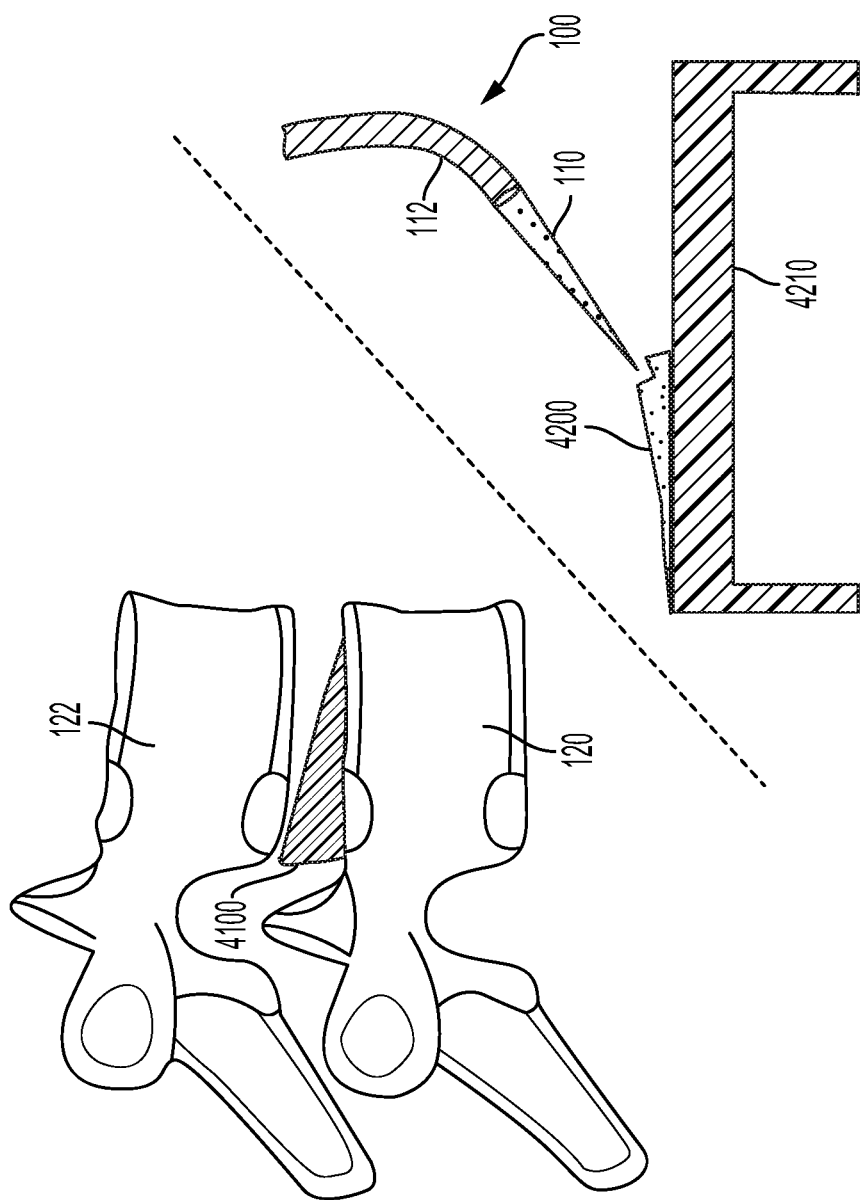
FIG. 42 shows commencement of additive formation of a second component of the sixth, multi-component, interbody implant according to the sixth general embodiment.

FIG. 42 shows commencement of additive formation of a second part 4200 of the multi-component interbody implant according to the sixth general embodiment. The formation is shown schematically on a table 4210, such as a prep table in the surgical room.

In a contemplated embodiment, the surface on which the second part is grown or formed includes a patient-tissue surface, such as an exterior of vertebra or other bone.

Figure 44:
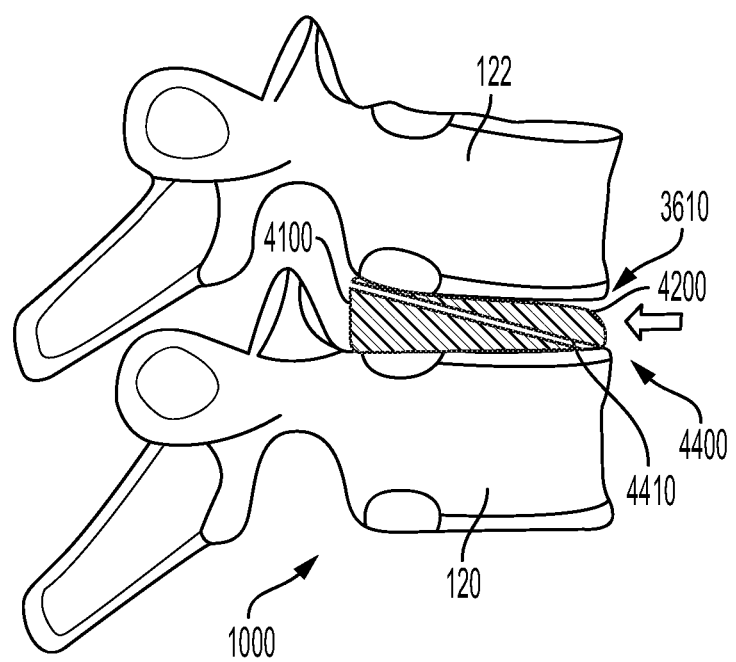
FIG. 44 shows the second component interbody implant having been forced to a desired position directly adjacent the first component, forming the sixth exemplary interbody according to the sixth general embodiment.

In a contemplated embodiment, the second part 4200 is grown or formed at least partially on the first part 4100. The connection between the two may be slight in various ways, to allow ready relative movement between the parts after the second part is completed (such as to accomplish a final, combined, implant shape, such as shown in FIG. 44) The slight connection may be from printing only one or more small pieces, such as tabs, on the first part 4100, and printing the second part on the small pieces.

The second part 4200 can then be easily pushed in a posterior direction, breaking the small pieces, the reach the final implant shape. Another example of a slight connection can be from a manner in which the second part is printed on the first, such as after a top layer of the first part has cured or solidified by an amount sufficient to enable the second part printed thereon to be easily moved relative to the first, thereby again allowing the subsequent relative movement.

The second part is in various embodiments grown or formed real-time by the system 100, as shown, or is a pre-manufactured component, whether printed. In various embodiments, the second part 4200 is made to have a size and shape corresponding to size and shape of the first part 4100 and to patient anatomy, namely the vertebrae 120, 122. Likewise, the first part 4100 is made to have a size and shape corresponding to size and shape of the second part 4200, as well as to the patient anatomy.

Figure 43:
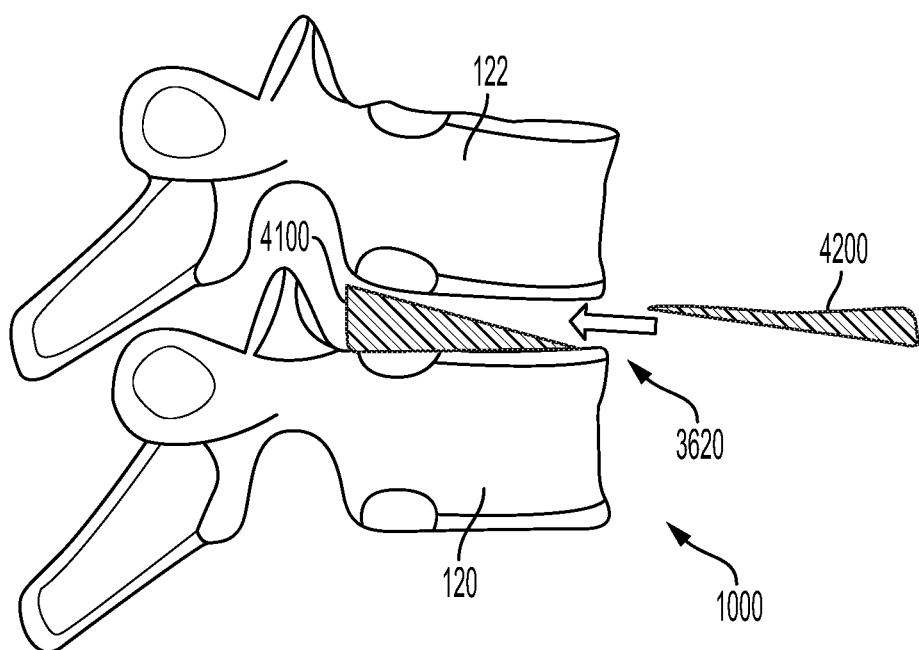
FIG. 43 shows the second component of the sixth embodiment of the interbody implant positioned for insertion to an in-situ position adjacent the first component.

FIG. 43 shows the second part 4200 of the sixth embodiment of the interbody implant positioned for insertion, adjacent the tissue opening 3620.

FIG. 44 shows the second component 4200 forced to a final position shown in FIG. 44 adjacent the first part 4100. The movement may cause the second component 4200 wedge between the first part 4100 and the second vertebra 122, which may slightly push one or both vertebra away from the other. The forcing causes the second part 4200 to, with the first part, substantially fill the inter-tissue space 3610 of the patient 1000 as desired. This forms the multi-component interbody implant in-situ (being grown or formed at least partially in-situ), according to the sixth general embodiment.

In a contemplated embodiment, the system 100 applies or is used to apply the force to move the second part 4200 into place. The dispensing component 110 may be used to apply the force, for instance, by motivation of a surgeon or the robotics 1030 controlled by the system controller 1050.

Spacing between the parts 4100, 4200 can have any size or dimension, desired, or the parts can be formed and connected so that there is no, or substantially no, space between them. Spacing may be desired in some cases, such as to allow relative movement between the parts 4100, 4200 as the patient moves and heals (e.g., inter-vertebral fusing) after the procedure.

Either or both of the parts 4100, 4200 can have interface features, indicated schematically (by location) by reference numeral 4410. Interface features 4410 can include any of protrusions, roughening, indentations, grooves, hooks, overhanding or underhanging elements, the like, or other, to facilitate robust connection between the parts 4100, 4400.

As another example, the parts 4100, 4200 can include matching features that facilitate accurate relative positioning of the two. Or have matching, or geometrically-corresponding, features promoting connection between the two, such as by one being made to have one or more rails and one having one or more corresponding slots to receive the rails. Or, to promote connection between them, and possible to also provide an indication of proper relative positioning, such as by haptic feedback to the system 100 or surgeon maneuvering the second part 4200 into place adjacent the first part 4100.

In various embodiments the second part 4200 can be pre-manufactured. In some cases, the first part 4100 is structured (sized and shaped, for instance) to accommodate (e.g., receive) the second part 4200. The first part 4100 may be grown or formed to have a recess, hollow, void, or other spacing, for instance, to which the second part 4200 can be connected and/or into which the second part 4200 can be placed.

The first part 4100 can be printed after the second part 4200 is implanted. The first part 4100 can be printed in and/or around. The first part 4100, and thus the combination, would thus be patient-anatomy optimized. Another benefit of these embodiments can be time savings, and cost savings from time and perhaps labor and material savings.

The second part when pre-made per these embodiments can have any desired form, including any existing parts for the same or similar purpose—e.g., existing spinal implants.

One or more pre-made parts can be included in a set sold or provided to the surgical team.

As in other embodiments described, the robust fixation between the interbody parts 4100, 4200 and the patient tissue 120, 122, and between the resulting in-situ-grown or formed implant 4400 and the patient tissue 120, 122, from printing in-situ, customized to and directly to patient anatomy, can be enhanced by preparing the tissue as desired, such as by roughening or grooving.

The implant 4400 of this embodiment, or any embodiment herein, can also include interface features to promote printing-material-to-anchor adhesion and/or connection, and strengthen the implant. Example interface features include surface roughening, surface shaping (e.g., teeth), and surface coating, or physical features that penetrate patient tissues, such as bony surfaces, e.g., vertebral bodies, or features for attaching post-printing devices such as eyelets for inserting screws.

It should be appreciated that, as with the other in-situ-grown or formed implants described herein, the resulting implant 4400 of this embodiment is highly customized to the patient anatomy, being formed adjacent and on or at patient tissue, including but not limited to the vertebrae 120, 122 in this example.

Figure 45:
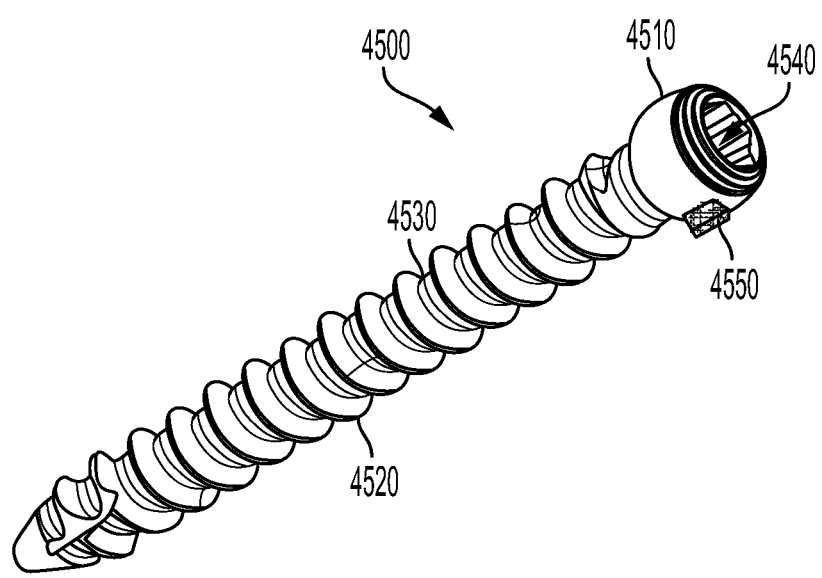
FIG. 45 shows a perspective view of an exemplary fiducial screw according to a seventh general embodiment of the present technology.

Turning to a seventh, general embodiment of the present disclosure, FIG. 45 shows a perspective view of an exemplary fiducial bone anchor implant 4500, such as a bone screw.

The bone anchor 4500 can in various implementations be referred to as a fiducial anchor, or fiducial screw, and a function thereof can include an ability to be visualized readily by scanning or imaging equipment based on a characteristic of the implant.

Example recognition characteristics include shape of features. The anchor 4500 can also include detectable features, whether for recognition in the sense used here. These can be visible, or not visible to the eye. Examples include bar codes, QR codes, RFID tags, ultraviolet inks, and surface or embedded markers. Markers can include techno-aide (TA) markers, or others having one or more select materials that look or scan/image in a unique way for anchor identification, anchor or anchor-portion recognition, position determination, or orientation determination.

In a contemplated embodiment, the recognition features include a material of the implant.

An example of the mentioned scanning or imaging equipment is the surround scanner 1092, or the navigation system 1093, of FIG. 10.

The anchor 4500 includes a head 4510, a shaft 4520, and at least one thread 4530 for fixing the implant to bone. The head 4510 includes driving features 4540 in various embodiments. The driving features are configured to be engaged by a driver instrument (not shown). An example driving feature is a hex shape, as shown in FIG. 45.

Any aspect of the anchor implant 4500 can have the fiducial, readily recognizable characteristic(s). The head 4510 is an example. The head 4510 can have any of a variety of unique, or special, fiducial shapes or geometries for the fiducial purpose. In various embodiments, the head 4510 is generally ball-shaped.

When having fiducial characteristics, the head 4510 may be referred to as a fiducial head, or fiducial portion of the anchor 4510. The fiducial head 4510 is in various embodiments configured (e.g., fiducially shaped) and/or constituted (having fiducial material, e.g.) to promote ready recognition by scanning or imaging equipment, such as the surround scanner 1092, or the navigation system 1093 sensor.

The head shape can be unique, or special, by being distinct from conventional screw head shapes, for instance. And the processor of the controller 1050, executing the instruction stored in the memory of the computing components 1060, recognizes the distinct shape in the scan data, and with that the position of the head or anchor.

Other portions of the screw, such as the shaft 4520 or the thread 4530 thereon, can also have fiducial features, along with or instead of the head, to be highly fiducial.

More particularly, the fiducial head 4510, or any fiducial component of the anchor 4500, has a specific geometry that software, of the controller 1050 of the system 100 (see e.g., FIG. 10) is programmed to recognize in scanner or image data.

In the case of the fiducial head 4510, an example geometry can be, for instance, conical, cubical, or cylindrical—such as by including, e.g., a cylindrical post.

As another example fiducial geometry, the implant 4500 can have a fiducial characteristic that is not a primary component of the implant, such as the head, shaft or thread of the implant 4500. Such characteristic can be temporary, by being removable after they have served their purpose, which can be prior to an end of the printing steps or any time before an end of the procedure.

An example add-on fiducial characteristic is a protrusion 4550. The add-on features can be formed with or added to the implant 4500, such as by printing by the system, which may also print the entire implant 4500. The protrusion or other fiducial feature can be configured and/or attached to the implant 4500 to be readily removed during the procedure. Removal can include snapping off or pulling off. While surgical staff can effect the removal, in a contemplated embodiment the controller 1050 is configured to, by the processor executing instruction stored in the controller, maneuver an instrument, such as the dispenser 110, to remove the fiducial feature.

The fiducial implant component, such as the fiducial head 4510, or fiducial add-on feature, such as the protrusion 4550, can as mentioned include material especially conducive to visualizing. The material is configured to be especially sensed and/or especially recognized by the scanner/imaging equipment and/or by the software of the controller 1050 receiving the image data. Example scanning techniques include x-ray, MRI, and camera.

The fiducial anchor 4500 in various embodiments includes interface features to promote engagement of in-situ printing material (see e.g., numeral 220 in FIGS. 49-53) to the anchor 450. Interface features can also promote printing-material 220-to-anchor 450 adhesion and/or connection, and strengthen the anchor 4500. Example interface features include surface roughening, surface shaping (e.g., teeth), and a surface coating.

Figure 46:
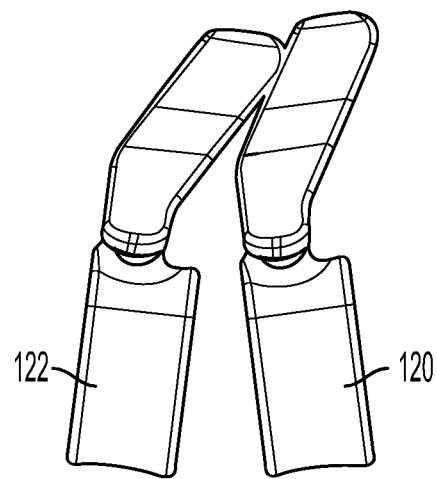
FIG. 46 shows a lateral view of patient vertebrae to be joined.

FIG. 46 shows a lateral view of patient vertebrae 120, 122 to be fused.

Figure 47:
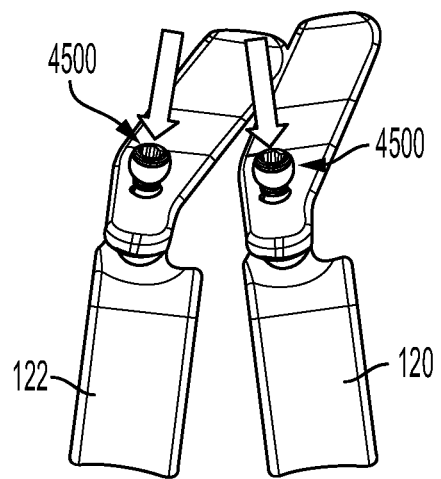
FIG. 47 shows the lateral view of patient vertebrae, each having a fiducial screw of FIG. 45 anchored to an anterior, e.g., pedical, portion thereof.

FIG. 47 shows the lateral view with bone anchors 4500 anchored into an anterior, pedical, portion of the vertebrae 120, 122.

In various embodiments, the anchors 4500 are printed in place. The technique includes pre-forming bores at the anchor locations of the vertebrae 122, 120, and growing the anchors 4500 therein, and therefrom.

In one embodiment, the anchors 4500 are mechanically driven (by threading, twisting, or otherwise forcing the anchor) into the bone, such as by a conventional driver instrument (not shown).

The anchor 4500 can be a metal screw, for instance. The anchors are in various embodiments driven in by system components (not shown in detail), such as an anchor driver connected to an end of the robotics armature 112. The driver end effector, in a modular embodiment, is a driver end effector selectively connected to the armature instead of the dispensing component and is readily removable after use. The desired dispensing end effector 110 is then connected to the armature 112 for the printing steps.

It is contemplated that boring equipment (not shown in detail) for this purpose can also be part of the system 100. One or more boring end effectors can be attached to the robotics armature, such as an additional effector with the nozzles in the views of FIGS. 2-9. Or the boring end effector can be connected to the armature selectively as a removable end effector.

Such additional equipment (driver and boring equipment), whether modular, is considered illustrated by the end effector 110 shown in FIG. 24 to simplify the drawings.

FIG. 48 is a lateral view of the dispensing component 110 of the additive-manufacturing system 100 positioned at an example starting position adjacent one of the fiducial screws 4500, or at least adjacent one of the patient vertebrae, for commencing deposit of printing material (e.g., substrate and catalyst) for in-situ printing an implant connecting the vertebrae 120, 122, according to the seventh general embodiment of the present disclosure.

The starting position can be determined by the controller 1050 based on anchor positioning determined by recognition of the fiducial characteristic of the anchor indicated in scan or image data taken prior to the dispensing component 110 positioning. The controller 1050 then controls the robotics componentry 1030 to position the dispensing component 110 accordingly.

In various embodiments, the controller 1050, also for determining the starting position, recognizes patient anatomy adjacent the implant location.

The controller 1050 may incorporate such fiducial implant and/or patient anatomy information into a pre-established in-situ printing plan, or generate the plan based on fiducial implant and/or patient anatomy information.

FIG. 49 is a lateral view of the dispensing component 110 of the additive-manufacturing system 100 being moved, by the robotics equipment 1030 or surgeon, and depositing substrate material $220^1$ between the vertebrae 120, 122 for in-situ printing the connecting implant, connecting the bone anchors 4500 and thereby the vertebrae.

Figure 50:
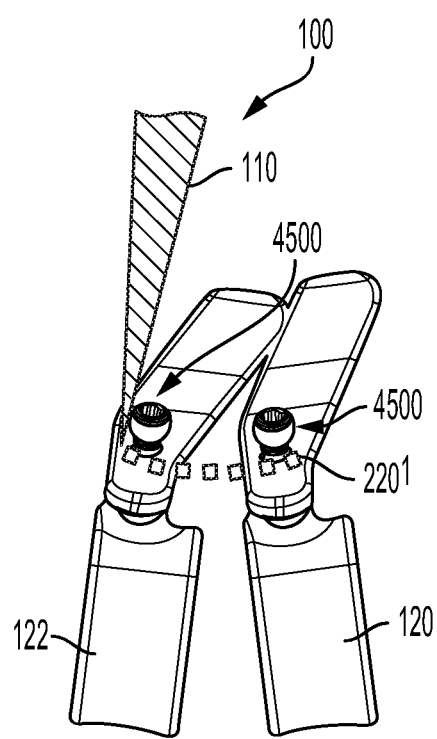
FIG. 50 is a lateral view of the dispensing component of the additive-manufacturing system repositioned to the starting position for applying substrate material between the vertebrae, connecting the screws and thereby the vertebrae, according to the seventh general embodiment of the present disclosure.

FIG. 50 shows the dispensing component 110 of the additive-manufacturing system 100 repositioned to, or adjacent to, the starting position (from FIG. 45) for applying catalyst.

Figure 51:
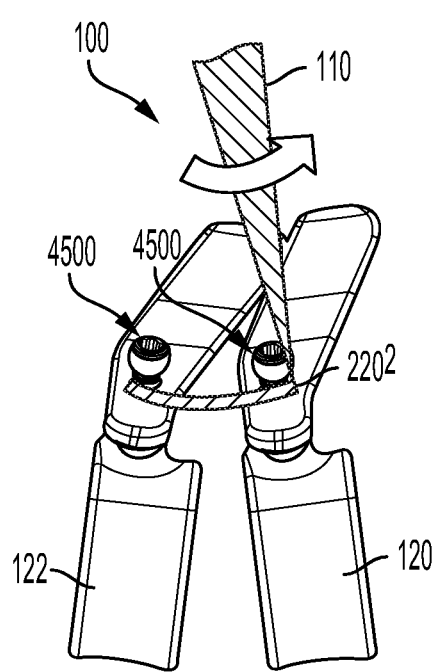
FIG. 51 is a lateral view of the dispensing component of the additive-manufacturing system applying catalyst, connecting the screws and thereby the vertebrae, according to the seventh general embodiment of the present disclosure.

FIG. 51 shows the dispensing component 110 of the additive-manufacturing system 100 being moved and applying catalyst $220^2$ on, to, or at the substrate material $220^1$, connecting the bone anchors 4500, and thereby the vertebrae 120, 122.

Figure 52:
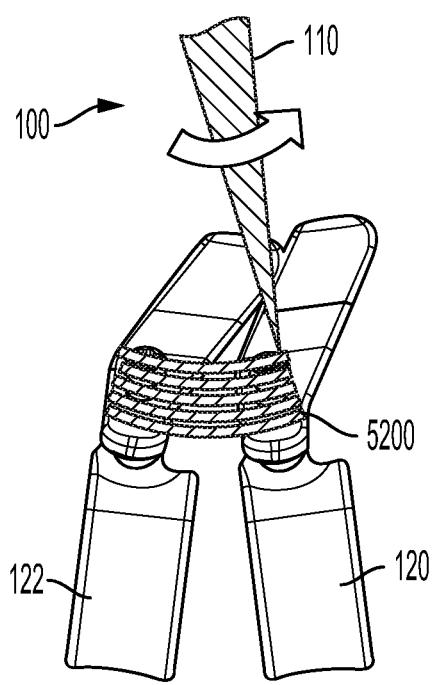
FIG. 52 is a lateral view of the dispensing component of the additive-manufacturing system completing application of printing material, connecting the screws and thereby the vertebrae, to form the in-situ implant, according to the seventh general embodiment of the present disclosure.

FIG. 52 is a lateral view of the dispensing component 110 of the additive-manufacturing system 100 completing depositing of printing material $220^2$, $220^1$, connecting the bone anchors 4500, and thereby the vertebrae 120, 122.

Figure 53:
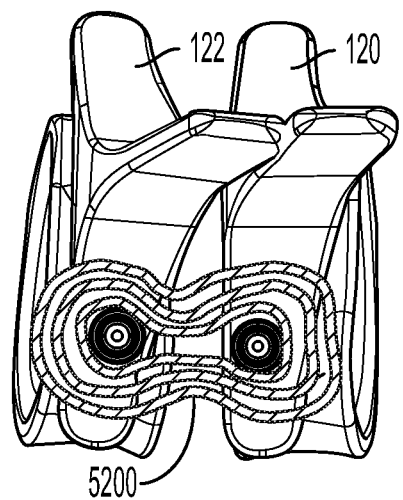
FIG. 53 shows an oblique perspective view of the printed in-situ implant, connecting the vertebrae, according to the seventh general embodiment of the present disclosure.

FIG. 53 shows an oblique perspective view of the in-situ printed connecting implant 5200, connecting the vertebrae 120, 122, according to the seventh general embodiment of the present disclosure.

Additional non-woven fibrous implant Aspects:

Other embodiments of the present technology may include additive-manufactured non-woven fibrous implants. Example non-woven fibrous implants may include components formed at a manufacturing center, surgical center, and/or components that may be in-situ, printed, formed, etc. In some embodiments, non-woven fibrous implants may also be considered motion-sparing implants or at least have some motion-sparing properties, i.e., some shock absorbing, shock suppressing, and/or force dampening properties as would be understood by skilled artisan. In some embodiments, non-woven fibrous implants may be formed in discrete portions that are positioned and/or re-positioned according to an iterative process. In some embodiments, non-woven fibrous implants may be formed between pre-printed or pre-manufactured endplates positioned within an intervertebral disc space. In other embodiments, a plurality of non-woven fibrous implants may be sequentially formed and repositioned and/or otherwise manipulated in order to fill a disc space between adjacent vertebrae and restore, support, or otherwise correct alignment, nerve endings, and/or range of motion of a patient's spine. In some embodiments, non-woven fibrous implants may be formed as a composite implant having rigid properties and motion-sparing properties and fibrous portions having varying densities. For example, a composite non-woven fibrous implant may have a rigid lattice like framework that is filled or partially filled with a relatively softer pliable material and discrete sections formed of a first fibrous material having a first diameter and a second fibrous material having a second diameter different from the first diameter. As used herein, the term "rigid" is intended to have its ordinary technical meaning referring to stiffness of a material where a material may be considered "rigid" if it is stiff or hard and in some cases a "semi-rigid material" may be marginally deformable or flexible. As used herein, the term "pliable" is intended to have its ordinary technical meaning referring to materials that are easily bent, compressed, and/or flexible. In some instances, a rigid material may be considered rigid relative to another material that it is more pliable and vice-versa.

The term non-woven fibrous implant, or composite non-woven fibrous implant is used primarily herein to describe, for example, the subject interbody implants 10000, 11000, 12000 or discrete components thereof, being formed with various filaments or fibers and having void spaces between adjacent filaments or fibers. Such void spaces may exhibit properties that facilitate boney ingrowth. For example, non-woven fibrous implants may be formed from extrudate material continuously ejected from an orifice or die as a filament or fiber. In some embodiments, the extrudate material may be lapped in a recurring pattern and in other embodiments, the extrudate material may be extruded in an environment having a turbulent air flow resulting in a randomly formed extruded component. For example, the ejected fiber may be lapped and/or entangled such that in cross section the fibrous implant is composed of randomly spaced and oriented fibers defining porous spaces between adjacent filaments or fibers. The fibers may have any cross sectional shape, such as a circular cross sectional shape, I or H cross sectional shapes, etc. as may be determined by the shape of the exit orifice or die.

Exemplary use cases, methods of manufacture, and corresponding illustrations thereof are not meant to be limiting, such as limiting the shape or size of the subject interbody implants 10000, 11000, 12000 unless otherwise described expressly in this specification or appended claims.

Exemplary non-woven fibrous implants 10000, 11000, 12000 may be used to correct a spacing between adjacent vertebrae of a patient's spine and/or alignment of a patient's spine in the coronal or sagittal plane, for example. In some embodiments, a target alignment may be predetermined by data parsing performed by controller 1050 in coordination with scanning data, navigation equipment 1095, CT-Images, etc. which may assess a patients current spinal alignment and calculate a target alignment. For example, exemplary embodiments may include a robotic subsystem having robotics equipment 1030 including scanning and imaging equipment configured to scan a patient's anatomy.

Referring generally to FIG. 54-FIG. 61B exemplary system hardware, non-woven fibrous implants, and methods of manufacture are disclosed. FIG. 54 shows example system hardware that may be used concurrently with disclosed additive-manufacturing systems (see FIG. 10) and utilized to form disclosed non-woven fibrous implants 10000, 11000, and 12000. In at least one embodiment, robotic arm 40 may put base material(s) into hopper 31 of extruder 30 where the base material(s) may be mixed and warmed and extruded through nozzle 32. The extrudate passing through nozzle 32 may be routed and/or pumped to dispensing component 110 by piping (not illustrated). Air supply source 50 may be a canister of compressed air, an air compressor, a blower, or the like for example. Air supply source 50 may contain pressurized atmospheric air or noble gases and may be used for a variety of purposes as will be explained in more detail below. Moreover, extruder 30, robotic arm 40, and air supply source 50 may all be controlled by controller 1050. Additionally, embodiments including particular materials extruded from extruder 30 may also be printed by dispensing component 110 and vice versa. In some embodiments, extruder 30 may be configured to extrude at least one material and/or mix a plurality of separately stored materials at a mixing component or mixing portion proximate the dispensing tip (not illustrated). The extrudate of extruder 30 may be conveyed to dispensing component 110 by any known conveyance means, e.g., piping, tubing, conveyor belts, etc.

The controller apparatus 1050 may include a processor and a non-transitory computer-readable medium. The controller 1050 may be configured to control the robotics equipment 1030 including the various scanning and imaging equipment to determine a target alignment of a patients spine, and develop an additive-manufactured printing plan (or additive-manufactured printing instructions) including an additive-manufactured material selection plan that may include or form at least one portion including at least one fibrous material. In some embodiments, the additive-manufactured printing plan may be based on the target alignment of the patient's spine, and an interbody access space which may only partially provide access to a disc space between adjacent vertebra of the patients spine. In some embodiments, the additive-manufactured material selection plan may be based on the design criteria of the particular implant, e.g., some implants and surgical situations may benefit from a substantially rigid implant whereas others may benefit from a highly flexible implant imparting cushioning benefits and a relatively greater range of motion. For example still, some implants may benefit from including non-woven fibrous portions that may accelerate or facilitate boney ingrowth between pores or void spaces between adjacent fibers. Controller 1050 may execute the additive-manufactured printing plan to thereby control the extruder 30, robotic arm 40, air supply source 50, dispensing component 110, armature 112, etc. to dispense at least one printing material to form at least one non-woven fibrous implant. For example, controller 1050 may send a control signal to an actuator associated with each of the aforementioned devices.

Additive-manufactured non-woven fibrous implants may be printed or formed from a variety of materials, and combinations of materials. The materials listed herein are not exhaustive, nor are they meant to be limiting, and should be considered as exemplary in nature. For example, some materials may be substituted for other materials, especially when the substitution is with a material having the same or substantially the same material properties and/or an alternate formation that is optimized for 3-D printing and/or extrusion technologies. The following is an exemplary listing of potential materials that may be printed by disclosed additive manufacturing systems via, e.g., dispensing component 110 and/or extruder 30. It shall be understood that disclosed additive manufacturing techniques may include materials that pass through extruder 30 in addition to, or as an alternative to, materials that are directly printed by dispensing component 110 without passing through extruder 30.

Example base materials that may be feed through extruder 30 and selectively dispensed by dispensing component 110 may be plastics and nylons which may be mixed with metallic materials such as stainless steel, nitinol, titanium, etc. In at least one embodiment, polyetheretherketone (PEEK) may be fed to extruder 30 at hopper 32 by robotic arm 40. PEEK may be considered a high-performance engineering plastic with outstanding resistance to harsh chemicals, and excellent mechanical strength and dimensional stability while also being biocompatible. In at least one embodiment, metallic particles may be mixed with a PEEK material and extruded with a binding agent that may allow for the material to be sintered into a solid piece. In other embodiments, PEEK material may be mixed with calcium particles, phosphate particles, and/or other BGMs.

Other example printing materials that may be dispensed by dispensing component 110 may be polymethylmethacrylate (PMMA), commonly referred to as acrylic. PMMA may be considered a rigid polymer having a material stiffness substantially similar to bone (or at least having a material stiffness within the range of cancellous bone to cortical bone). For example, PMMA may have a modulus of elasticity of about 3 GPa which falls within the range of the modulus of elasticity of cancellous bone to cortical bone, about 0.3 GPa-20 GPa. PMMA may be capable of curing in place at relatively low temperatures making it an ideal material for in-situ printing in a patient's body. PMMA may be considered a relatively brittle polymer having a low fracture strain on the order of 1%-3% while also being a suitable material in compression and generally suitable as a filler material.

Another printing material selectively dispensed by dispensing component 110 may be and or include epoxies. Epoxies may be used as an adhesive to join separable components of disclosed implants and/or adhere disclosed implants to relevant anatomical features such as, e.g., vertebrae. Epoxies may be cured in place as a single part epoxy or as a two part epoxy including a substrate material and a curing material that are mixed together at a mixing portion of dispensing component 110. Some epoxies may cure under ultraviolet light (UV) and be advantageous in the target field because of a relatively low curing temperature. Generally, epoxies may form high quality bonds with other disclosed materials, e.g., rigid materials such as PMMA and may therefore be used to couple relevant components of disclosed implants.

Another printing material selectively dispensed by dispensing component 110 may be and/or include polytetrafluoroethylene (PTFE). At least one advantage of PTFE is that is considered a highly inert material that is chemically stable and therefore poses a relatively low risk of causing biological complications such as a host rejecting the material. PTFE may include a porous structure that may facilitate bony ingrowth therebetween the pores. Another printing material selectively dispensed by dispensing component 110 may be and or include silicone. Silicone may be considered a relatively soft elastomeric material (rubber like material) having a relatively low modulus of elasticity at about 0.05 GPa. Silicone is capable of curing in place at a relatively low temperature making it an advantageous material for in-situ printing in a patient's body. Silicone is also generally considered a highly inert material that is chemically stable and therefore poses a relatively low risk of causing biological complications such as a host rejecting the material.

Another printing material selectively dispensed by dispensing component 110 may be and or include polyurethanes. Polyurethane may be produced in many various compositions having a wide range of mechanical properties varying from pliable (soft) to rigid (hard). In at least one embodiment, a first polyurethane composition is applied as a type of cure in place compressible foam which may be suitable as a filler type material which may have material properties substantially similar to bone structures, e.g., cancellous bone. In an alternate embodiment, a second polyurethane composition is formed for a rigid application having material properties substantially similar to bone structures, e.g., cortical bone. Another printing material selectively dispensed by dispensing component 110 may be and or include Polylactic acid (PLA). PLA may be a biodegradable polymer, a special class of polymer that decomposes after its intended purpose into natural byproducts such as water, biomass, inorganic salts, carbon dioxide, and nitrogen.

In some embodiments, controller 1050 may include proprietary software, such as, for example, a modified version and/or updated version of Medtronic's Mazur software platform, for analyzing and pre-operatively defining a geometry within a disc space of a patient. For example, controller 1050 may utilize the Mazur software in coordination with X-Ray Images and/or CT-Images and/or MRI Images which may be further processed to develop a three dimensional model of the disc space of the patient. In at least one embodiment, the controller 1050 generates a plan for the final three-dimensional geometry of a completed non-woven fibrous implant and/or a composite non-woven fibrous implant. The final three-dimensional geometry of the completed non-woven fibrous implant(s) may be broken down into various segments or portions by the controller 1050; and each portion may later be coupled or bonded together by epoxies or other bonding agents and/or other mechanical fasteners. For example, a completed non-woven fibrous implant may be formed in various sections where each section is formed of an alternate material having different material properties that are later coupled together by epoxy or a mechanical fastener. In this way, the controller 1050 may develop an additive manufactured printing plan that includes an additive-manufactured material selection plan including instructions to form a non-woven fibrous portion or select a non-woven fibrous portion from stock material. After the controller, 1050 has developed the additive manufactured printing plan (which may include an additive-manufactured material selection plan) the controller 1050 may control printing of the various segments or components as individual portions that may later be coupled in-situ, as will be explained in further detail below.

In some embodiments, controller 1050 may determine a surgical sequence and/or installation sequence for printing and/or installing at least a portion of a composite non-woven fibrous implant in-situ based on the target alignment of a patient's spine. Additionally, in some embodiments a composite non-woven fibrous implant may also have motion-sparing properties, i.e., include a pliable material configured to dampen shock to the implant and/or transfer shock between adjacent vertebrae. In some embodiments, controller 1050 may determine multiple portions having different material compositions are necessary. For example, the installation sequence may involve manipulating, repositioning or otherwise coupling at least one portion to another portion before or during placement of a composite additive manufactured non-woven fibrous implant in the disc space of a patient. Controller 1050 may also determine that multiple composite additive manufactured non-woven fibrous implants having different shapes such as discs, wedges, etc. should be printed.

Figure 55B:
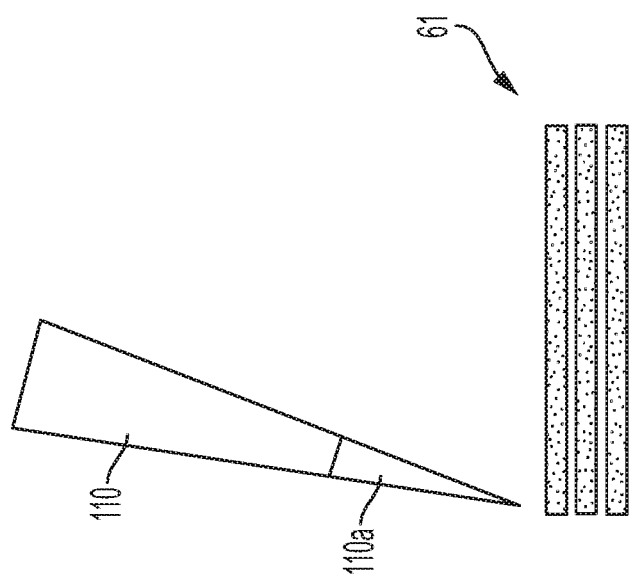
FIG. 55B shows the deposition of a final material layer to form a unitary implant.
Figure 55A:
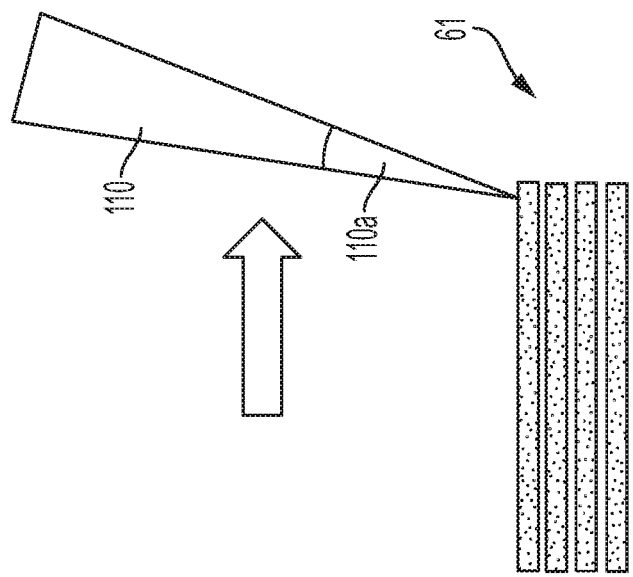
FIG. 55A shows the deposition of a plurality of material layers.

FIGS. 55A and 55B show the deposition of a plurality of material layers 61. In the example embodiment, dispensing component 110 may include an interchangeable dispensing nozzle portion 110a that functions as an exit orifice controlling the cross sectional shape and/or diameter of extruded material. As explained previously, downstream pumps, e.g., pumps 1040, may control a flow rate of extruded or printed material. FIG. 55A may show three layers of consistently formed uniform layers of material 61. Each layer of the uniform layers of material 61 may be PEEK material or a PEEK composite that is ejected through nozzle portion 110a in a hot liquid state. Each subsequent layer of the uniform layers of material 61 may be printed by moving dispensing component 110 from left to right (shown by right facing arrow in FIG. 55B). The rate of deposition/printing and movement of dispensing component 110 may be controlled by controller 1050 such that each layer of the uniform layers of material 61 is deposited on the immediately prior layer of the uniform layers of material 61 after the immediately prior layer has sufficiently cooled and solidified. For example, the immediately prior layer may have solidified, at least partly, before deposition/printing of the next layer of uniform layers of material 61 in an organized manner. For example, controller 1050 may control a flow rate of material via pumps, e.g., pumps 1040 as previously explained. In some embodiments according to this 3D printing technique, each layer of uniform layers of material 61 is layered in such a way as to form a unibody piece and/or unibody implant. In some embodiments according to this printing technique, uniform material layers 61 may form a unibody piece that may be used as a mat 70 (see FIG. 56) that may form at least a portion of an additive-manufactured non-woven fibrous implant and/or a composite additive-manufactured non-woven fibrous implant. In some embodiments, the uniform layers 61 may be composed of a single long continuous fiber or may be composed from a single continuous extrusion process that forms discrete or broken fibers. In other embodiments, uniform layers 61 may be a plurality of discrete fibers and/or relatively short fibers. In those embodiments, the length of the fibers may be controlled by controller 1050 activating and stopping pumps 1040 and/or extruder 40 at timed intervals. In other embodiments, a cutting blade or the like may cut the extrudate material 60 as it is continuously ejected to form a plurality of fibers of the same or different lengths. For example, robotic arm 40 may be configured with a cutting blade and be controlled by controller 1050 to cut the extrudate material 60 at regularly timed intervals or random intervals leading to a plurality of fibers forming layer 61.

Figure 56A:
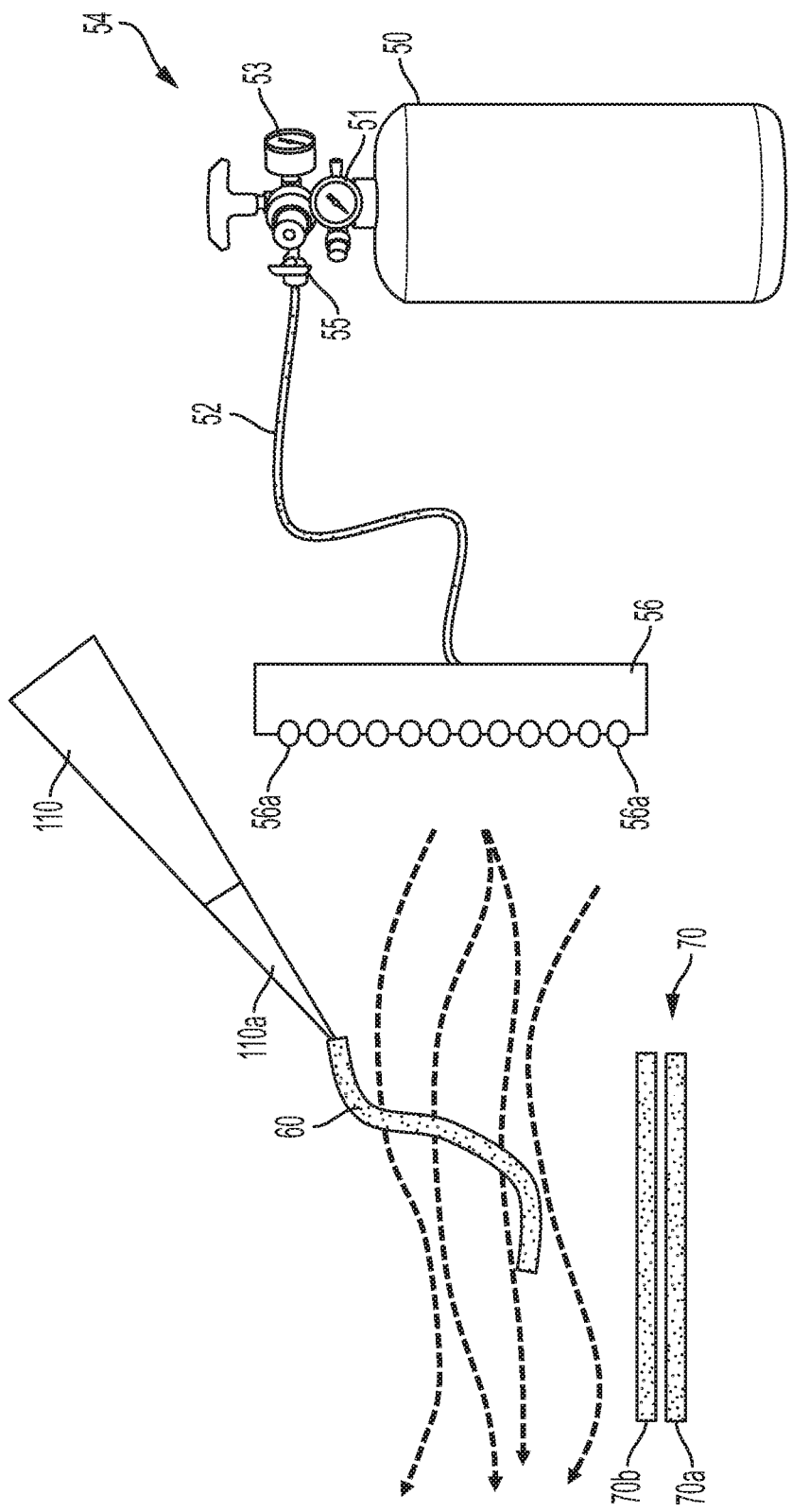
FIG. 56A shows a lateral view of the initial forming stages of an additive-manufactured non-woven fibrous implant.

FIG. 56A shows a lateral view of the initial forming stages of an additive-manufactured non-woven fibrous implant. In the disclosed embodiment, a mat 70 including a first material layer 70a and a second material layer 70b is initially formed.

The mat 70 may be formed of any of the aforementioned materials. In some embodiments, a relatively large mat 70 is formed in advance and cut to a particular size best suited to a patient's particular anatomy according to previously disclosed data parsing techniques and printing plans performed by controller 1050. In the disclosed embodiment, dispensing component 110 is outfitted with an interchangeable dispensing nozzle 110a by robotic armature 40. The dispensing nozzle 110a may be configured to continuously eject printing material or extrudate 60 as a filament or fiber at a specific flow rate which may be determined by provisioning components and/or pumps 1040 as previously explained. Dispensing nozzle 110a may dispense a relatively thin extrudate 60 having a circular cross section. Other nozzles 110a (not illustrated) may dispense extrudate with other cross sectional shapes, for example, oval shaped, partly oval shaped, H shaped, I shaped, and etc. In some embodiments, nozzles 110a may have a cross sectional shape similar to a star or a circle with an indent or outdent on an outer surface thereof for tearing small amounts of material and/or roughening an outside surface of the extruded material. At least one advantage of tearing a side surface of the extruded fiber is to increase surface area of the extruded filament which may further encourage bone ingrowth and/or contribute to further opening porous spaces between adjacent fibers. Controller 1050 may determine what type of nozzle 110a to utilize according to an additive-manufactured printing plan and direct or control robotic armature 40 to select a specific nozzle 110a from a plurality of differently shaped and sized nozzles 110a, i.e., a set of distinct nozzles 110a having varying cross sectional exit orifices as is consistent with this disclosure.

As the extrudate 60 exits nozzle 110a, a fluid flow (shown by dashed lines and arrows) interacts with extrudate 60 before extrudate 60 falls to matt 70. Extrudate 60 may fall to matt 70 at least partly due to gravity, extraction forces, and/or suction forces as will be explained in more detail below. Fluid forces may be due to gases and/or liquids. Matt 70 may be formed of or include PMMA, PTFE, polyurethanes, and even other biocompatible metallic materials having a modulus of elasticity generally within the range of boney structures as explained hereinabove. However, it shall be understood that matt 70 shall not be limited to the specific materials and/or shapes disclosed herein.

In the disclosed embodiment, air supply source 50 may be configured to supply a turbulent airflow adjacent the location where extrudate 60 exits nozzle 110a. For example, air supply source 50 may supply a turbulent airflow in the region between matt 70 and nozzle 110a such that as extrudate 60 exits nozzle 110a it is subjected to the randomized flow pattern of a turbulent fluid flow (as opposed to a laminar fluid flow). Turbulent fluid flow is intended to have its ordinary technical meaning as a type of fluid (gas or liquid) flow in which the fluid undergoes irregular fluctuations, or mixing. Turbulent flow may refer to the speed of the fluid at a point or region that is continuously undergoing changes in both magnitude and direction. Conversely, laminar flow may refer to fluid motion in smooth paths or layers.

Figure 56B:
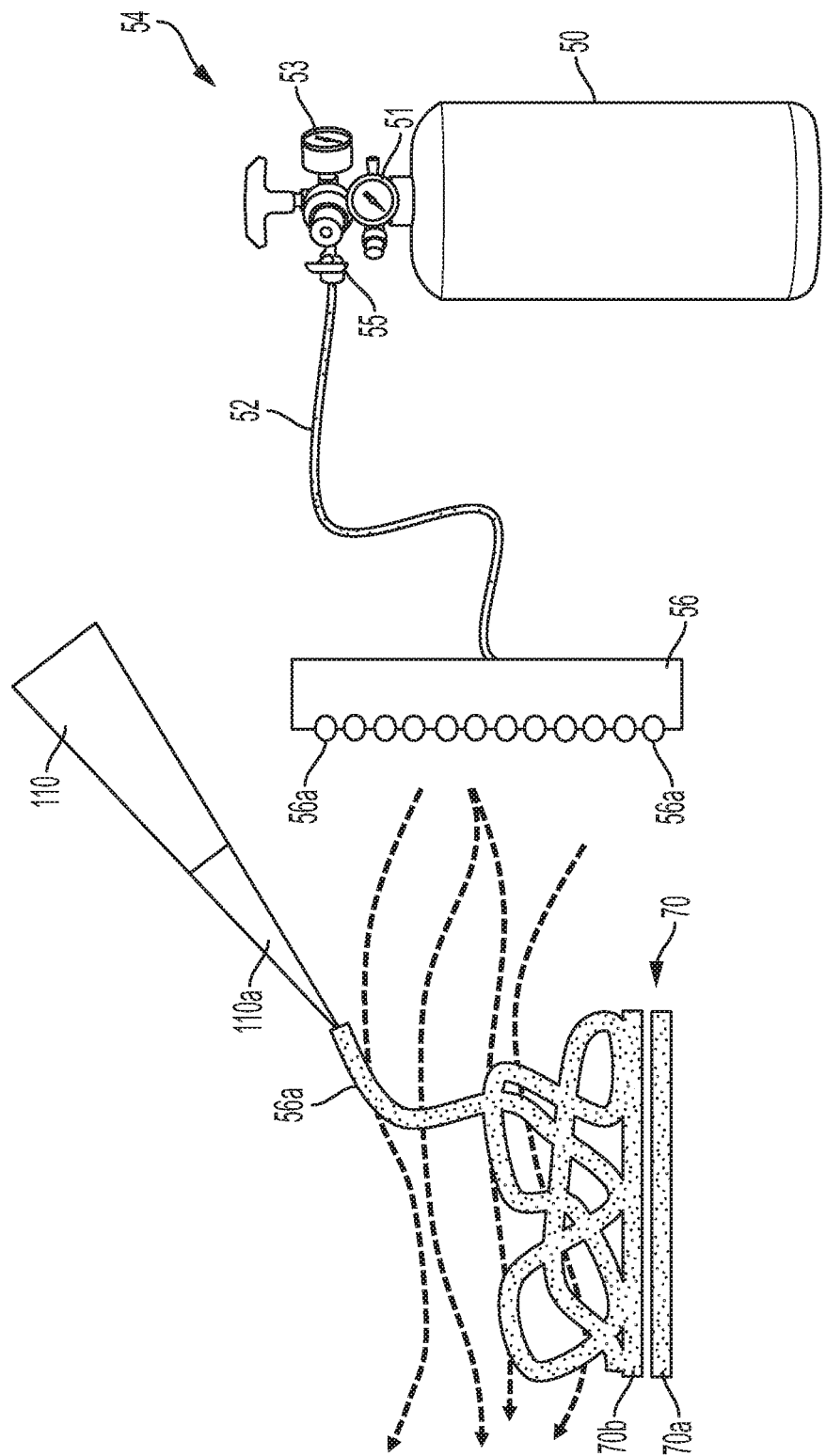
FIG. 56B shows a lateral view of the intermediate forming stages of an additive-manufactured non-woven fibrous implant.

It shall be understood that the embodiment of FIG. 56A and FIG. 56B is exemplary in nature and that although it illustrates extrudate 60 pooling on matt 70 in a generally bottom to top (up and down) direction extrudate 60 may pool on matt 70 differently in other embodiments. For example, extrudate 60 may be pushed against a vertical wall portion first due to fluid force from air supply source 50 (not illustrated). For example, a fluid force from air supply source 50 may push extrudate 60 against a perimeter portion first and thereafter, an interior portion inside of the perimeter portion may be infilled. Additionally, in some embodiments, extrudate 60 may pool on matt 70 in columnar fashion. For example, extrudate 60 may be ejected from nozzle 110a to form a first top to bottom column, a second top to bottom column adjacent the first column, and a third top to bottom column adjacent the first column and second column to complete the extrusion process (not illustrated). At least one advantage of forming a plurality of discrete columns is that each column may have a different fiber density and/or material composition and therefore exhibit different mechanical properties. For example, outermost columns may exhibit a relatively high fiber density of a first material composition and interior columns may exhibit a relatively low fiber density of a second material composition. This may lead to some non-woven fibrous implants and/or non-woven fibrous components having dense hard outer surface and flexible or pliable interior surfaces.

In some embodiments, matt 70 may take the form of a radial surface, a conical surface, or a mandrel. In at least one embodiment, matt 70 is a radial disc that is continuously rotated ontop of a turntable while extrudate 60 exits nozzle 110a. In this embodiment, the extrudate 60 may form a radial pattern. Similarly, nozzle 110a may be configured to rotate from an outermost radial edge of a circular matt 70 towards an innermost radial center of the circular matt 70 to achieve a similar effect. For example, disclosed embodiments may form a fibrous non-woven implant that is built of radially aligned fibers as opposed to linearly aligned fibers. In some embodiments as well, the extrudate 60 may be extruded onto the cylindrical surface of a cylindrical matt and built out radially, thereby increasing the overall radius of the device In the disclosed embodiment, air supply source 50 may be a container of compressed air or an air compressor, for example. However, other embodiments may utilize high velocity fans and/or blowers provided that the fluid flow type adjacent the nozzle 110a is of a turbulent flow type. Air supply source 50 may include a pressure gauge 51, fluid conveying lines 52, a temperature gauge 53, an actuator 54, an output flow valve 55, and a manifold 56. In the illustrated embodiment, manifold 56 is a relatively long rectangular manifold with a plurality of manifold exit orifices 56a. In some embodiments, utilizing a plurality of differently and/or spaced dimensioned exit orifices 56a may contribute to the turbulent nature of the airflow. Controller 1050 may control air supply source 50 via actuator 54 which may be configured to adjust and open/close output flow valve 55. Controller 1050 may also receive information in real time pertaining to the pressure gauge 51 and temperature gauge 53, which may be used for fluid dynamics calculations in addition to geometrical properties of the fluid conveying lines 52 and manifold 56. Controller 1050 may use the aforementioned data points to calculate an appropriate airflow type, e.g., to ensure that the airflow type remains turbulent while concurrently ejecting extrudate 60 from nozzle 110a.

In the illustrated embodiment, controller 1050 may have determined to open output flow valve 55 via actuator 54 to a first position, which will produce a turbulent airflow downstream manifold 56. As time progresses, and the internal pressure of air supply source 50 begins to drop, controller 1050 may receive feedback in real-time from pressure gauge 51 and further open or close output flow valve 55 to ensure that the airflow type remains turbulent. In this way, controller 1050 may be understood as controlling air supply source 50 to continuously provide a turbulent airflow type throughout the deposition/printing process. In at least one embodiment, controller 1050 may vary the airflow to be highly turbulent for denser extrudate and decrease the airflow, at least relatively, for less dense extrudate.

At least one advantage of subjecting extrudate 60 to a turbulent airflow is that the extrudate 60 may be subjected to forces of randomized direction and magnitude causing extrudate 60 to form on matt 70 in an irregular and/or inconsistent way. For example, as shown in FIG. 56B, extrudate 60 may be continuously ejected from nozzle 110*a* at a continuous flow rate into a turbulent airflow path leading to the extrudate 60 having a random, irregular orientation and/or irregular formation on matt 70. In some embodiments, the extrudate 60 may become entangled with itself, and/or if the extrudate 60 is warm enough extrudate 60 may bond to itself. Additionally, in some embodiments extrudate 60 may be extruded at a precise but sufficiently high enough temperature that extrudate 60 becomes (1) entangled with itself in an irregular formation portion and (2) bonds to itself (at least partly) at previously ejected portions. In some embodiments, extrudate 60 may become entangled in a birds nest like pattern. In other embodiments, the extrudate 60 may be dispensed to form even continuous patterns. In those embodiments of even continuous patterns a turbulent airflow may not be applied to the extrudate 60. The extrudate 60 may cool, cure, and/or otherwise harden in an entangled irregularly oriented pattern on matt 70. The entangled irregularly oriented pattern may define irregularly sized and disposed void spaces or pores between adjacent sections of extrudate 60 hence forming an additive manufactured non-woven fibrous component.

Additionally, as is consistent with the disclosure herein, the turbulent fluid may be maintained at any temperature that is beneficial to building the implant. For example, the turbulent fluid may relatively cooler than the extrudate material 60 leading to extrudate material 60 hardening relatively quickly or the turbulent fluid may be relatively warmer than the extrudate material 60 leading to extrudate material 60 maintaining workability and being able to bond back to itself. At least one advantage of utilizing a relatively cooler turbulent fluid may be that the cooler temperature may induce stress to the extrudate material 60 and increase its strength in an analogous way to cold forged materials. At least one advantage of utilizing a relatively warmer turbulent fluid may be that the warmer temperature causes the extrudate material 60 to maintain its workability and bond back to itself in a relatively denser fiber formation. In some embodiments, a warm fluid flow is directed on to an already pooled portion of extrudate material 60 to increase its workability and therefore naturally compacting the extrudate material 60 in a denser configuration due to gravity forces and increased workability of the extrudate material 60. At least one advantage of warming extrudate material 60 via a warm fluid flow may be the formation of a more cohesive implant with relatively smaller void spaces between adjacent fibers.

Figure 57:
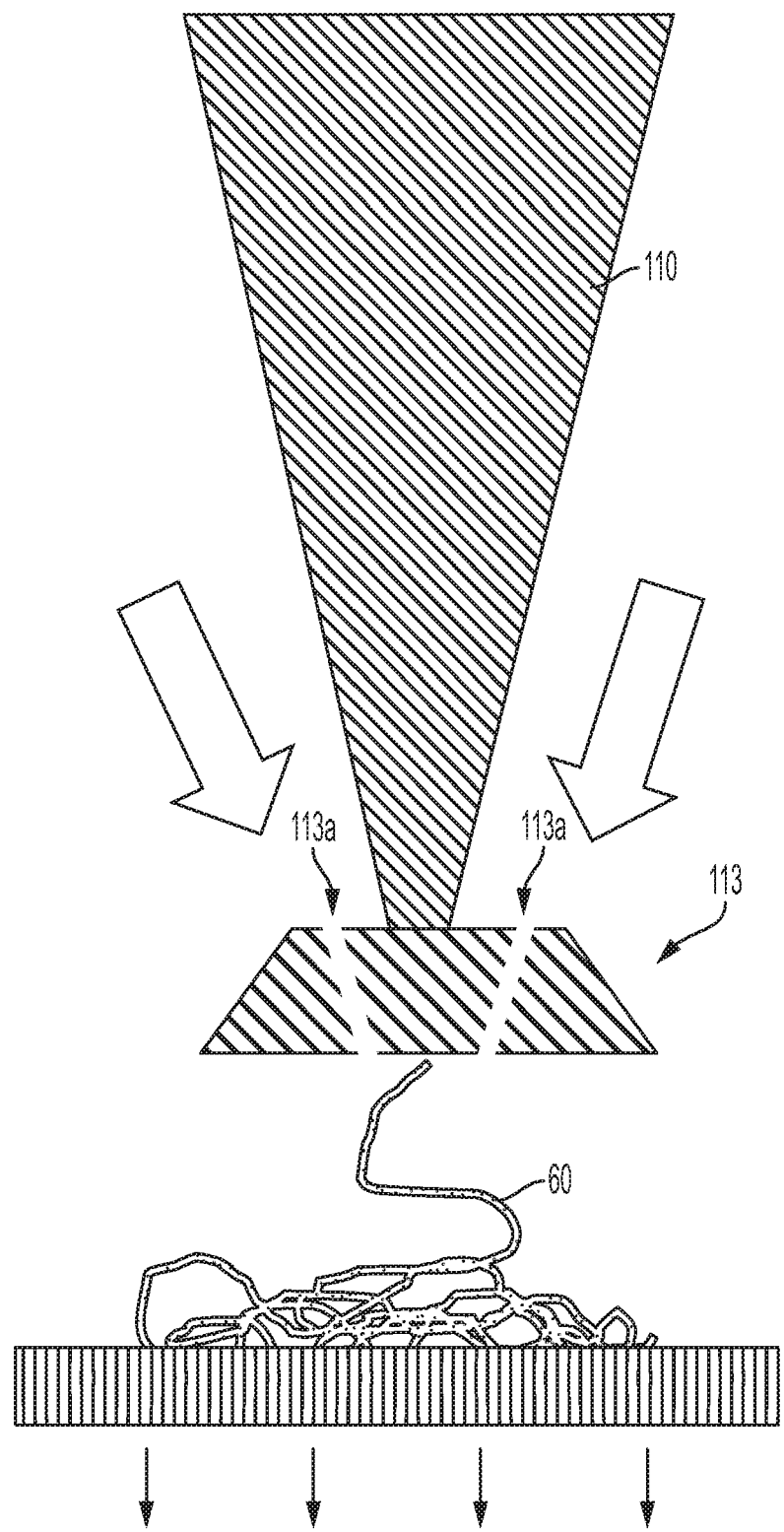
FIG. 57 shows a schematic view of an example die including an airflow path and a collection plate for collecting extruded fibrous material for forming an additive-manufactured non-woven fibrous implant.

FIG. 57 may show a schematic view of an example die 113 including at least one airflow path 113*a* and a collection plate 114 for collecting extruded fibrous material for forming an additive-manufactured non-woven fibrous implant. In the disclosed embodiment, dispensing component 110 and die 113 may be configured to eject extrudate material 60 as previously explained but the die 113 may integrally include at least one airflow path 113*a* proximate to the ejection location where extrudate 60 is ejected. Although FIG. 57 does not illustrate air supply source 50 those with skill in the art will readily appreciate that die 113 may be connected to air supply source 50 via fluid conveying lines 52. FIG. 57 illustrates an airflow being applied to die 113 schematically by diagonal downward arrows on opposite sides of dispensing component 110. At least one advantage of die 113 including at least one integral airflow path 113*a* is that the turbulent airflow may be more easily controlled and exhibit highly turbulent flow in a region directly adjacent the ejection location where extrudate 60 is ejected. Additionally, in some embodiments, collection plate 114 may be configured to include a plurality of orifices that may be connected to a vacuum, or air conveyance system configured to suck air from the top of collection plate 114 (where extrudate material 60 is formed/collected) to the other side of collection plate 114 (represented by downward arrows directly beneath collection plate 114). At least one advantage of dispensing extrudate 60 on a suctioned collection plate 114 may be that the extrudate material 60 may be packed more densely compared to a non-suctioned collection plate 114. For example, due to the suction force pulling the extrudate material 60 downward the extrudate material 60 may consolidate. An additional advantage is that the suction force may cool the extrudate material 60 relatively quickly due to the increased airflow. In some embodiments, the collection plate 114 may be configured to unevenly apply a suction force leading to portions of the extrudate material 60 cooling before other portions and or consolidating more densely than other portions. Although a single die 113 is illustrated in FIG. 57, some embodiments may include more than one die 113 including the same, substantially the same, or similar components and functionality. For example, a pair of die 113 may each be configured for extrusion at the same time in substantially the same region. Additionally, when more than one die is used at the same time, each die 113 may be configured to extrude the same material at the same thickness/cross-sectional size, the same material at a different thickness/cross-sectional size, a different material, at the same thickness/cross-sectional size, and/or a different material at a different thickness/cross-sectional size.

Figure 58:
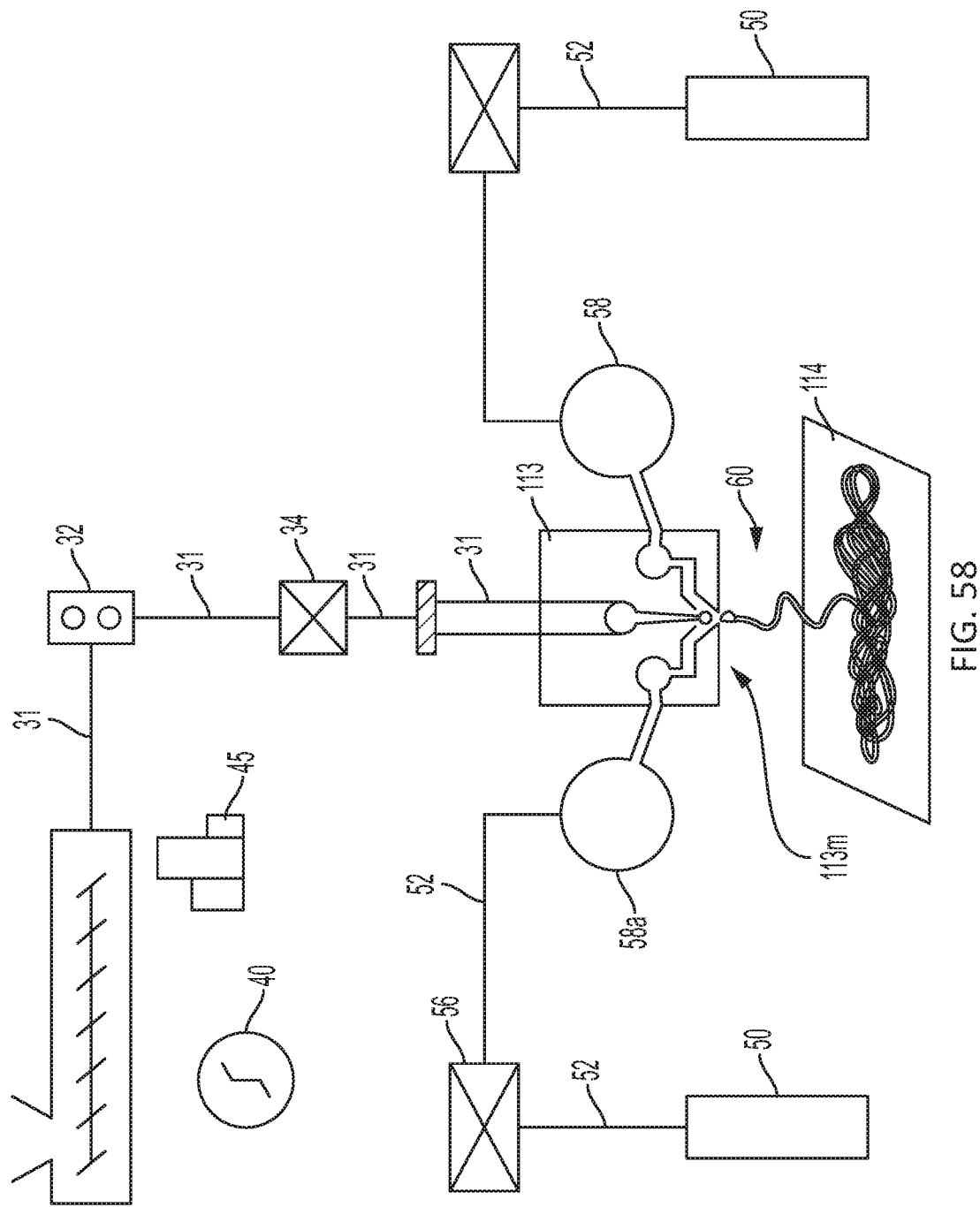
FIG. 58 shows an example schematic of system hardware for use with disclosed additive manufacturing systems.

FIG. 58 shows an example schematic of system hardware for use with disclosed additive manufacturing systems. In the schematic drawing, an extruder 30 may be supplied with base material 45 by robotic armature 40. Extruder 30 may provide extrudate material through extrudate conveying lines 31 to a pump 32 which may also facilitate the conveyance of extrudate material through conveying lines 31. A heater 34 may optionally be used to keep the extrudate material at a sufficiently hot enough temperature that it remains in liquid form. Additionally, a filter 46 may filter the extrudate material to improve its quality and/or ensure that extrudate material will seamlessly pass through die 113. Die 113 may be attached to dispensing component 110 and/or armature 112. In some embodiments, positioning of die 113 may be controlled by robotic armature 40. Moreover, controller 1050 may control an extrusion rate of extruder 30, a pumping rate of pump 32, and a heating temperate of heater 34. In this way, controller 1050 may control a flow rate and temperature of extrudate material. Additionally, controller 1050 may control robotic armature 40 and/or armature 112 to position die 113 in a desired location. Similarly, controller 1050 may control robotic armature 40 to select a particular material from stock material 45 according to a pre-establish additive manufacturing printing plan including instructions to form a non-woven fibrous implant.

FIG. 58 may also illustrate at least one air supply source 50. Although two air supply sources 50 are illustrated, those with skill in the art will readily appreciate that a single air supply source 50 may also be sufficient. Air supply source

50 may be connected to fluid conveying lines 52 and air supply heater 56. Air supply heater 56 may heat the fluid contained in fluid conveying lines 52 and may also include additional inline blowers, fans, manifolds etc. to increase the turbulence of the fluid within fluid conveying lines 52. Fluid conveying lines 52 may in turn be connected to manifold 58. At least one advantage of manifold 58 is that it may assist in distributing or throttling the fluid pressure before fluid enters die 113. In some embodiments, manifold 58 is designed to increase the turbulence of the fluid from air supply source 50. Die 113 may include an injection portion 113m where the flow path of the extrudate material and the flow path of the fluid from air supply source 50 coincide. Similar to previous embodiments, the flow path of the fluid may be considered turbulent at the injection portion 113m and/or just beneath the injection portion 113m where the extrudate material 60 exits the die 113. The extrudate material 60 is subjected to a turbulent airflow and the turbulent airflow causes the extrudate material to unevenly deposit on substrate 114 in an entangled irregularly oriented pattern. Substrate 114 may be a collection plate 113 with or without suction functionality as previously explained or collection plate 113 may resemble matt 70 as previously explained. In at least some embodiments, substrate 114 may be relatively large and armature 112 or robotic arm 40 may additionally move die 113 (left/right and forward/backward) to create a relatively large layer of non-woven fibrous material having a substantially consistent height. Moreover, controller 1050 may control the movement of the die 113 to form a relatively large layer of non-woven fibrous material having a substantially consistent height.

Figure 59A:
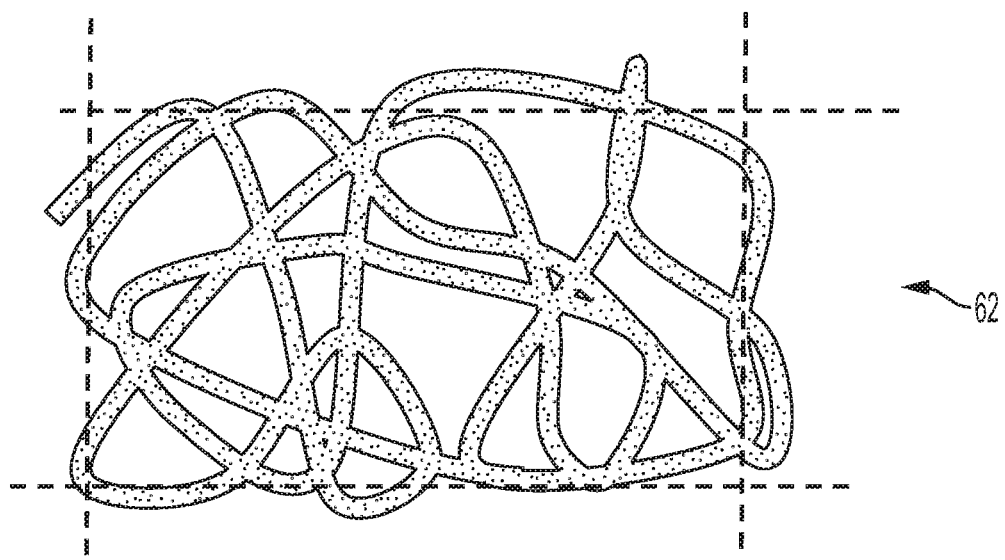
FIG. 59A shows an intermediate processing step of a batch of fibrous material for use with disclosed additive-manufactured non-woven fibrous implants.

FIG. 59A shows an intermediate processing step of a batch of fibrous material 62 for use, for example, with disclosed additive-manufactured non-woven fibrous implants. In the disclosed embodiment, a batch of fibrous material 62 may have been formed on substrate 114 as a relatively large layer of non-woven fibrous material having a substantially consistent height as previously disclosed. The batch of fibrous material 62, may be machined to predetermined sizes by any known machining or processing technique. For example, batch of fibrous material 62 may be cut length wise at cuts $C_1$ and $C_2$ and width wise at cuts $C_3$ and $C_4$. In some embodiments, a plurality of different batches of fibrous material 62 may be formed in advance of surgery and stored in an accessible area to robotic armature 40. For example, a first batch of fibrous material may be formed of a first material such as PEEK and have a first fiber density and a second batch of fibrous material may be formed of a second material composite including PEEK and at least one metallic element impregnated in the extrudate fibers at a second fiber density greater than the first fiber density. In some embodiments, robotic armature 40 may perform the previously disclosed cutting steps and in others an end user may perform the cutting previously disclosed cutting steps. In some embodiments, the batch of fibrous material 62 may be sanded for smoothness or scratched for increased roughness, or dipped in an acid or etching material to increase roughness and surface area. The batch of fibrous material 62 may sprayed and/or coated with another material to increase its rigidity if desired. Furthermore, the batch of fibrous material 62 may be subjected to additional heat further melting the fibers together to increase the adhesion between adjacent fibers and/or to smooth out edges of the batch of fibrous material 62. In some embodiments, the edges of the batch of fibrous material 62 may be dipped into melted plastic to form a cap around the batch of fibrous material 62. Likewise, the batch of fibrous material 62 may subjected to further chemical processing to etch portions of the fibrous material 62 and thereby increase a porosity of fibrous material due to the etching process. Additionally, in some embodiments the batch of fibrous material 62 may be warmed and insert into a press to adjust and/or increase the density of the batch of fibrous material 62. Similarly, a second batch of fibrous material 62 may be overlaid on top of a first batch of fibrous material 62 and the first and second batches may be warmed and insert into a press to further force tangling and/or bonding between the first and second batches of fibrous material 62.

At least one process for increasing a toughness of non-woven fibrous batches 63 may include a machining process that inserts pins and/or blades intro extruded material 60 to mechanically tangle extrudate material 60 with itself. In those embodiments utilizing mechanical means to tangle extrudate material 60 with itself robotic arm 40 may be configured with a rod, pin, or blade and continuously turn extrudate material 60 as it pools. Similarly, robotic arm 40 may utilize a rod, pin, or blade to push through already pooled and/or hardened extrudate material 60. At least one advantage of mechanically manipulating extrudate material 60 in this way is the promotion of "cross-linking" and the further separation or breaking of extrudate material 60 into additional non-continuous fibers which may increase the random entanglement of the fibers of the final non-woven fibrous component.

Additionally, controller 1050 may analyze batches of fibrous material 62 after formation with disclosed scanning equipment and store relevant data pertaining to as built specifications of the material properties of each batch of fibrous material 62. For example, controller 1050 may use the scanning and imaging equipment to assess the as-built density and porosity of the batch of fibrous material 62 and store relevant information regarding the batch of fibrous material 62 for later use with other disclosed embodiments.

Figure 59B:
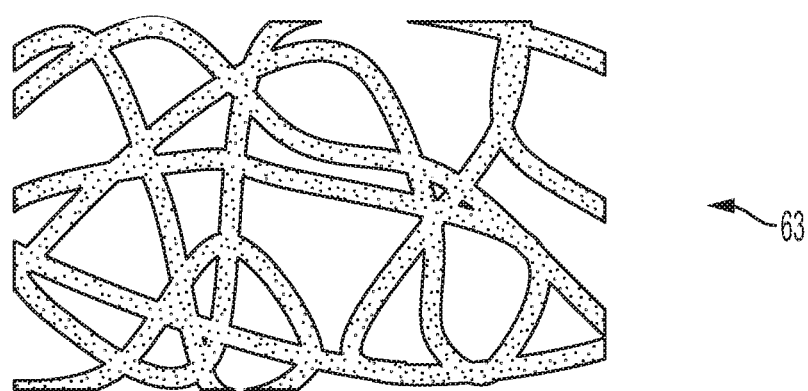
FIG. 59B shows a processed batch of fibrous material for use with disclosed additive-manufactured non-woven fibrous implants.

FIG. 59B shows a processed batch of fibrous material 62 of FIG. 59A after being formed into a non-woven fibrous component 63 for use with disclosed additive-manufactured non-woven fibrous implants. At least one advantage of forming non-woven fibrous component 63 is that non-woven fibrous component 63 may be installing in between vertebrae of a patient and additional material may be printed or formed around non-woven fibrous component 63 in-situ to form a composite non-woven fibrous implant including at least a portion that is formed in-situ.

Figure 60A:
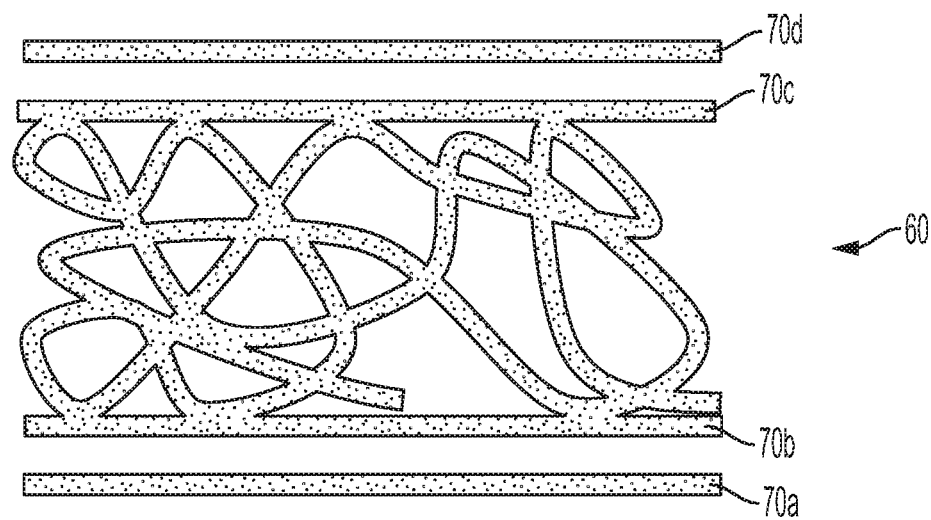
FIG. 60A shows a lateral view of the intermediate forming stages of an additive-manufactured non-woven fibrous implant.
Figure 60B:
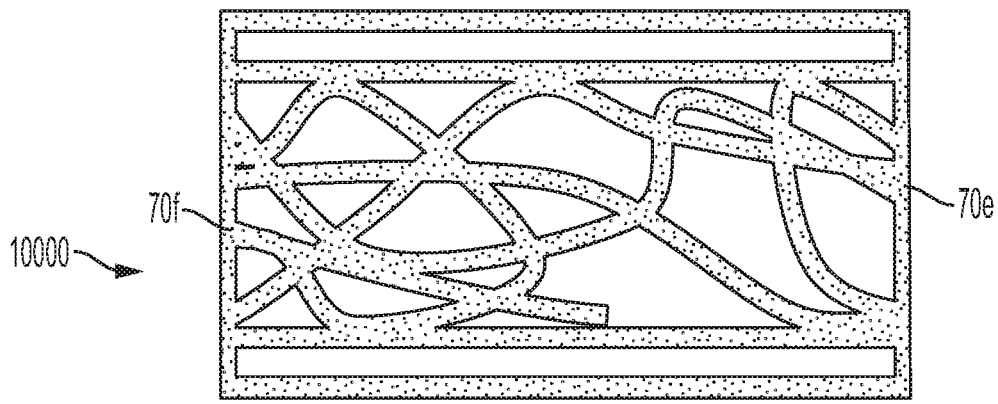
FIG. 60B shows a lateral view of the final forming stages of an additive-manufactured non-woven fibrous implant.

FIGS. 60A and 60B may show a lateral view of an intermediate forming stage and a final forming stage, respectively, of an additive-manufactured non-woven fibrous implant 10000. Non-woven fibrous implant 10000 may include extrudate material 60 formed according to previously disclosed manufacturing methods. In some embodiments, the extrudate material 60 may correspond to and/or be previously disclosed non-woven fibrous component 63. In the disclosed embodiment, extrudate material 60 may be formed directly on a mat 70 including lower material layers 70a and 70b. After the extrudate material 60 is formed on top of lower material layers 70a and 70b (and sufficiently hardened) upper material layers 70c and 70d may be added. Extrudate material 60 may be fixedly coupled to upper and lower material layers 70a-70d by adhesive or by a heater that may melt the extrudate material 60 and upper and lower material layers 70a-70d such that they fuse together. Next, first vertical material layer 70e and second vertical material layer 70f may be added. First and second vertical materials 70e, 70f may be formed of the same material as upper and lower material layers 70a-70d or they may be formed of any alternate material previously disclosed. First and second vertical materials 70e, 70f may be fixedly coupled to side portions of the upper and lower material layers 70a-70d and extrudate material 60 by adhesive or by a heater that may melt the extrudate material 60 and upper and lower material layers 70a-70d such that they fuse together. In some embodiments, at least one of material layers 70a-70f may be printed or formed in-situ. In other embodiments, each of material layers 70a-70f may be printed or formed in-situ. In other embodiments, first and second vertical material layers 70e, 70f may be mechanically fastened to side portions of upper and lower material layers 70a-70d, for example hooks, bolts, pins, screws, etc. Furthermore, in some embodiments at least one of material layers 70a-70f may be printed in-situ around the extrudate material 60 continuously to encapsulate it. For example, extrudate material may be first fused to lower material layers 70a, 70b and then placed in a surgical access space of a patient by robotic armature 40. Then controller 1050 may finish printing material layers 70c-70f in-situ to form a finished implant according to the specific and particular custom requirements as may be determined by the additive manufacturing printing plan.

Figure 61A:
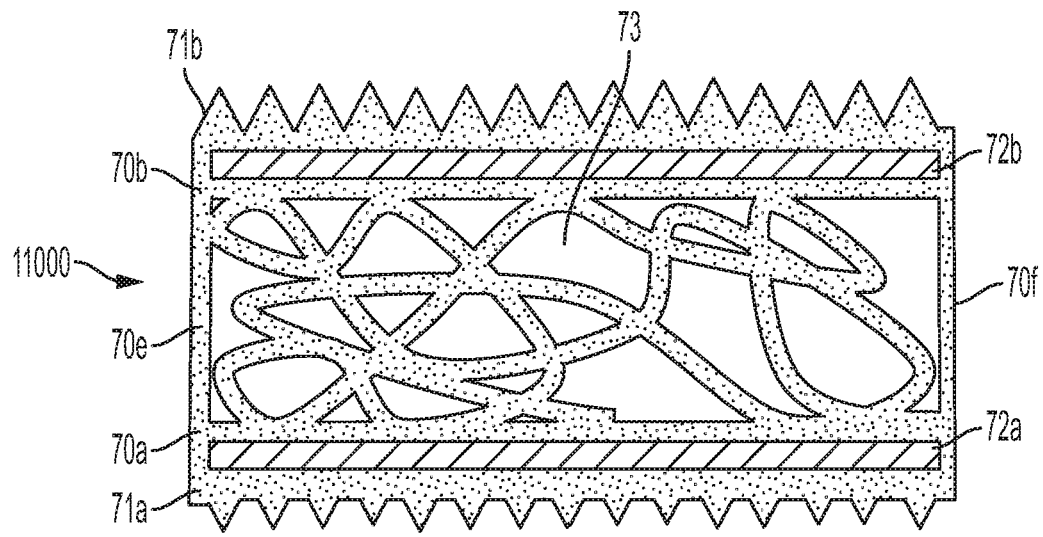
FIG. 61A shows a lateral view of an additive-manufactured non-woven fibrous implant including a plurality of engagement features for securing the implant between adjacent vertebrae of a patient.

FIG. 61A shows a lateral view of an additive-manufactured non-woven fibrous implant 11000 including a plurality of engagement features for securing the implant between adjacent vertebrae of a patient. The disclosed embodiment may be manufactured in the same, similar, or substantially the same way as implant 10000 and/or as may be consistent with other previously disclosed embodiments. For example, extrudate material 60 may be formed on top of material layers 70a and 70b. In the disclosed embodiment, material layer 70a is formed of a consistent rigid material chosen from any previously disclosed rigid material according to any previously disclosed manufacturing process. Material layer 71a may be formed of a metallic material, such as titanium, and may be machined or otherwise formed to include a plurality of engagement features and/or anti-migration features (illustrated schematically as triangular spikes). In the disclosed embodiment, material layer 70a and material layer 71a are coupled together by a pliable material 72a therebetween. Pliable material 72a may couple the metallic engagement features of material layer 71a to the rigid material of material layer 70a. In other embodiments, material layer 70a and material layer 71 may be adhered or otherwise fused directly together according to any previously disclosed manufacturing process. Similarly, material layer 70b and material layer 71b may be coupled together by a pliable material 72b therebetween. Pliable material 72b may couple the metallic engagement features of material layer 71b to the rigid material of material layer 70b. Vertical material layers 70e, 70f may be coupled to end portions of material layers 70a, 71a, 72a, and 70b, 71b, 72b as previously disclosed. However, in the disclosed embodiment, a relatively large portion of implant 11000 directly exposes the extrudate material 60. In this way, the extrudate material 60, forming a non-woven fibrous portion (or a non-woven fibrous component 63) is exposed, i.e., it is not covered fully by illustrated material layers 70a, 71a, 72a, and 70b, 71b, 72b. A particular advantage of an exposed or non-covered non-woven fibrous portion is that the human body may more easily form boney ingrowth material in the void spaces 73. In this way, the subject non-woven fibrous implant 11000 may be considered porous or semi porous and such pores may be defined by the random irregularly formed extrudate material fibers. Additionally, in other embodiments, apertures or void spaces may be formed and/or machined in material layers 70a, 71a, 72a, and 70b, 71b, 72b to expose non-woven fibrous portion defined by extrudate material 60. For example, in at least one embodiment through holes are formed by a printing process or through holes are drilled by a machined process.

It shall be understood that pliable materials 72a, 72b may be formed of the same pliable material or of different pliable materials. Likewise, metallic materials 71a, 71b may be formed of the same metallic material or of different metallic materials. Likewise still, rigid materials 70a, 70b may be formed of the same rigid material or a different rigid material. Moreover, controller 1050 may determine appropriate material compositions of any of the aforementioned layers 70a, 70b, 70e, 70f, 71a, 71b, 72a, 72b based on the pre-established additive-manufactured printing plan.

Figure 61B:
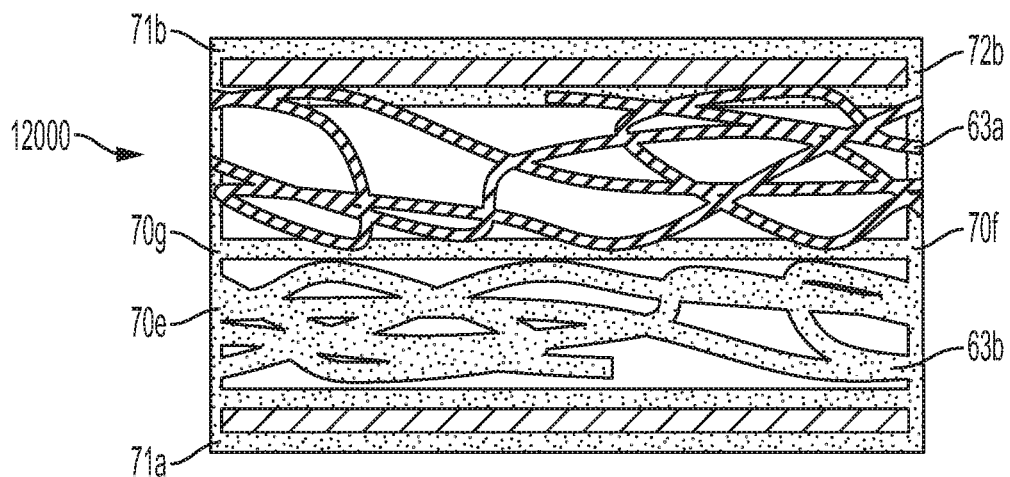
FIG. 61B shows a lateral view of an additive-manufactured non-woven fibrous implant including a first fibrous layer and a second fibrous layer.

FIG. 61B shows a lateral view of an additive-manufactured non-woven fibrous implant 12000 including a first non-woven fibrous component 63a and a second non-woven fibrous component 60b. First non-woven fibrous component 60a may have a different density of fibers than second non-woven fibrous component 60b due to being from different batches of non-woven fibrous material as previously explained. For example, first non-woven fibrous component 60a may be formed with a first die 113 having an exit orifice configured to extrude extrudate 60 having a first cross-sectional diameter and second non-woven fibrous component 60b may be formed with a second die 113 having an exit orifice configured to extrude extrudate 60 having a second cross-sectional diameter that is greater than the first cross-sectional diameter. Additionally, in some embodiments the first non-woven fibrous component 60a may be formed of a different material than the second non-woven fibrous component 60b. First non-woven fibrous component 60a and second non-woven fibrous component 60b may be separated by material layer 70g. Material layer 70g may be formed of a pliable, rigid, or metallic material. Material layers 70a, 70b, 70e, 70f, 71a, 71b, 72a, 72b of FIG. 61b may be the same, similar, or substantially the same as material layers 70a, 70b, 70e, 70f, 71a, 71b, 72a, 72b previously disclosed with respect to FIG. 61a.

In the disclosed embodiments of FIGS. 60A-60B, controller 1050 may have determined that a composite additive-manufactured non-woven fibrous implant 11000, 12000 formed of a combination of rigid and pliable material should include at least one material or layer printed in-situ between adjacent vertebrae 120, 122 of a patient. Such rigid and/or pliable materials may be printed around non-woven fibrous component 63. Exemplary rigid materials may be and/or include PMMA, PTFE, polyurethanes, Polyether ether ketone (PEEK), Polyetherketoneketone (PEKK) and other thermoplastic materials and relevant biocompatible materials having a modulus of elasticity generally within the range of boney structures as explained hereinabove. In some embodiments, a rigid material may have a modulus of elasticity roughly corresponding to a vertebrae, and in other embodiments a rigid material may have a modulus of elasticity roughly corresponding to the annulus fibrosis. Exemplary pliable materials may be and or include silicone, polyurethanes, hydrogels, polyvinyl, and other relevant biocompatible materials having a modulus of elasticity generally less than the range of boney structures as explained hereinabove. In some embodiments, a pliable material may have a modulus of elasticity roughly corresponding to the nucleus pulposus. In other embodiments, a pliable material may have a modulus of elasticity roughly corresponding to the annulus fibrosus. However, it shall be understood that the disclosed embodiments are exemplary and that controller 1050 may determine a rigid or semi-rigid material and/or non-woven fibrous components having different material compositions shall be used based on the particular variables of the specific patient being treated. In this way, controller 1050 may determine a custom surgical procedure for each particular patient.

Consistent with the inventive concepts of the disclosure herein, controller 1050 may base the additive-manufactured printing plan on (1) fiber properties including material type, fiber thickness, fiber length, etc.; (2) density of the fibers; (3) a mechanical strength between bonds of the fibers, (4) and treatments of the fibers before, during, and after extrusion.

Various layering as represented generally by the alternating hatching of the figures is intended solely to represent different material types and should not be construed as limiting the disclosed embodiments to any particular material or material relationship. Consistent with the above disclosure with respect to implants 10000, 11000, and 12000 each implant may be further configured with at least one aperture configured to receive an anchor, e.g., a bone screw or the like, for anchoring into an adjacent vertebrae. The anchor may help maintain the corresponding implant 10000, 11000, 12000 in contact with the adjacent vertebrae to facilitate load distribution.

ADDITIONAL EXAMPLE ASPECTS

Further regarding protecting the patient during the procedure, as mentioned above, in various embodiments, such as those involving application of chemical and/or heat in implant formation, care should be taken to ensure that patient tissue is not exposed to undesirable affects, including by not limited to undesirable levels of heat. It is also considered that the process could include cold fusing of materials. One example of such includes leveraging a cement reaction. These are other ways to protect the patient from extreme temperatures or conditions.

Further regarding customizing implant formation and structure to patient anatomy, as mentioned above, gauge(s) can be used to facilitate registering patient bone quality and adjusting the implant accordingly. For instance, if the gauge senses weak, or relatively weaker bone material adjacent the dispensing component 110, the system 100 (e.g., computing controller 1050) could apply material accordingly, such as in higher volume or in a special configuration to better address the weakness, such as by a configuration that covers more surface area at, in, or adjacent the weak area. And as mentioned the converse can be true. That is, less material or a special configuration can be used when strong bone is detected, such as by using less material, which can save material and time, and so cost, and be less invasive. In an additional aspect, the system 100 can in response to gauge recordings or other patient anatomy data (from imaging, etc.), form more or less channeling or voids, to guide bone growth into the implant more selectively, such as by promoting more bone growth in certain areas of the patient/implant.

Further regarding positive, or protruding features, as mentioned, the implant could be printed with protrusions, such as spikes, such that moving the adjacent vertebral body/ies to contact the implant would drive the protrusions into the vertebral body/ies, promoting implant securement in place. Along with or instead of spikes, these positive features (versus negative features like channels, holes, etc.) can include, for instance, teeth, ridges, detents, convexities, one-way teeth, the like, or other.

In a contemplated embodiment, positive features and negative features are formed and function together. A channel within an implant according to the present technology could have formed on its wall/s, for instance, a positive feature, such as a protrusion. Such positive feature/s within a negative feature can provide benefits such as promoting stronger bone in-growth to implant connectivity, and stronger resulting implant construct. Conversely, any implant positive feature, such as an outer surface protrusions, could have negative features formed therein, such as dimpling, holes, micro-channels, or the like. Benefits can include improved gripping (implant to patient), or increased bone in-growth to the implant, for example.

Any of the features disclosed with respect to any embodiments can be implemented with any of the other embodiments provided herein. Printing-material options described herein according to one or more embodiments can be used for implementing any of the other embodiments, for instance.

Any features from one or more embodiments can be implemented with any features described with respect to any other embodiment.

It should be understood that various aspects disclosed herein may be combined in combinations other than the combinations presented specifically in the description and the accompanying drawings. It should also be understood that, depending on the example, certain acts or events of any of the processes or methods described herein may be performed in other sequence, added, merged, or left out altogether (e.g., all described acts or events may not be necessary to carry out the techniques).

Any disclosure or claim herein referencing direction is not meant to limit interpretation of the disclosure, unless the disclosure or claim requires expressly such limitation. Reference, for instance, to depositing material on a vertebral surface is not limited to including printing on top of a generally horizontally disposed vertebral surface, and can include, for instance, printing on a partially or fully vertically disposed vertebral surface, for instance. As another example, references to a top or bottom of a grown or formed implant are not limited to indicating only an upper and a lower surface of the implant in a standing-patient reference frame.

Further regarding indications of direction, positioning and movement described in connection with components including but not limited to the dispensing component 110 are not restricted to the positioning and movement shown by way of examples in the figures. Actual positions and movements of the system 100 in use can be determined, pre-procedure or intra-procedure, by the computing controller 1050 and/or the surgeon or other surgical staff, and may differ from the positions and movements described or illustrated.

In addition, while certain aspects of this disclosure are described as being performed by a single module or unit for purposes of clarity, it should be understood that the techniques of this disclosure may be performed by a combination of units or modules. And aspects described as being performed by multiple modules or units, may be performed by a single module or unit in alternative embodiments.

Unless defined specifically otherwise herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an," and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed:

1. A non-woven fibrous implant, comprising:
   a first endcap formed of a rigid material and having a size corresponding to size of a first vertebral body;
   a second endcap formed of a rigid material and having a size corresponding to size of a second vertebral body;
   at least one pliable material layer disposed between the first endcap and the second endcap, the pliable material layer being configured to provide a motion-sparing effect, and
   at least one non-woven fibrous component comprising a plurality of randomly spaced and oriented fibers defining a plurality of open pore spaces between adjacent fibers,
   wherein the open pore spaces are configured to promote boney ingrowth between adjacent fibers, and
   wherein each of the first endcap, the second endcap, and the pliable material layer are printed and cured in-situ, within a disc space of a patient, between the first and second vertebral bodies.

2. The non-woven fibrous implant of claim 1, wherein the at least one non-woven fibrous component is configured to be exposed, at least partly, to patient tissue upon being positioned between adjacent vertebrae of a patient.

3. The non-woven fibrous implant of claim 1, wherein the at least one non-woven fibrous component is coated with a bone-growth-promoting material.

4. The non-woven fibrous implant of claim 1, wherein the at least one non-woven fibrous component comprises calcium and/or phosphate.

5. The non-woven fibrous implant of claim 1, wherein the at least one non-woven fibrous component is cut from a batch of fibrous material extruded directly in a turbulent airflow environment.

6. The motion-sparing spinal implant of claim 1, wherein the first endcap and the second endcap are formed of rigid material dispensed by a dispensing component.

7. The motion-sparing spinal implant of claim 1, wherein the first endcap and the second endcap are provided from pre-formed metallic material.

8. An additive-manufacturing system for forming at least one non-woven fibrous implant, comprising:
   a robotic subsystem including:
     scanning and imaging equipment configured to scan a patient's anatomy; and
     an armature including at least one dispensing nozzle configured to selectively dispense at least one rigid material and at least one pliable material;
   a controller apparatus having a processor and a non-transitory computer-readable medium storing computer-executable instructions configured to, when executed by the processor, cause the controller to:
     send a control signal to control the scanning and imaging equipment to determine a target alignment of a patient's spine;
     develop an additive-manufactured printing plan including an additive-manufactured material selection plan based on the target alignment of the patient's spine; and
     execute the additive-manufactured printing plan to:
       control the armature to dispense the at least one material chosen from the at least one rigid material and the at least one pliable material to form a non-woven fibrous component,
       wherein the non-woven fibrous component defines a plurality of randomly oriented fibers further defining a plurality of open pore spaces between adjacent fibers configured to facilitate boney ingrowth between adjacent fibers.

9. The additive-manufacturing system of claim 8, further comprising a provisioning component for affecting a rate of flow of printing material and a type of printing material through the dispensing nozzle,
   wherein the controller apparatus is further configured to control the provisioning component on the basis of the additive-manufactured printing plan and the additive-manufactured material selection plan.

10. The additive-manufacturing system of claim 8, wherein the controller apparatus is further configured to control forming the at least one non-woven fibrous component from an extruded material subjected to a turbulent airflow.

11. The additive-manufacturing system of claim 8, further comprising an extruder configured to extrude fibrous material into an environment subjected to a turbulent airflow.

12. The additive-manufacturing system of claim 8, further comprising an extruder and a pumping system configured to pump extrudate to the dispensing nozzle,
   wherein the dispensing nozzle ejects the extrudate into an environment subjected to a turbulent airflow to form the at least one non-woven fibrous component.

13. The additive-manufacturing system of claim 12, further comprising a robotic armature,
   wherein the computer-executable instructions are further configured to, when executed by the processor, cause the controller apparatus to send a control signal directing the robotic armature to place the at least one non-woven fibrous component inside a patient, and
   wherein the computer-executable instructions are further configured to, when executed by the processor, cause the controller apparatus to send a control signal directing the dispensing nozzle to print at least one of a rigid material and pliable material in-situ within the patient that directly contacts the non-woven fibrous component.

14. A method for printing an additive manufactured non-woven fibrous implant, comprising:
   positioning, in a first positioning step, a dispensing component proximate to an environment subjected to a turbulent airflow;
   printing, in a printing step, a fibrous material within the environment subjected to the turbulent airflow to form at least one non-woven fibrous component;
   coupling at least one rigid material to the at least one non-woven fibrous component; and
   placing the non-woven fibrous component inside an interbody access space of a patient.

15. The method of claim 14, further comprising:
   providing an additive-manufacturing system including a robotic subsystem and a controller apparatus having a processor and a non-transitory computer-readable medium storing additive manufactured printing instructions; and executing the additive manufactured printing instructions to control the robotic subsystem to perform the printing steps.

16. The method of claim 14, wherein:

the additive-manufacturing system further comprises a provisioning component affecting flow of printing material to or through the dispensing component; and the controller apparatus, in the printing step, controls the provisioning component based on turbulent airflow data to control a rate at which the printing material is dispensed.

17. The method of claim 16, further comprising printing another rigid material or a pliable material within or adjacent to the interbody access space of the patient that directly contacts the non-woven fibrous component.

18. A non-woven fibrous implant, comprising:

a first endcap formed of a rigid material and having a size corresponding to size of a first vertebral body;

a second endcap formed of a rigid material and having a size corresponding to size of a second vertebral body;

at least one pliable material layer disposed between the first endcap and the second endcap, the pliable material layer being configured to provide a motion-sparing effect, and at least one non-woven fibrous component comprising a plurality of randomly spaced and oriented fibers defining a plurality of open pore spaces between adjacent fibers, wherein the open pore spaces are configured to promote boney ingrowth between adjacent fibers, and wherein the at least one non-woven fibrous component is cut from a batch of fibrous material extruded directly in a turbulent airflow environment.

19. The non-woven fibrous implant of claim 18, wherein at least one of the first endcap, the second endcap, and the pliable material layer are printed and cured in-situ, within a disc space of a patient, between the first and second vertebral bodies.

* * * * *